US012622685B2

(12) United States Patent
Mohammadpour et al.

(10) Patent No.: US 12,622,685 B2
(45) Date of Patent: May 12, 2026

(54) LARGE TISSUE DEFECT RECRUITING DEVICE

(71) Applicant: United States Endoscopy Group, Inc., Mentor, OH (US)

(72) Inventors: Reza Mohammadpour, Willoughby Hills, OH (US); Alex Uspenski, Chardon, OH (US); Keith Randall John, Chardon, OH (US); Seth Byers, Madison, OH (US); Brittany Ochs, Painesville, OH (US); Michael C. Hauser, Chardon, OH (US); Meha Elango, Copley, OH (US); Brett DuFour, Mentor, OH (US)

(73) Assignee: United States Endoscopy Group, Inc., Mentor, OH (US)

( * ) Notice: Subject to any disclaimer, the term of this patent is extended or adjusted under 35 U.S.C. 154(b) by 251 days.

(21) Appl. No.: 18/199,888

(22) Filed: May 19, 2023

(65) Prior Publication Data

US 2023/0371938 A1      Nov. 23, 2023

Related U.S. Application Data

(60) Provisional application No. 63/344,063, filed on May 20, 2022.

(51) Int. Cl.
A61B 17/08       (2006.01)
A61B 17/00       (2006.01)
(Continued)

(52) U.S. Cl.
CPC ........ A61B 17/00234 (2013.01); A61B 17/08 (2013.01); A61B 17/1285 (2013.01);
(Continued)

(58) Field of Classification Search
CPC ........................... A61B 17/00234; A61B 7/08
(Continued)

(56) References Cited

U.S. PATENT DOCUMENTS

| | | | |
|---|---|---|---|
| 4,694,544 A | 9/1987 | Chapman | |
| 5,336,230 A | 8/1994 | Leichtling et al. | |

(Continued)

FOREIGN PATENT DOCUMENTS

| | | |
|---|---|---|
| WO | WO2004103430 A2 | 12/2004 |
| WO | 2019182148 A1 | 9/2019 |

OTHER PUBLICATIONS

International Search Report from PCT/US2023/023016 dated Sep. 12, 2023 (14 pages).

(Continued)

*Primary Examiner* — Nicole F Johnson
(74) *Attorney, Agent, or Firm* — Calfee, Halter & Griswold LLP

(57)       ABSTRACT

A tissue recruiting device for treating and closing a defect and methods of using the same. The tissue recruiting device includes a tissue recruiting assembly with two grasping devices and a shroud. An actuation assembly couples control actuators to the grasping devices via actuation elements. The grasping devices may be maneuvered to grasp tissue from different locations by actuation of the control actuators. The grasping devices may be retracted into a shroud to substantially close the defect. The grasping devices and the shroud may be decoupled from the remainder of the tissue recruiting assembly to maintain closure of the defect.

20 Claims, 50 Drawing Sheets

(51) Int. Cl.

| | |
|---|---|
| *A61B 17/128* | (2006.01) |
| *A61B 17/29* | (2006.01) |
| *A61B 17/12* | (2006.01) |

(52) U.S. Cl.
CPC ...... *A61B 17/29* (2013.01); *A61B 2017/0034* (2013.01); *A61B 2017/00349* (2013.01); *A61B 2017/00371* (2013.01); *A61B 2017/00867* (2013.01); *A61B 2017/081* (2013.01); *A61B 2017/12004* (2013.01)

(58) Field of Classification Search
USPC ............................................................. 606/1
See application file for complete search history.

(56) References Cited

U.S. PATENT DOCUMENTS

| | | | |
|---|---|---|---|
| 5,478,351 | A | 12/1995 | Meade et al. |
| 5,511,564 | A | 4/1996 | Wilk |
| 6,126,665 | A | 10/2000 | Yoon |
| 9,486,126 | B2 | 11/2016 | West et al. |
| 9,603,614 | B2 | 3/2017 | Schurr et al. |
| 10,639,031 | B2 | 5/2020 | Binmoeller et al. |
| 2002/0156344 | A1 | 10/2002 | Pasricha et al. |
| 2003/0187457 | A1* | 10/2003 | Weber ............ A61B 17/320016 |
| | | | 606/110 |
| 2005/0251160 | A1 | 11/2005 | Saadat et al. |
| 2009/0024156 | A1 | 1/2009 | Chin |
| 2009/0131747 | A1 | 5/2009 | Chin et al. |
| 2011/0118543 | A1 | 5/2011 | Dosher et al. |
| 2012/0123528 | A1* | 5/2012 | Knippel ................ A61F 2/2436 |
| | | | 623/2.11 |
| 2012/0165842 | A1 | 6/2012 | Stokes et al. |
| 2013/0006287 | A1 | 1/2013 | West et al. |
| 2014/0058418 | A1 | 2/2014 | Romley |
| 2014/0257338 | A1 | 9/2014 | Romley |
| 2015/0057704 | A1 | 2/2015 | Takahashi |
| 2015/0065938 | A1 | 3/2015 | Zeiner et al. |
| 2017/0150952 | A1 | 6/2017 | Romley |
| 2018/0028180 | A1 | 2/2018 | Binmoeller et al. |
| 2018/0249987 | A1 | 9/2018 | Costello et al. |
| 2019/0000439 | A1* | 1/2019 | Gustafson ........ A61B 17/06061 |
| 2019/0274699 | A1 | 9/2019 | Morey et al. |
| 2019/0328528 | A1 | 10/2019 | Purcell et al. |
| 2020/0178956 | A1 | 6/2020 | Mitelberg et al. |
| 2021/0128126 | A1 | 5/2021 | Windheuser et al. |

OTHER PUBLICATIONS

International Search Report from PCT/US2023/023026 dated Sep. 18, 2023 (12 pages).

International Search Report from PCT/US2023/023027 dated Sep. 18, 2023 (11 pages).

Mangiavillano et al., Over the scope clips in the treatment of gastrointestinal tract iatrogenic perforations, World Journal of Gastrointestinal Surgery, Apr. 27, 2016, 8(4); 315-320.

Tang et al., Double channel double grasper technique in over the scope clip deployment,gastrointestinal endoscopy, www.videogie.org, vol. 5, No. 4, 2020, 141-143.

Extended European Search Report and Opinion dated Feb. 17, 2026 for EP Application No. 23808427.1, filed Oct. 25, 2024.

Extended European Search Report and Opinion dated Feb. 17, 2026 for EP Application No. 23808424.8, filed Oct. 25, 2024.

Extended European Search Report and Opinion dated Feb. 17, 2026 for EP Application No. 23808426.3, filed Oct. 25, 2024.

* cited by examiner

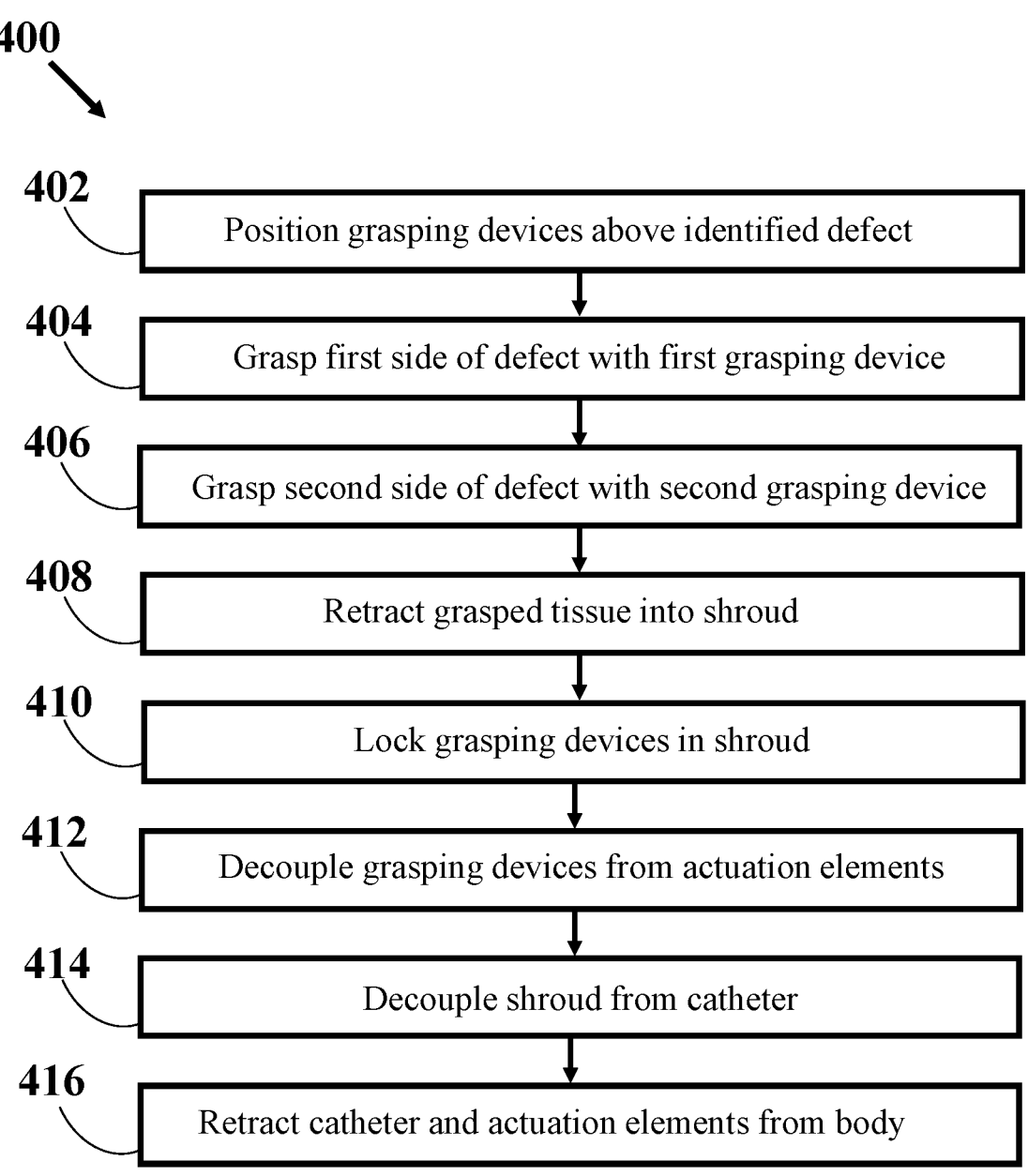

402 — Position grasping devices above identified defect

404 — Grasp first side of defect with first grasping device

406 — Grasp second side of defect with second grasping device

408 — Retract grasped tissue into shroud

410 — Lock grasping devices in shroud

412 — Decouple grasping devices from actuation elements

414 — Decouple shroud from catheter

416 — Retract catheter and actuation elements from body

FIG. 40

LARGE TISSUE DEFECT RECRUITING DEVICE

CROSS-REFERENCE TO RELATED APPLICATIONS

The present application claims priority to U.S. Provisional Patent Application No. 63/344,063, filed on May 20, 2022, the entire disclosure of which is incorporated herein by reference as though recited herein its entirety.

TECHNICAL FIELD

The present disclosure relates generally to surgical devices and, more specifically, to a tissue recruiting device that allows for improved tissue recruitment tissue.

BACKGROUND

Tissue grasping and recruiting devices are used in various parts of the body, including the gastrointestinal, urinary, and vascular systems, to treat internal bleeding or defects. These devices may be deployed using an endoscope, such as a flexible endoscope, and may be provided in a variety of forms and may be used with hemostatic devices, including clamps, clips, staples, sutures, and the like. One or more hemostatic devices may be deployed around tissue in the body to apply constrictive forces to blood vessels and surrounding tissue, such as to control and prevent bleeding.

In some cases, a hemostatic device may be deployed around a growth of tissue, such as a polyp. The hemostatic device may be used to close the defect after the growth has been removed, such as to prevent or otherwise reduce bleeding. In other cases, target tissue may be recruited, such as into a pseudo-polyp, and the hemostatic device may be used to close the defect after the recruited tissue has been cut or severed, such as to remove the defect. The target tissue could be dysplasia, a defect, or the like. However, in some cases, particularly those involving larger defects and fibrotic tissue, it can be difficult to utilize conventional hemostatic devices to successfully close the defect.

Most hemostatic devices rely on variations of conventional tissue recruiting techniques to recruit tissue before the hemostatic device is deployed. Conventional tissue recruiting techniques often involve extending a tissue recruiting device through an endoscope to the desired location to recruit tissue. However, conventional tissue recruitment techniques can sometimes fail to adequately recruit tissue before the hemostatic device is deployed. For example, conventional tissue recruitment techniques may fail to adequately grasp and recruit multiple sides of a defect. Additionally, needing to deploy a hemostatic clip to close the defect may be difficult, cumbersome, and expensive. Accordingly, there is an unmet need for an improved recruiting device that utilizes separate, independently controlled graspers to improve tissue recruitment.

SUMMARY

This summary is meant to provide some examples and is not intended to be limiting of the scope of the invention in any way. For example, any feature included in an example of this summary is not required by the claims, unless the claims explicitly recite the features. Also, the features, components, steps, concepts, etc. described in examples in this summary and elsewhere in this disclosure can be combined in a variety of ways. The description herein relates to systems, assemblies, methods, devices, apparatuses, combinations, etc. that may be utilized for recruiting tissue, such as a tissue defect. Various features and steps as described elsewhere in this disclosure may be included in the examples summarized here. Further, the treatment techniques, methods, operations, steps, etc. described or suggested herein can be performed on a living animal or on a non-living simulation, such as on a cadaver, simulator (e.g., with the body parts, tissue, etc. being simulated), etc.

In one example embodiment, a tissue recruiting device is provided. The tissue recruiting device includes a catheter and a tissue recruiting device with first and second grasping devices and a shroud a shroud operably coupled with the catheter and configured to at least partially surround the grasping devices in a retracted position. The tissue recruiting device also includes an actuation assembly with a first control actuator coupled with a first actuation element, the first actuation element being operably coupled with the first grasping device, and a second control actuator coupled with a second actuation element, the second actuation element being operably coupled with the second grasping device. The first control actuator is operable to maneuver the first grasping device to grasp tissue at a first location and the second control actuator is operable to maneuver the second grasping device to grasp tissue at a second location. The grasping devices may be decoupled from the actuation elements and the shroud may be decoupled from the catheter when the grasping devices grasp tissue.

In one example embodiment, a tissue recruiting assembly of a tissue recruiting device operable to extend through a catheter and grasp tissue is provided. The tissue recruiting assembly includes a first grasping device operably coupled to a first actuation element by a first coupler and a second grasping device operably coupled to a second actuation element by a second coupler. The tissue recruiting assembly also includes a shroud configured to surround the first and second grasping devices and a connector configured to operably couple the shroud to the catheter. The first grasping device may be controlled by the first actuation element to grasp tissue at a first location and the second grasping device may be controlled by the second actuation element to grasp tissue at a second location. The grasping devices may be retracted into the shroud and locked in place when grasping tissue. The grasping devices are operably decoupled from the actuation elements and the shroud is operably decoupled from the catheter after the grasping devices are retracted into the shroud.

In one example embodiment, a method for treating a defect with a tissue recruiting device is provided. The method includes the steps of grasping a first side of the defect with a first grasping device via a first actuation element, grasping a second side of the defect with a second grasping device via a second actuation element, retracting the first and second grasping devices into a shroud coupled to a catheter, decoupling the first grasping device from the first actuation element and the second grasping device from the second actuation element, and decoupling the shroud from the catheter.

These and other objects, features, and advantages of the present disclosure will become apparent from the following detailed description of illustrative embodiments thereof, which is to be read in connection with the accompanying drawings.

BRIEF DESCRIPTION OF THE DRAWINGS

To further clarify various aspects of implementations of the present disclosure, a more particular description of the certain examples and implementations will be made by reference to various aspects of the appended drawings. These drawings depict only example implementations of the present disclosure and are therefore not to be considered limiting of the scope of the disclosure. Moreover, while the Figures can be drawn to scale for some examples, the Figures are not necessarily drawn to scale for all examples. Examples and other features and advantages of the present disclosure will be described and explained with additional specificity and detail through the use of the accompanying drawings in which:

FIG. 40 is an illustrative example depicting a methodology for closing a defect via two grasping devices.

DETAILED DESCRIPTION

Figure 1:
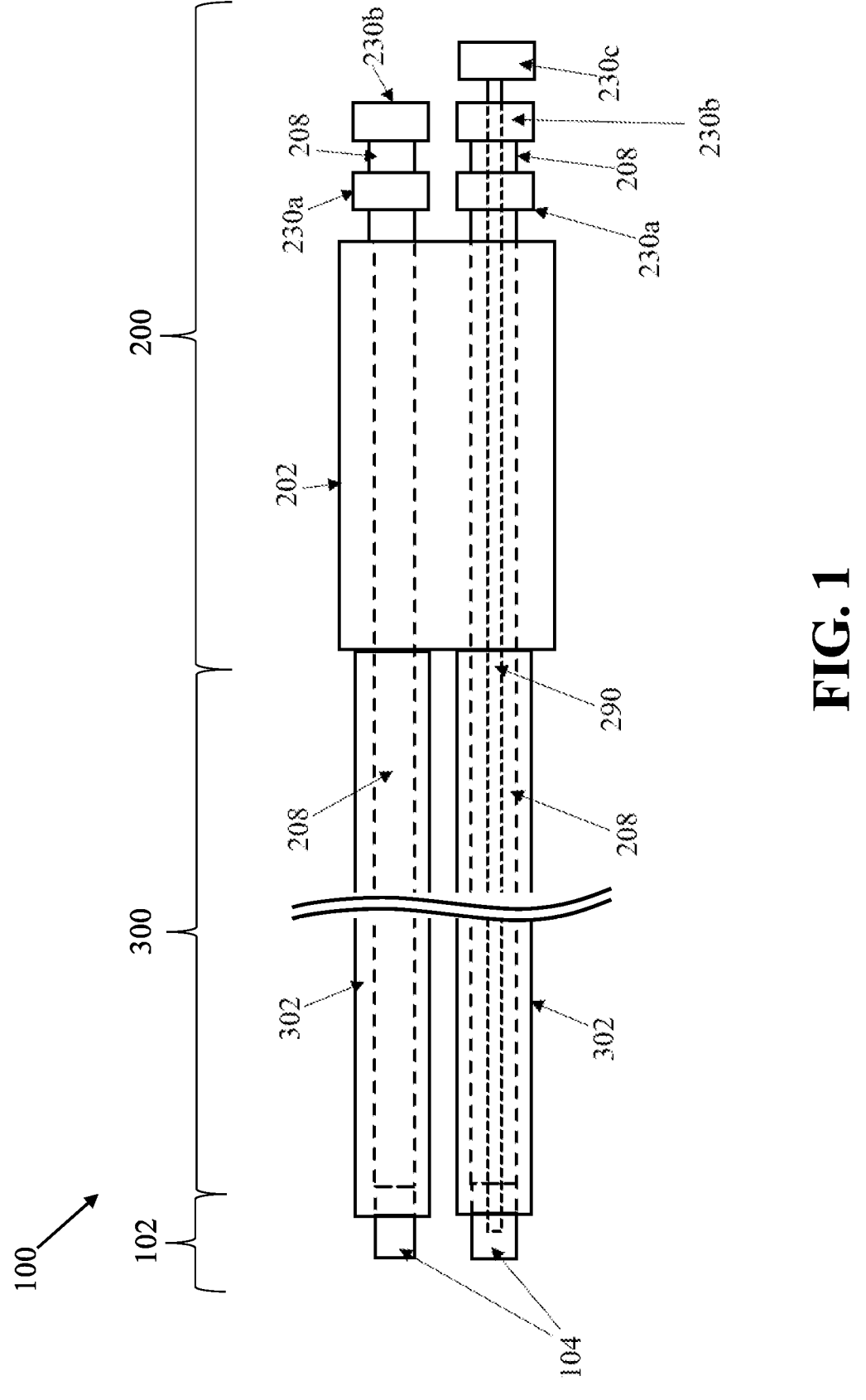
FIG. 1 is a schematic illustration of a tissue recruiting device.

The following description refers to the accompanying drawings, which illustrate specific embodiments of the present disclosures, and describes exemplary embodiments in accordance with the general inventive concepts and is not intended to limit the scope of the invention or the claims in any way. Indeed, the invention as described by the claims is broader than and not limited by the exemplary embodiments set forth herein, and the terms used in the claims have their full ordinary meaning.

The general inventive concepts will be understood more fully from the detailed description given below and from the accompanying drawings of the various exemplary aspects and implementations of the disclosure. This should not be taken to limit the general inventive concepts to the specific aspects or implementations, which are being provided for explanation and understanding only. Example embodiments of the present disclosure are directed to devices and methods for recruiting tissue. Various embodiments of devices and systems for recruiting tissue are disclosed herein, and any combination of these options can be made unless specifically excluded. In other words, individual components of the disclosed devices and systems can be combined unless mutually exclusive or otherwise physically impossible.

Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts. As used in this detailed description and the appended claims, the singular forms "a," "an," and "the" are intended to include the plural forms as well, unless the context clearly indicates otherwise.

As described herein, when one or more components are described as being connected, joined, affixed, coupled, attached, or otherwise interconnected, such interconnection can be direct as between the components or can be indirect such as through the use of one or more intermediary components. Also, as described herein, reference to a "member," "component," or "portion" shall not be limited to a single structural member, component, or element, but can include an assembly of components, members, or elements.

Unless otherwise indicated, all numbers, such as for example, numbers expressing measurements or physical characteristics, used in the specification and claims are to be understood as being modified in all instances by the term "about." Accordingly, unless otherwise indicated, the numerical properties set forth in the specification and claims are approximations that may vary depending on the suitable properties sought to be obtained in embodiments of the invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements. Also, as described herein, the terms "substantially" and "about" are defined as at least close to (and includes) a given value or state (preferably within 10% of, more preferably within 1% of, and most preferably within 0.1% of).

In discussing the exemplary embodiments herein, the terms "proximal" and "distal" may often be used. These terms are used to describe a position or a direction with reference to the operator of the instrument. For example, the proximal position or proximal direction is toward the user or operator of the instrument, and the distal position or direction is away from the user or operator of the instrument, i.e., position or direction toward the object which the operator is attempting to grasp, retain, and/or view.

The present invention provides a tissue recruiting device to be used through an endoscope. The tissue recruiting device may be configured to better approximate tissue than standard tissue recruiting devices. The tissue recruiting device may also be configured to recruit tissue over larger defects than standard tissue recruiting devices. For example, the tissue recruiting device of the present disclosure may be configured to approximate tissue defects having a width or diameter between about 1 cm and about 10 cm. In some embodiments, the tissue recruiting device is configured to approximate tissue defects larger than 10 cm in width or diameter. The tissue recruiting device of the present disclosure may also be configured to simultaneously approximate multiple sides of a defect, such as to achieve more consistent and circumferential closure of defects. The tissue recruiting device may be configured to achieve a more consistent and circumferential closure of a tissue defect, such as when a hemostatic device is deployed around the tissue recruited by the tissue recruiting device. While the device is described as being usable to close a defect, it may also be used to grasp intact tissue, such as dysplastic, T1A, T1B, and other tissue. In some embodiments, the tissue recruiting device may be a sterile, single use device such as to reduce cost.

Figure 2:
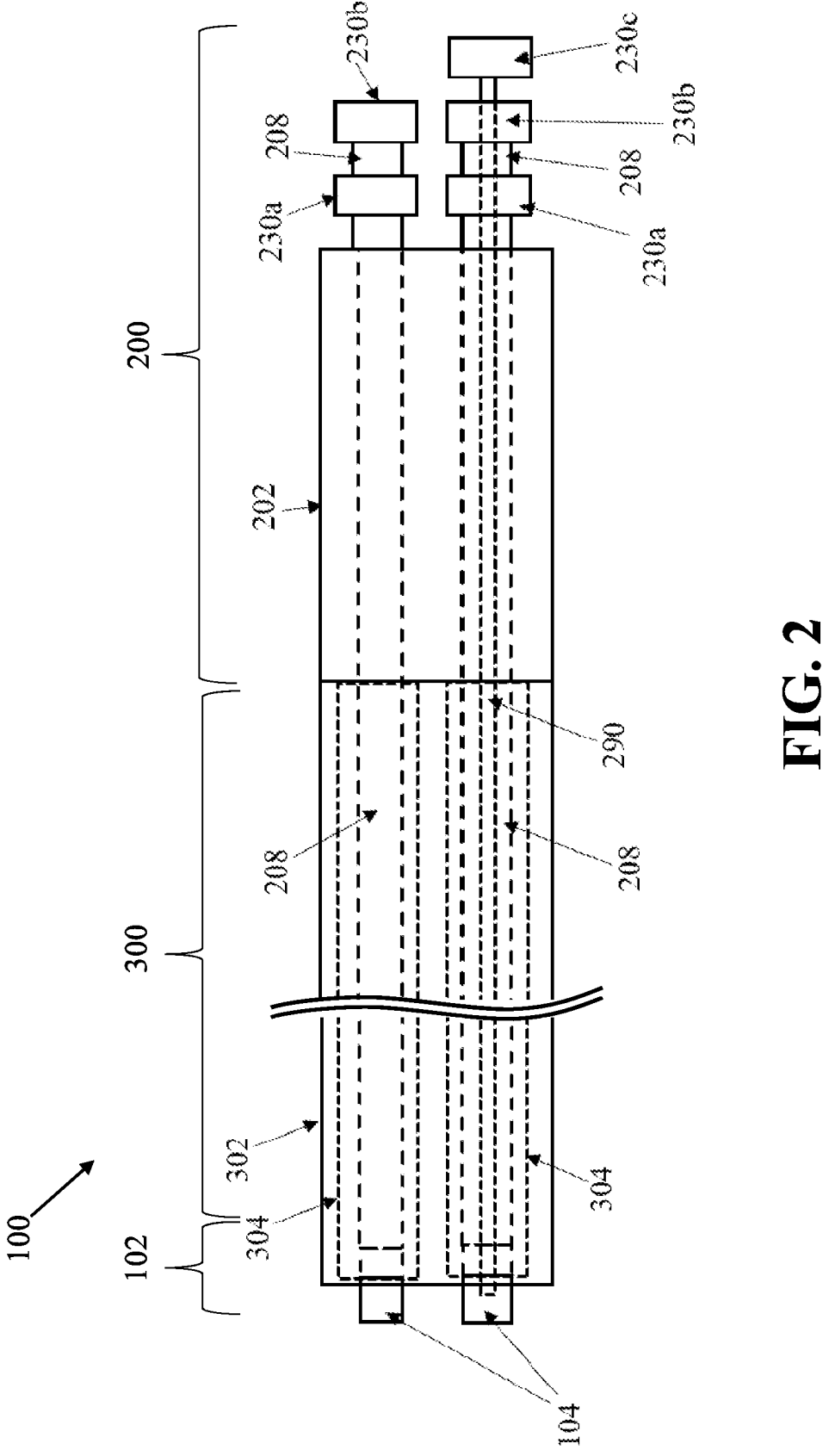
FIG. 2 is a schematic illustration of another tissue recruiting device.

A functional block diagram for a tissue recruiting device 100 is illustrated in FIGS. 1-2. The tissue recruiting device 100 includes a tissue recruiting assembly 102 at a distal end, an actuation assembly 200 at a proximal end, and a catheter sheath assembly 300 disposed between the tissue recruiting assembly 102 and the actuation assembly 200. The tissue recruiting assembly 102 may include one or more tissue grasping devices 104 configured to grasp. The grasping devices 104 may be end effectors or devices capable of grasping tissue. It will be understood that the grasping of the grasping devices 104 encompasses grabbing, pinching, hooking, or otherwise securing tissue with the grasping devices 104.

The proximal end of each grasping device 104 may be coupled with an actuation element 208 of the actuation assembly 200. Each actuation element 208 is configured to control the position and rotation of the attached grasping device 104, such as via operation of the actuation assembly 200. Each actuation element 208 may be configured to transfer both translational motion to position the grasping device 104 and torque or rotational motion to the grasping device 104 to rotate the grasping device 104. Each actuation element 208 may be a solid cable, a hollow tube, or other suitable elongated object or combination of objects, such as a drive cable, a torque cable, a hypotube, spring sheath, or a catheter, configured to control the grasping device 104.

In the illustrated embodiment, the tissue recruiting device 100 has two grasping devices 104 each coupled with an actuation element 208. However, the device 100 may have other assemblies and configurations. For example, the tissue recruiting assembly 102 may have one or three or more grasping devices 104 and the actuation elements 208 may be coupled to two or more grasping devices 104.

The catheter sheath assembly 300 includes one or more catheters 302 operably connected to the distal end of the actuation assembly 200. The tissue grasping devices 104 and the actuation elements 208 may extend through one or more lumens of the one or more catheters 302. In some embodiments, the proximal ends of the actuation elements 208 may extend through the proximal end of the catheters 302 to operably couple with other components of the actuation assembly 200, as described below. The one or more catheters 302 may be sized, shaped, and configured such that each grasping device 104 may be distally extended beyond the distal end of the one or more catheters 302 via the actuation elements 208 extending therethrough. In some embodiments, the catheter sheath assembly 300 is flexible to allow for adequate endoscope maneuverability without compromising the purchase of the tissue recruiting assembly 102, such as the purchase of the tissue recruiting assembly 102 has on multiple edges of a tissue defect.

As shown in FIG. 1, each grasping device 104 and actuation element 208 pair is disposed through a separate catheter 302. However, the catheter sheath assembly 300 may have other configurations and assemblies. For example, as shown in FIG. 2 each grasping device 104 and actuation element 208 pair may extend through a single catheter 302. The actuation elements 208 and grasping devices 104 may extend through separate lumens of the catheter 302 or all grasping devices 104 and actuation elements 208 may extend through a single lumen of a single catheter 302.

In some embodiments, the one or more catheters 302 comprise polyether ether-ketone (PEEK), a thermoplastic material, nylon, Pellethane, polytetrafluoroethylene (PTFE), polyimide, composite metal and polymer tubing, metal tubing, metal coils, or similar constructions known in the art, or combinations thereof. In a preferred embodiment, the catheters 302 are metal spring sheaths configured to resist compression and operational forces exerted on the catheters 302 by the actuation elements 208 and/or operational elements as described below. In some embodiments, the catheters 302 include a liner or a coating, such as a PTFE liner and/or coating, disposed in the one or more lumens to increase the resiliency of the catheters 302 and/or to decrease friction between the actuation elements 208 and the catheter 302.

Figure 3:
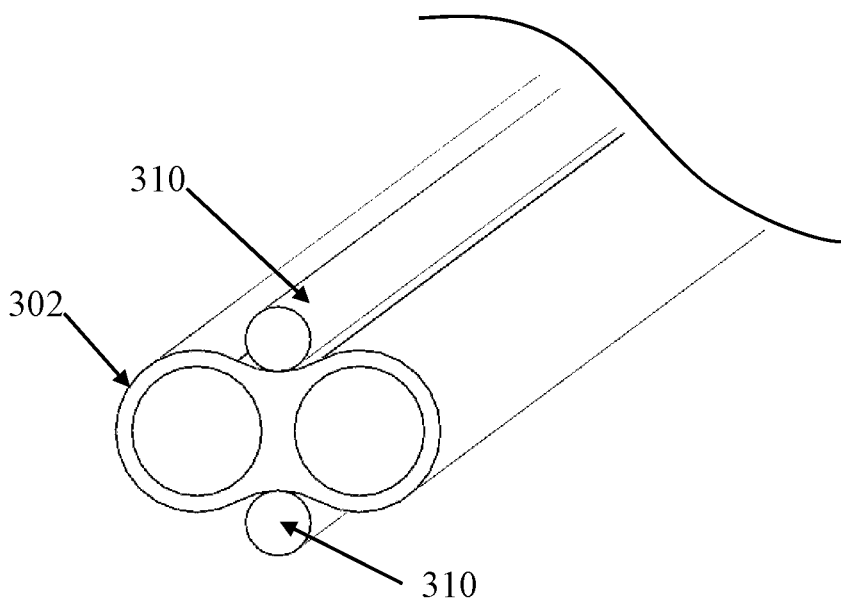
FIG. 3 is a perspective view of a catheter sheath assembly according to one embodiment of the disclosure.
Figure 4:
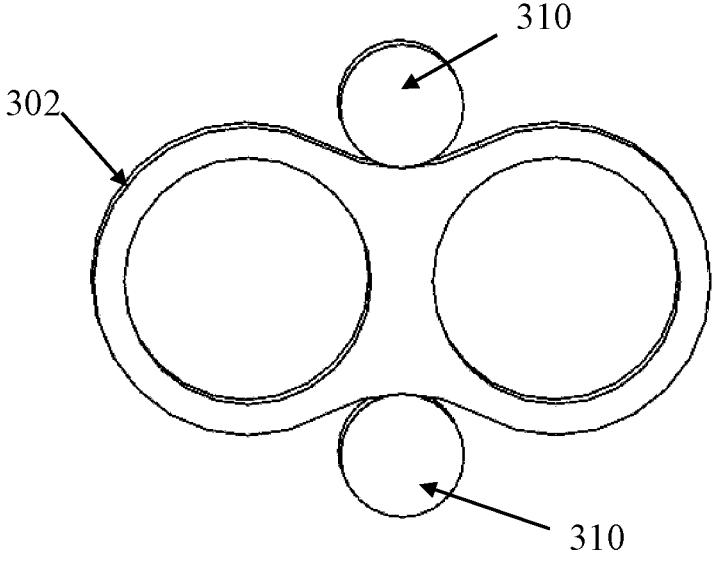
FIG. 4 is a front view of the catheter sheath assembly of FIG. 3.

In some embodiments, as shown in FIGS. 3-4, the catheter 302 is a dual-lumen catheter having a substantially figure-eight-shaped cross-section. The catheter sheath assembly 300 also includes one or more support wires 310 extending along the length of the catheter 302 between the lumens and above and/or below the outer surface of the catheter 302, such as in the rounded groove between the lumens. The support wires 310 may reinforce the catheter 302 to provide strength to the catheter and counter or reduce compressive forces encountered by the device 100 during operation. The support wires 310 may comprise stainless steel or a shape memory material, such as Nitinol. Additionally or alternatively, the support wires 310 may comprise PEEK, superelastic Nitinol, liquid crystalline polymer (LCP), or other metals or polymers with sufficient strength to resist compressive forces, or combinations thereof. The dual lumens of the catheter 302 may assist in the tissue grasping operation, such as by preventing the actuation elements 208 from tangling within the catheter 302.

While the catheter sheath assembly 300 of FIGS. 3-4 is shown as including two support wires 310 on the top and the bottom of the catheter 302, it will be understood that the catheter sheath assembly 300 may have other assemblies and configurations. For example, the catheter sheath assembly 300 may include one support wire 310 underneath the catheter 302, one support wire 310 above the catheter 302, or three or more support wires 310 disposed at various locations around the outer surface of the catheter 302.

Referring back to FIGS. 1-2, the grasping devices 104 may be disposed through a distal end of the endoscope and the catheter sheath assembly 300. In some embodiments, the grasping devices 104 may be operated by a user at a proximal end of the endoscope via the actuation elements 208 extending through a channel located within and extending through the endoscope, such as via the actuation assembly 200. In other embodiments, the device 100 may be used during minimally invasive procedure with a suitable natural or artificially created orifice in the body. The device 100 is constructed and configured such that it may be inserted into a subject through an orifice or small incision and operated to recruit target tissue, such as defected tissue. The device 100 may be configured to recruit tissue across large defects, such as tissue defects greater than 1 cm or tissue defects greater than 3 cm. In some embodiments, the device 100 is configured to recruit tissue across defects greater than 10 cm in diameter. Additionally, the device 100 may be configured to simultaneously recruit multiple sides of a defect, such as to achieve more consistent and circumferential closure of defects.

The device 100 can be used with any suitable or conventional endoscope or laparoscopic surgical equipment. For purposes of this disclosure, the device 100 is described in the context of use with an endoscope/colonoscope/sigmoidoscope type apparatus of conventional or suitable construction. However, the device may also be used in other manners, such as in any minimally invasive procedure with a suitable natural or artificially created orifice in the body. The scope is provided with an elongated body having a controllably flexible projecting end region. Surgical instruments, such as the device 100, may be introduced through an instrument channel, such as an accessory channel, which extends through the scope body, for recruiting tissue targeted by the surgeon manipulating the scope. The grasping devices 104 may be sized, shaped, and configured such that all the grasping devices 104 may be disposed through the same instrument or accessory channel of the endoscope.

Each grasping device 104 is configured to grasp tissue, such as defected tissue, such that the tissue recruiting device 100 may recruit the grasped tissue. The grasping devices 104 may be any suitable device for grasping tissue. For example, the grasping devices 104 may be forceps, clamps, hooks, pins, talons, or the like. Each of the tissue grasping devices 104 may be controlled by the actuation assembly 200, such as via the actuation element 208 to which the grasping device 104 is attached. In some embodiments, the grasping devices 104 are independently controllable via the actuation assembly 200.

The actuation assembly 200 may be operably connected to each grasping device 104 via one or more actuation elements 208. The actuation element 208 may be configured to control the translational and rotational movements of the respective grasping device 104. For example, the actuation elements 208 may be configured such that a user may position the grasping device 104, such as on a side of a defect, and deploy or otherwise manipulate the grasping device 104, such as to grasp tissue. The actuation elements 208 may be stiff or rigid enough to translate rotational and linear force to the grasping device 104, such as to aim and maintain the grasping device 104 at various positions and angles, during operation. The actuation elements 208 may also be flexible enough such that the actuation elements 208 may be disposed through a channel of the endoscope and/or the catheter 302 to the desired location and such that deployed or actuated grasping devices 104 may continue to grasp tissue as the endoscope and/or catheter sheath assembly 300 are manipulated. The actuation elements 208 may also be flexible enough such that a first grasping device 104 may be maneuvered to grasp tissue at a first location and a second grasping device 104 may be maneuvered to grasp tissue at a second location with the first grasping device 104 grasping tissue. In some embodiments, the actuation elements 208 comprise polymers, such as ABS, PC, acrylic, plastic, or metals, such as stainless steel or Nitinol, or combinations thereof.

In the illustrated embodiment, the actuation assembly 200 is operably connected to each grasping device 104 via a single actuation element 208. However, it will be understood that the tissue recruiting device 100 may have other suitable configurations. For example, the actuation assembly 200 may be operably connected to each grasping device 104 via multiple actuation elements 208, such as an actuation element 208 configured to control the translation of the grasping device 104 and an actuation element 208 configured to control the rotation of the grasping device 104.

In some embodiments, as shown in FIG. 2, the actuation elements 208 are operably disposed through one or more sheaths 304 disposed between the actuation elements 208 and the catheter 302. Each actuation element 208 may extend through a separate sheath 304 or the actuation elements 208 may extended through a single sheath 304, such as a single sheath 304 with two lumens or a sheath 304 with a single lumen. The one or more sheaths 304 may cover the actuation elements 208, as well as any additional control or operational elements, as they are extended through the endoscope and/or the catheter 302. The sheaths 304 may be configured to reduce friction between the actuation elements 208 and/or between the actuation elements 208 and the catheter 302. The sheaths 304 may also be configured to prevent the actuation elements 208 from tangling within the catheter 302. For example, the sheaths 304 may be implemented in embodiments in which the actuation elements 208 are disposed through a single catheter 302. The one or more sheaths 304 may be a spring sheath, a reinforced composite sheath, and/or a tubing, such as a polymer tubing and/or hypotubing. Further, it will be understood that the actuation elements 208 may be disposed directly through one or more lumens of the catheter 302, such as without a sheath 304.

The proximal end of each sheath 304 may be operably connected or otherwise coupled with the actuation assembly 200. The distal end of each sheath 304 may extend toward the respective grasping device 104. In some embodiments, the distal end of each sheath 304 is connected or otherwise coupled with the respective grasping device 104. The sheaths 304 may be sized, shaped, or configured to accommodate the actuation elements 208 therethrough. For example, the sheaths 304 may be hollow to at least partially cover the actuation element 208. In some embodiments, such as in embodiments in which one of the grasping devices 104 is operated via an operational element, the sheaths 304 may also be sized, shaped, or configured to accommodate the operational element therethrough.

In some embodiments, such as in embodiments in which one or more grasping device 104 may be operated (e.g., opened and closed), the actuation element 208 may be hollow, shaped, or sized to at least partially encompass an operational element 290 coupled with the grasping device 104 and configured to operate the grasping device 104. The operational element 290 may be a drive cable, a torque cable, a hypotube, spring sheath, a catheter, or other suitable member configured to control the grasping device 104. For example, each operational element 290 may be configured to convey translational and/or rotational force to actuate the grasping device 104. Alternatively, the operational element 290 may be disposed in parallel alongside the actuation element 208 (e.g., FIG. 6).

The operational element 290 may be movable, such as linearly movable and rotationally movable, relative to the actuation element 208 to control the function or operation of the grasping device 104 (e.g., opening and closing) separately from the translation and/or rotation of the grasping device 104. A proximal end of the operational element 290 may be operably coupled with the actuation assembly 200 such that a user may control the operation of the grasping device 104 via the actuation assembly 200. Each operational element 290 may be a metal actuation wire or tether configured to impart a translational force which controls the operation of the grasping device 104. For example, the grasping device 104 may include distal jaws normally disposed in a closed position, such as by a spring or other biasing element, and the distal movement of the operational element 290 relative to the grasping device 104 may open the jaws. When the operational element 290 is retracted relative to the grasping device 104 the jaws may move back to the closed position, such as to grasp tissue.

In the illustrated embodiment, the device 100 includes an operational element 290 disposed through one of the actuation elements 208. However, it will be understood that the device 100 may have other configurations and assemblies. For example, the device 100 may not include an operational element 290 or an operational element 290 may be disposed through or alongside each of the actuation elements 208.

The actuation assembly 200 includes a body 202 configured to be grasped by a user. The proximal ends of the actuation elements 208 and the optional operational elements 290 may extend into or through the body 202. The actuation assembly 200 also includes a plurality of control actuators 230 operable to control the position, rotation, and operation of the grasping devices 104 via the actuation elements 208. Each of the actuation elements 208 and each of the operational elements 290 may be coupled with one or more control actuators 230 such that a user may control the position, rotation, and operation of the grasping devices via the control actuators 230. The control actuators 230 may be any suitable device by which a user may actuate to control the position and/or rotation of one of the actuation elements 208 or one of the operational elements 290. For example, the control actuators 230 may be push buttons, toggles, switches, levers, triggers, sliders, or the like.

In the illustrated embodiment, the actuation assembly 200 may include first or translational control actuators 230a operable to control the linear or translational position of one of the actuation elements 208, second or rotational control actuators 230b operable to control the rotational position of one of the actuation elements 208, and operational control actuators 230c operable to control the linear or translational position of one of the operational elements 290. For example, an operator may use the translational and rotational control actuators 230a, 230b to control the translational and rotational position of the grasping devices 104 via the actuation elements 208, such as to deploy the grasping devices 104 at the desired location. Optionally, an operator may also use the operational control actuators 230c to control the operation of the grasping devices 104 via the operational elements 290, such as to open and/or close the grasping devices 104 to grasp tissue.

In the illustrated embodiment, the actuation assembly 200 includes two translational control actuators 230a, two rotational control actuators 230b, and one operational control actuator 230c. However, the actuation assembly 200 may have other suitable configurations and assemblies. For example, the actuation assembly 200 may include any suitable number of translational control actuators 230a, rotational control actuators 230b, and operational control actuators 230c.

In the illustrated embodiment, each translational control actuator 230a is disposed near a proximal end of one of the actuation elements 208 proximally from the body 202 and each rotational control actuator 230b is disposed at the proximal end of one of the actuation elements 208 proximally from the translational control actuator 230a. Each translational control actuator 230a may be translationally fixed to the respective actuation element 208 such that translational movement of the translational control actuator 230a translates to translational movement of the actuation element 208. The actuation element 208 may be rotationally decoupled from the translational control actuator 230a such that the actuation element 208 may rotate independently from the translational control actuator 230a. The translational control actuator 230a may be depressed or otherwise moved toward the body 202, such as by a user, to distally extend the actuation element 208 and thereby position the grasping device 104.

The rotational control actuator 230b may be rotationally coupled with the respective actuation element 208 such that rotational movement of the rotational control actuator 230b translates to rotational movement of the actuation element 208. The rotational control actuator 230b may be rotated, such as by a user, to rotate the actuation element 208 and thereby rotate the grasping device 104. The rotational control actuator 230b may be rotated independently from the first control actuator 230a.

The operational control actuator 230c may be disposed on a proximal side of the body 202, such as proximally to the translational and rotational control actuators 230a, 230b. The operational control actuator 230c may be directly or indirectly coupled with the operational element 290 to operate the operational element 290 to actuate the grasping device 104. The operational control actuator 230c may be coupled with the operational element 290 such that depression or activation of the operational control actuator 230c translates the operational element 290 to actuate the respective grasping device 104, such as to open or close the grasping device 104. The operational control actuator 230c may be coupled with the operational element 290 via a biasing element such that the operational control actuator 230c returns to the unactuated position when a user releases the operational control actuator 230c, thereby retracting the operational element 290.

However, it will be understood that the actuation assembly 200 may have other suitable shapes, assemblies, and configurations. For example, the operational control actuator

230c may be disposed on a different side of the body 202 from the other control actuators 230a, 230b, one or more of the control actuators 230 may be disposed along the body 202, the translational control actuators 230a may not be aligned with the rotational control actuators 230b, and/or the translational and rotational control actuators 230a, 230b may be coupled to the respective grasping device 104 via separate actuation elements 208. Additionally, one or more of the translational control actuators 230a, rotational control actuators 230b, and operational control actuators 230c may be combined. For example, the translational and rotational control actuators 230a, 230b may be combined into a single control actuator 230 operable to control the translational and rotational position of the grasping device 104 via the actuation element 208.

In operation, the actuation assembly 200 may be operated, such as by a user, to control the tissue recruiting assembly 102, such as to recruit tissue with one or more grasping devices 104. The grasping devices 104 may be disposed through a distal end of an endoscope (not shown) and the catheter sheath assembly 300. The actuation assembly 200 may be operated by a user at a proximal end of the endoscope via the actuation elements 208 and/or operational elements 290 extending through a channel located within and extending through the endoscope. The endoscope and/or the grasping devices 104 may be inserted through the subject such that the grasping devices 104 are disposed in a desired position, such as above an identified defect. Each grasping device 104 may be moved via the respective translational control actuator 230a, rotated via the respective rotational control actuator 230b, and/or actuated by the respective operational control actuator 230c to grasp the tissue. For example, a user may control the position of the grasping device 104 by positioning the distal end of the endoscope and sliding or otherwise moving the translational control actuator 230a to extend and/or retract the actuation element 208. The user may control the rotation of the grasping device 104 by rotating the respective rotational control actuator 230b. Optionally, the user may also control the operation of the grasping device 104, such as the opening and closing of the grasping device 104, by engaging and disengaging the operational control actuator 230c. After the grasping devices 104 grasp the tissue, the actuation assembly 200 may be used to recruit the grasped tissue proximally, such as to close a defect or to appose two sides of a defect such that a hemostatic device may be used to close the defect, such as by proximally retracting the translational control actuators 230a.

Figure 5:
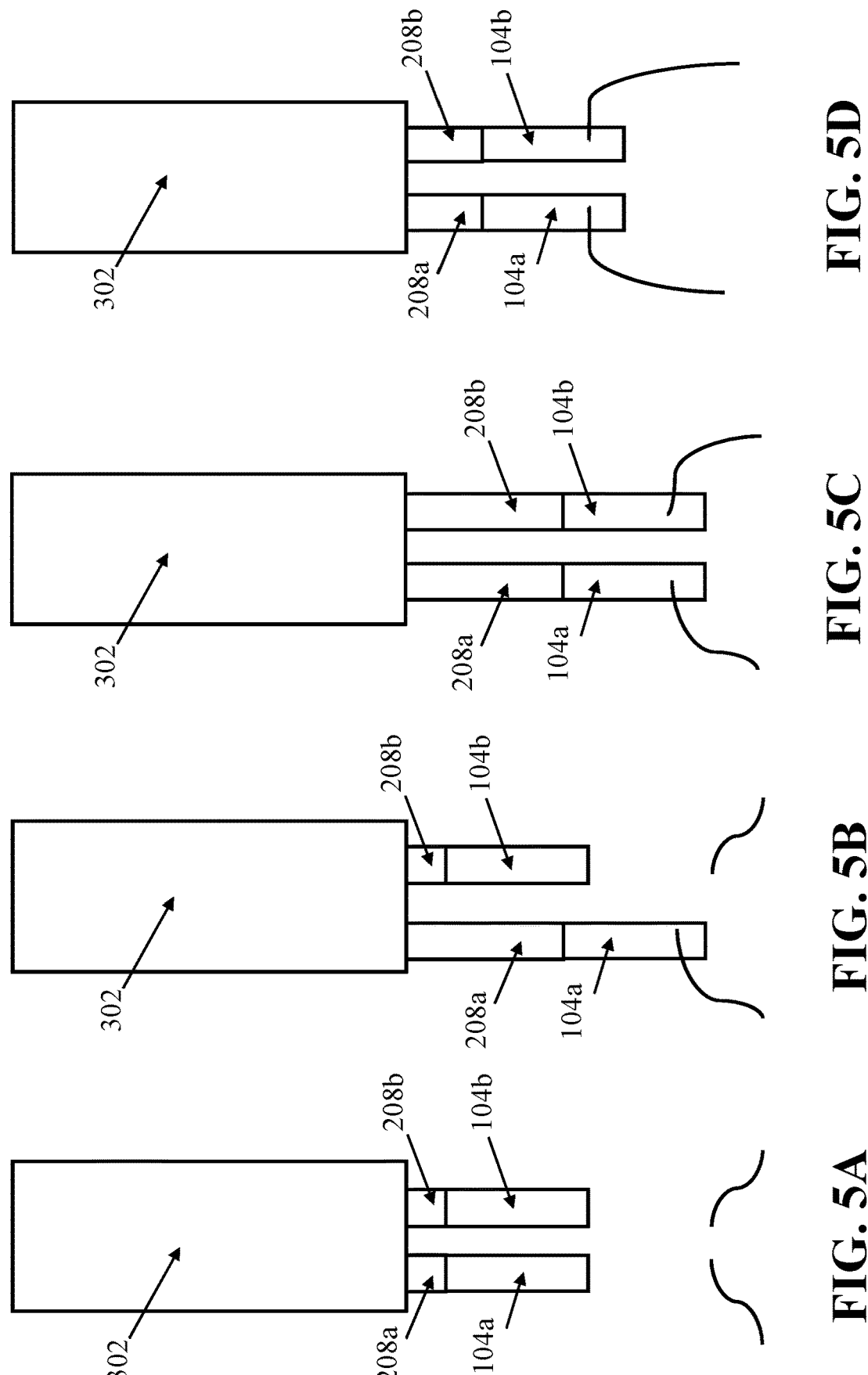
FIGS. 5A-5D are schematic illustrations of the tissue recruiting assembly of the tissue recruiting devices of FIGS. 1-2 recruiting tissue.

An exemplary method of operating the grasping devices 104 of the tissue recruiting assembly 102 is schematically illustrated in FIGS. 5A-5D. As shown in FIG. 5A, the tissue recruiting assembly 102 may be positioned above a defect, such as via the catheter sheath assembly 300 and the endoscope. The grasping devices 104 may be extended from the distal end of the catheter 302 via the actuation elements 208. In some embodiments, the defect is identified and visualized using one or more cameras (not shown) operably connected to the endoscope. In the illustrated embodiment, a first grasping device 104a is coupled with a first actuation element 208a and a second grasping device 104b is coupled with a second actuation element 208b.

As shown in FIG. 5B, one of the grasping devices 104 may be deployed to engage tissue on a first side of the defect. The endoscope, the catheter 302, and/or the actuation element 208 may be manipulated such that the first grasping device 104a is oriented to face the first side of the identified defect. The actuation element 208 coupled with the first grasping device 104a may be translated and rotated, such as via one of the translational control actuators 230a and one of the rotational control actuators 230b of the actuation assembly 200, such that the first grasping device 104a engages and grasps the tissue on the first side of the defect. While not illustrated, the first grasping device 104a may also be operated via an operational element 290, such as via one of the operational control actuators 230c of the actuation assembly 200, to grasp the tissue. The second grasping device 104b may remain relatively stationary relative to catheter 302 as the first grasping device 104a is deployed to grasp tissue.

As shown in FIG. 5C, the second grasping device 104b may be deployed to engage tissue on a second side of the defect. The endoscope, the catheter 302, and/or the second actuation element 208b may be manipulated such that the second grasping device 104b is oriented to face the second side of the identified defect. The second grasping device 104b may be independently controlled or operated from the first grasping device 104a to grasp tissue on the second side of the defect. The second actuation element 208b may be translated and rotated, such as via one of the translational control actuators 230a and one of the rotational control actuators 230b of the actuation assembly 200, such that the second grasping device 104b engages and grasps the tissue on the second side of the defect. The independent operation of the second grasping device 104b may permit the tissue recruiting device 100 to extend beyond the limits of standard recruiting devices to treat and close larger defects. For example, the flexibility of the device 100, such as the actuation elements 208, and the independent operation of the grasping devices 104 may permit the device 100 to treat and close larger defects than standard recruiting devices. While not illustrated, the second grasping device 104b may also be operated by an operational element 290, such as via one of the operational control actuators 230c of the actuation assembly 200, to grasp the tissue. The first grasping device 104a may remain deployed to grasp tissue on the first side of the defect as the second grasping device 104b is deployed to grasp tissue on the second side of the defect.

While the device 100 has been described as deploying two grasping devices 104a, 104b to grasp tissue, it will be understood that more than two grasping devices 104 may be deployed on multiple sides of the defect. For example, the device 100 may include more than two grasping devices 104 or more grasping device 104 may be loaded into the device 100 to be subsequently deployed after the first two grasping devices 104a, 104b are deployed to grasp tissue.

As shown in FIG. 5D, one or both grasping devices 104a, 104b may be retracted by proximally retracting the one or more respective actuation elements 208a, 208b to recruit the grasped tissue. For example, one or both of the translational control actuators 230a may be actuated to proximally retract the actuation elements 208a, 208b. The grasping devices 104a, 104b may continue to grasp the tissue as the grasping devices 104 are retracted. The retraction of one or both grasping devices 104a, 104b may substantially close the defect or appose the sides of the defect so that a hemostatic device may be deployed to close the defect. In some embodiments, the grasping devices 104a, 104b may be retracted into a locked position such that the grasping devices 104a, 104b are substantially fixed relative to the catheter 302.

Optionally, after the grasping devices 104a, 104b have been retracted to recruit the targeted tissue, a tissue closure mechanism, such as through the scope clip (TTS) or an over the scope clip (OTS), may be disposed around the recruited tissue to treat and/or substantially close the defect. The tissue closure mechanism may be deployed around the grasping devices 104a, 104b grasping tissue. For example, the tissue recruiting assembly 102 may be used with an over-the-scope (OTS) clip or a through-the-scope (TTS) clip to close the defect. In embodiments including an OTS clip, the grasping devices 104 may retract and recruit tissue into the OTS housing. In embodiments including a TTS clip, the grasping devices 104 may recruit the tissue into the distal end of the catheter 302. The OTS clip may be released (deployed) via the actuation assembly 200 or may be released via a separate controller.

In some embodiments, after the recruited tissue has been cinched or closed with a tissue closure mechanism, such as an OTS or TTS clip, the grasping devices 104 and/or the actuation elements 208 may be decoupled or otherwise disengaged from the tissue. For example, the operational element 290 may be actuated to open the grasping device 104 to release the tissue. The grasping devices 104 and/or the actuation elements 208 may be withdrawn or otherwise retracted from the closed defect.

Figure 6:
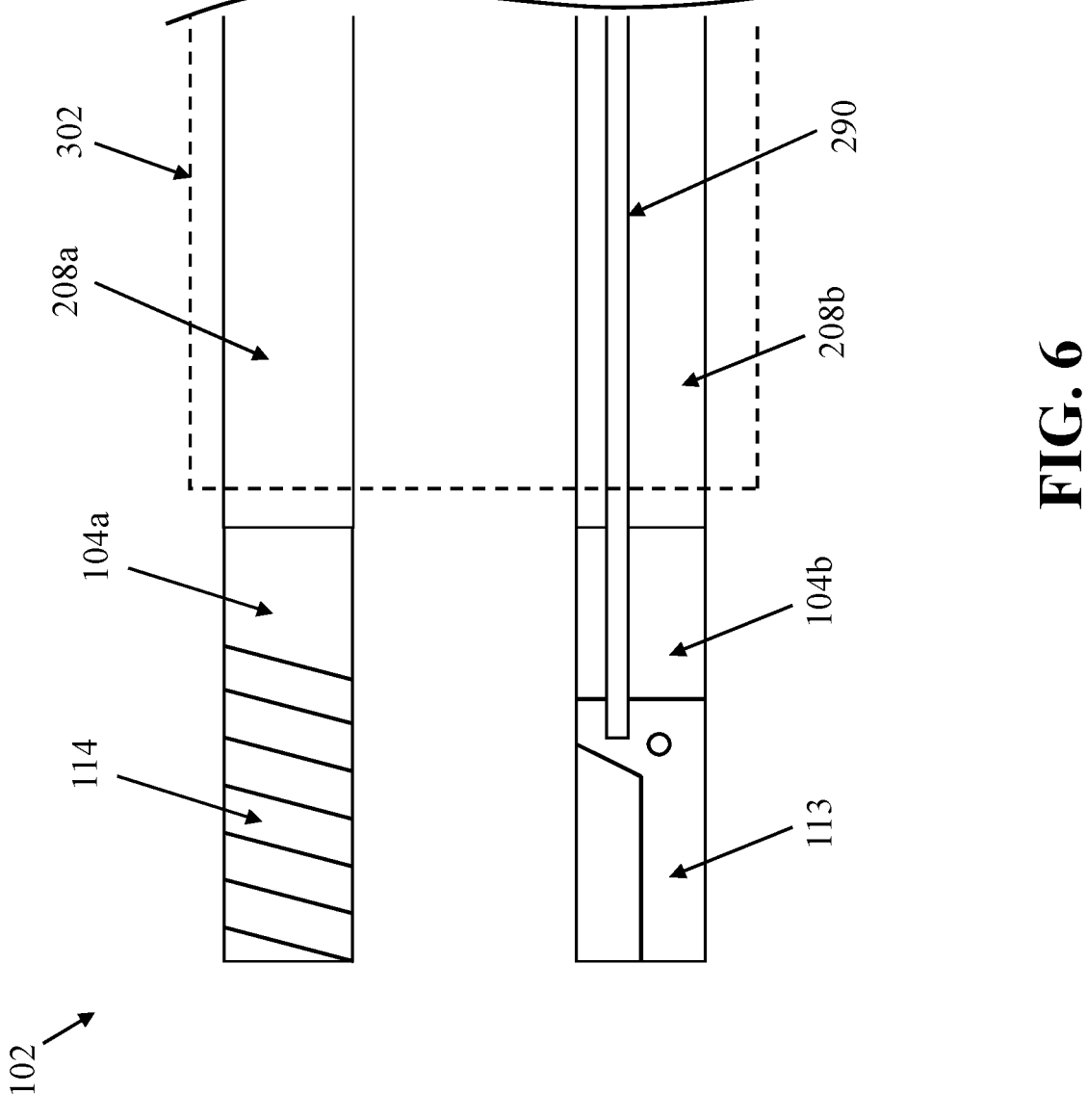
FIG. 6 is a schematic illustration of example grasping devices which may be used with a tissue recruiting device.

The grasping devices 104 may be end effectors capable of grasping target tissue, such as via one or more actuation elements 208 and/or one or more operational elements 290. As shown in FIG. 6, the tissue recruiting assembly 102 includes a first grasping device 104 having a plurality of helical coils 114 extending in a spiral or corkscrew manner and a second grasping device 104b having at least one movable jaw 113. The helical coils 114 of the first grasping device 104a may be configured to grasp tissue as the first grasping device 104a is spiraled or screwed into the tissue. The movable jaw 113 of the second grasping device 104b may be opened and closed to grasp tissue. The grasping devices 104a, 104b may be operated via the actuation assembly 200 of FIGS. 1-2.

The first grasping device 104a may be operated via a first actuation element 208a operable to translate and rotate the first grasping device 104a such that the first grasping device 104a grasps tissue. For example, the first actuation element 208a may translate and rotate the first grasping device 104a, such as via the actuation assembly 200, such that the first grasping device 104a spirals or screws into tissue such that the first grasping device 104a grasps the tissue.

The second grasping device 104b may be operated via a second actuation element 208b and an operational element 290. The second actuation element 208b may translate and rotate the second grasping device 104b, such as via the actuation assembly 200, such that the second grasping device 104b is properly positioned above target tissue. The operational element 290 may be distally extended, such as by actuation of the operational control actuator 230c, such that the second grasping device 104b grasps tissue, such as tissue on the other side of a defect from the first grasping device 104a. The distal extension of the operational element 290 may rotate the movable jaw 113 about a pivot such that the movable jaw 113 opens to grasp tissue. After the tissue is positioned between the movable jaw 113 and the remainder of the second grasping device 104b, the operational element 290 may be proximally retracted (e.g., the operational control actuator 230c may be retracted) such that the movable jaw 113 pivots closed with the tissue grasped between the movable jaw 113 and the remainder of the second grasping device 104b. Further, the grasping device 104 may have more than one movable jaw 113, such as two movable jaws 113 that rotate about a central pivot. In the illustrated schematic, the operational element 290 extends outside the actuation element 208. However, it will be understood that the operational element 290 may extend through the interior of the actuation element 208.

While the illustrated embodiment includes a first grasping device 104a with helical coils 114 operable by one actuation element 208a and a second grasping device 104b with a movable jaw 113 operable by an actuation element 208b and an operational element 290, it will be understood that the device 100 may have other assemblies and configurations.

Referring now to FIGS. 7-10, a grasping device 104 is shown according to one embodiment of the present disclosure. As shown, the grasping device 104 is generally cylindrical in shape. The grasping device 104 includes a proximal end 106 and a distal end 108 opposite the proximal end 106. The proximal end 106 of the grasping device 104 may be coupled, directly or indirectly, with the distal end of one of the actuation elements 208. The grasping device 104 may be coupled with the actuation element 208 such that the translational and rotational movement of the respective actuation element 208 substantially translates to translational and rotational movement of the grasping device 104.

The grasping device 104 includes a coupling portion 110 near the proximal end 106 and a grasping portion 112 near the distal end 108. The coupling portion 110 is configured to couple with the distal end of the actuation element 208, either directly or indirectly. The grasping portion 112 is configured to extend into and grasp tissue, such as tissue on a side of a defect and/or the center of the defect.

As shown, the grasping portion 112 is substantially helical (e.g., a corkscrew) with a plurality of helical windings or coils 114 extending in a substantially longitudinal direction along a length of the grasping device 104. The grasping device 104 may also include a tip 116 at or near the distal end 108 of the grasping device 104. The tip 116 may be configured to pierce, puncture, or otherwise be inserted into tissue. For example, the tip 116 may be pointed or sharpened to pierce the tissue. The helical coils 114 and tip 116 may permit the grasping device 104 to pierce and spiral into tissue, such as to secure the grasping device 104 in grasping engagement with the tissue. The helical configuration of the grasping portion 112 of the grasping device 104 may be more reliable than conventional graspers, such as graspers with jaws or arms that may be opened and closed to grasp tissue. For example, the helical coils 114 of the grasping portion 112 may enable the grasping device 104 to consistently recruit deeper layers of tissue when performing certain procedures while also minimizing the scaring or tearing of tissue.

The grasping portion 112 of the grasping device 104 may be sized, shaped, and configured to pierce, spiral into, and grasp tissue. The grasping portion 112 may have a length extending in a substantially longitudinal direction, such as in parallel with the distal end of the actuation element 208. The length of the grasping portion 112 may be between about 1 mm and about 10 mm, such as between about 1.5 mm and about 7 mm, such as between about 2 mm and about 6 mm. However, it will be understood that the length of the grasping portion 112 may be selected based upon the location the of the target tissue. For example, the length of the grasping portion 112 may be between about 2.5 mm and about 4.0 mm in length, such as between about 3.0 mm about 3.5 mm, when the grasping device 104 is used in locations such as the colon. The length of the grasping portion 112 may be between about 4.0 mm and about 7.5 mm, such as between about 5.0 mm and about 6.0 mm, when the grasping device 104 is used to reach deeper tissue layers, such as in locations in the stomach, such as to reach deeper than the submucosal layer. Further, the length of the grasping portion 112 may be selected based upon the use of the grasping device 104. For example, the length of the grasping portion 112 may be between about 4.0 mm and about 7.5 mm, such as between about 5.0 mm and about 6.0 mm, when the grasping device 104 is to be deployed in deeper tissue layers, such as tissue in the stomach, and may be between about 2.5 mm and about 4.0 mm in length, such as between about 3.0 mm about 3.5 mm, when the grasping device 104 is to be used to recruit tissue, such as tissue in the stomach.

In some embodiments, the helical coils 114 are laser cut into the distal end of the grasping device 104 to form the grasping portion 112. In other embodiments, the helical coils 114 are wound into a coil or spiral.

The grasping portion 112 may also be sized, shaped, and configured such that the grasping device 104 may be deployed through the catheter 302, such as the dual lumen catheter 302 of FIG. 3. The grasping portion 112 may have a width or diameter such that the grasping device 104 may be extended through the catheter 302, such as with space between the inner surface of the catheter 302 and the grasping portion 112. In some embodiments, the grasping portion 112 has a width or diameter between about 0.025 inches (0.6 mm) and about 0.050 inches (1.3 mm), such as about 0.045 inches (1.1 mm).

In operation, the grasping device 104 may be positioned above target tissue and the grasping device 104 may be translated distally and/or rotated such that the tip 116 pierces the target tissue and the distal end 108 of the grasping device 104 is disposed in the tissue. Once the distal end 108 of the grasping device 104 is inserted into the tissue, the grasping device 104 may be maneuvered, such as via the actuation assembly 200, such that grasping device 104 is secured further disposed in the tissue. For example, the grasping device 104 may be translated distally, such as via one of the first control actuators 230a, into the tissue and/or the grasping device 104 may be rotated, such as via one of the second control actuators 230b, such that one or more helical coils 114 are disposed in the tissue. The translational and rotational motion of the grasping device 104 may spiral the helical coils 114 into the target tissue. The helical coils 114 may be disposed approximately perpendicular to the longitudinal direction of the grasping device 104 such that securement of the tissue around the helical coils 114 prevents or otherwise restricts the grasping device 104 from being withdrawn from the tissue.

Figure 9:
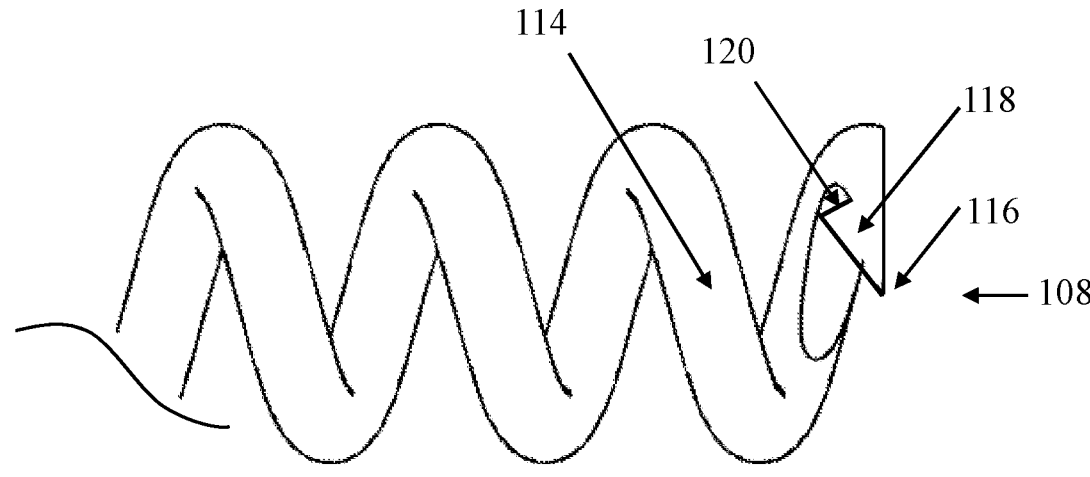

In some embodiments, as shown in FIG. 9, the grasping device 104 may include a barb 118 proximal to the tip 116. The barb 118 may be configured to prevent or otherwise restrict the tip 116 from withdrawing or otherwise backing out of the tissue once the tip 116 has been inserted into the tissue. For example, the barb 118 may be wider than the helical coils 114 such that tissue disposed around the helical coils 114 is substantially prevented from passing over the barb 118.

In some embodiments, the barb 118 includes an angled shoulder 120 configured to retain the tip 116 in the tissue. The angled shoulder 120 may be disposed at the proximal end of the barb 118 and may be substantially perpendicular to or disposed at a proximal angle to the adjacent portion of the helical coils 114. The angled shoulder 120 may be configured to abut tissue disposed around the helical coils 114 when the grasping portion 112 is at least partially inserted into tissue such that the abutment between the angled shoulder 120 and the tissue disposed around the helical coils 114 prevents or otherwise restricts the grasping device 104 from being withdrawn from tissue once the barb 118 is inserted in the tissue. In some embodiments, the barb 118, such as the angled shoulder 120, may include serrations. The serrations of the barb 118 may increase the grasp of the grasping device 104 on tissue.

The coupling portion 110 may be coupled directly or indirectly with the distal end of one of the actuation elements 208 such that the translational and rotational movement of the actuation element 208 may translate to translational and rotational movement of the grasping device 104. In some embodiments, the proximal end of the coupling portion 110 may be coupled directly to the distal end of the actuation element 208 such as via welding, adhesives, over-molding, crimping, swaging, or the like. In other embodiments, the coupling portion 110 is indirectly coupled to the distal end of the actuation element 208, such as via one or more couplers, as described below.

Figure 10:
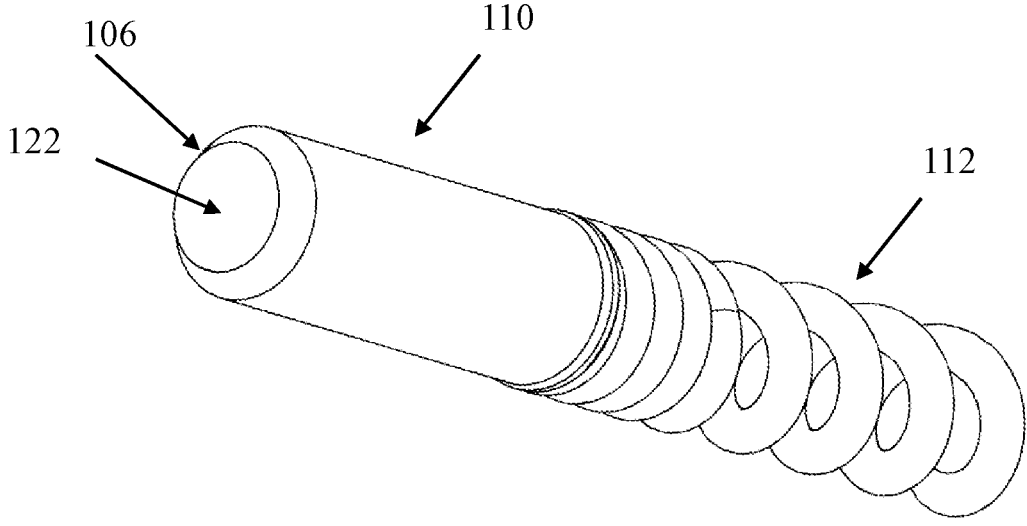

In some embodiments, as shown in FIG. 10, the coupling portion 110 includes a receiving portion 122 extending distally into the coupling portion 110 from the proximal end 106. In some embodiments, the receiving portion 122 is a substantially cylindrical bore. In some embodiments, the receiving portion 122 is sized, shaped, and configured to receive the distal end of one of the actuation elements 208. The distal end of the actuation element 208 may be inserted into the receiving portion 122 to couple the actuation element 208 with the grasping device 104. The grasping device 104 and the actuation element 208 may be further secured together via welding or adhesives. In other embodiments, the receiving portion 122 is configured to receive a coupler configured to operably couple the grasping device 104 to the actuation element 208, as described below.

Figure 7:
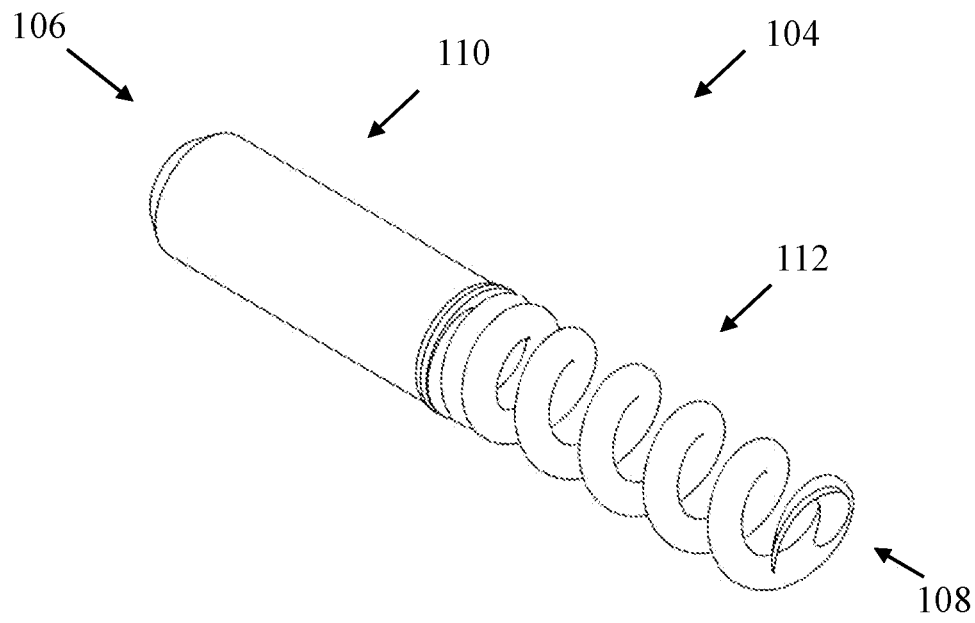
FIGS. 7-10 show various views of a grasping device according to one embodiment.
Figure 8:
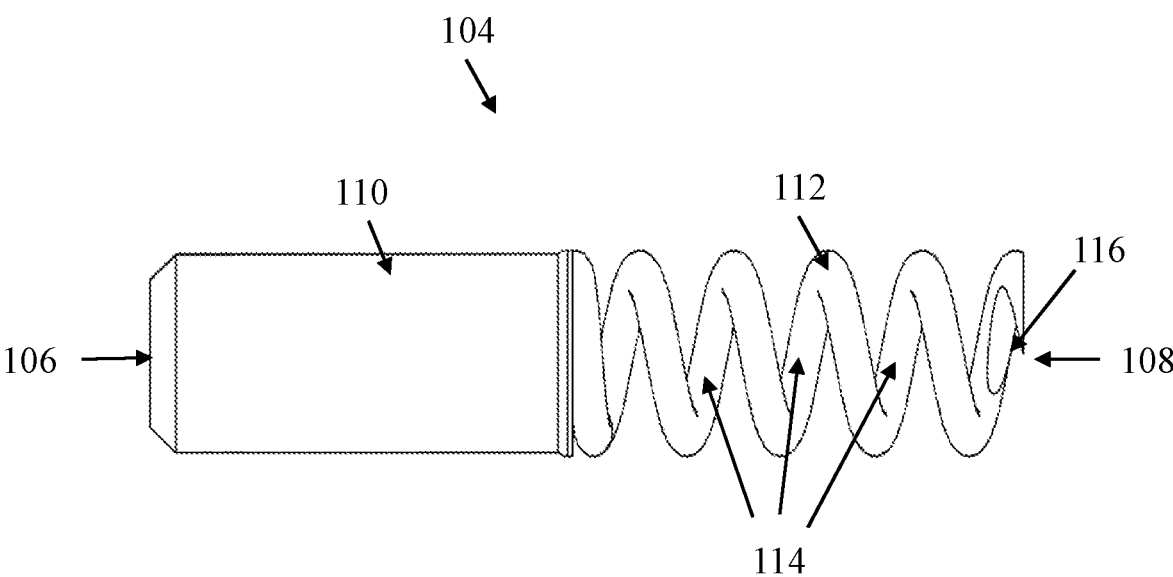

As shown in FIGS. 7-8 and 10, the proximal end 106 of the grasping device 104, such as the proximal end of the coupling portion 110, may be tapered. The tapered end of the grasping device 104 may assist the grasping device 104 in being retracted into the catheter 302. It will be understood that the tapering of the proximal end of the grasping device 104 also encompasses chamfering, fileting, rounding, or otherwise narrowing the proximal end of the grasping device 104 to assist in the retraction of the grasping device 104 into the catheter 302.

As shown in FIG. 11, an actuation assembly 200 according to one embodiment may be operable with two grasping devices 104 with helical coils 114 configured to be spiraled into tissue to grasp the tissue. In the illustrated embodiment, the actuation assembly 200 includes a first control actuator 230a coupled with a first actuation element 208a to control the operation of a first grasping device 104a. The actuation assembly 200 also includes a second control actuator 230b coupled with a second actuation element 208b to control the operation of a second grasping device 104b. The actuation elements 208a, 208b extend through a body 202 of the actuation assembly 200. The actuation assembly 200 is operable to independently control the deployment of the first and second grasping devices 104a, 104b. For example, the first control actuator 230a may be operable to translate and rotate the first actuation element 208a to control the first grasping device 104a and the second control actuator 230b may be operable to translate and rotate the second actuation element 208b to control the second grasping device 104b. While the actuation assembly 200 is illustrated as independently controlling two similar grasping devices 104, it will be understood that the actuation assembly 200 may be operable to different grasping devices 104 and the device 100 may include different first and second grasping devices 104a, 104b, such as any of the grasping devices 104 described below.

Figure 11A:
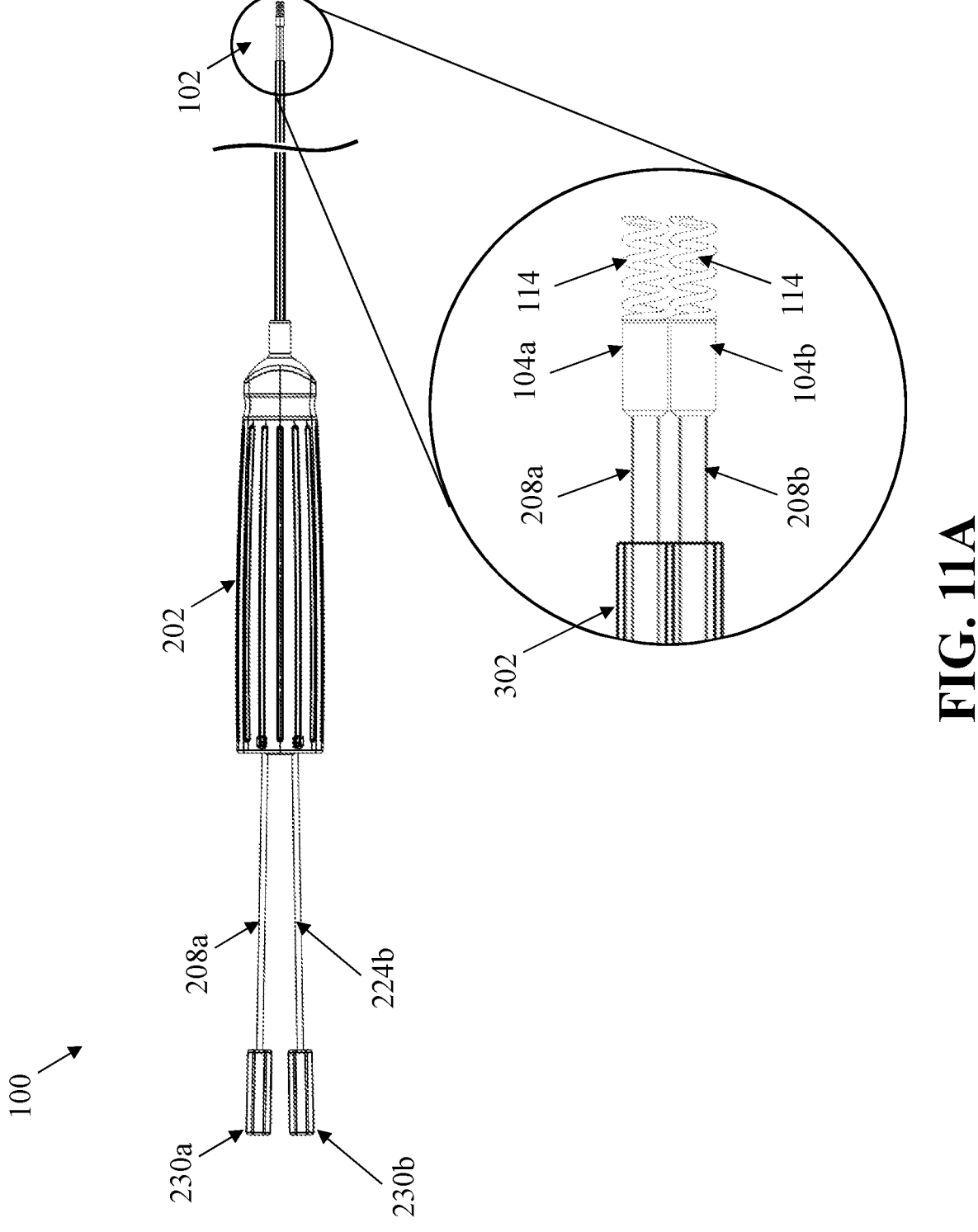
FIG. 11A is a top view of a tissue recruiting device including two of the grasping devices shown in FIGS. 7-10.
Figures 11B, 11C:
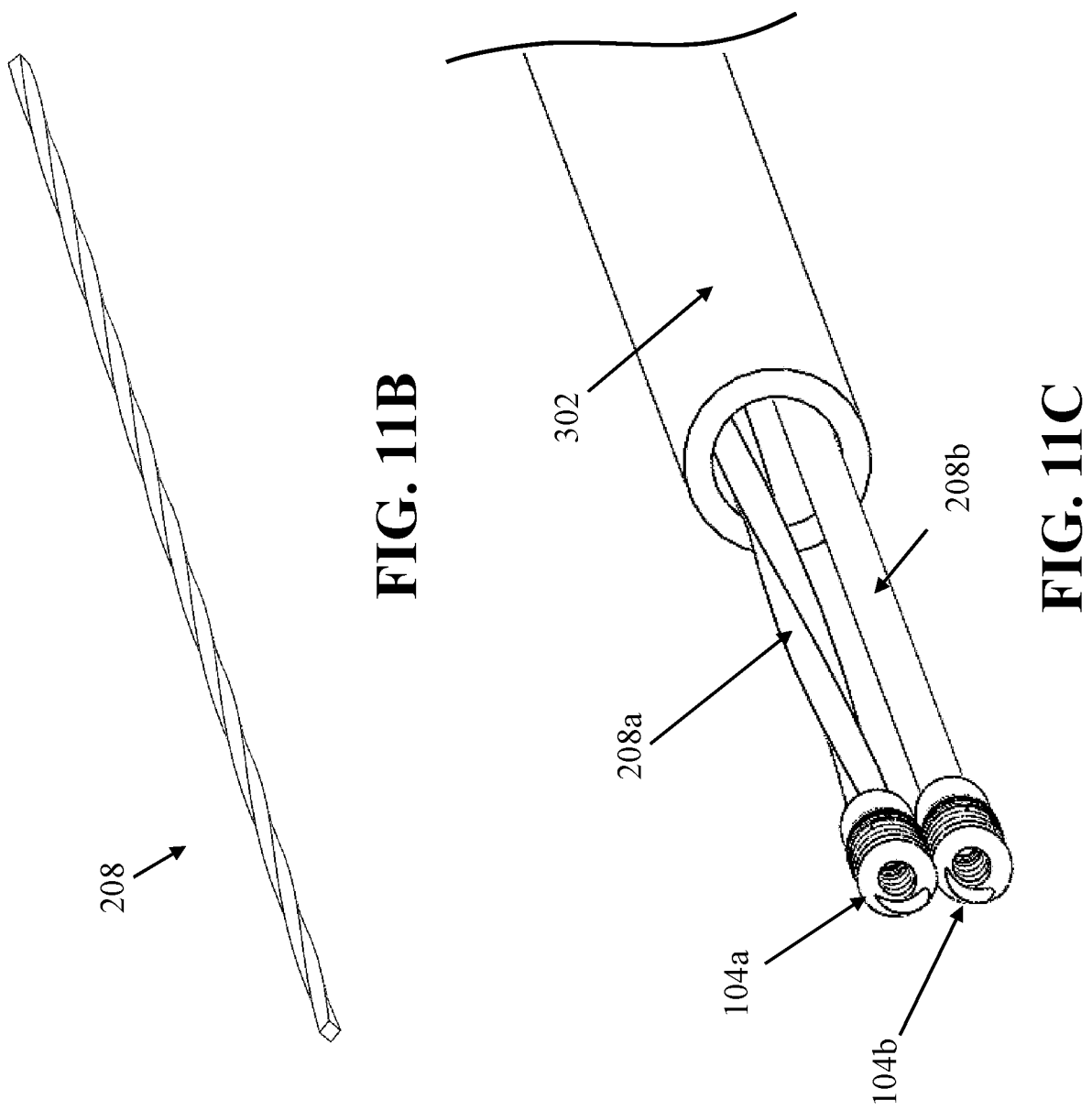
FIG. 11B is a perspective view of an actuation element according to one embodiment.
FIG. 11C is a perspective view of the distal end of a tissue recruiting device according to one embodiment with the actuation element of FIG. 11B.
Figures 11D, 11E:
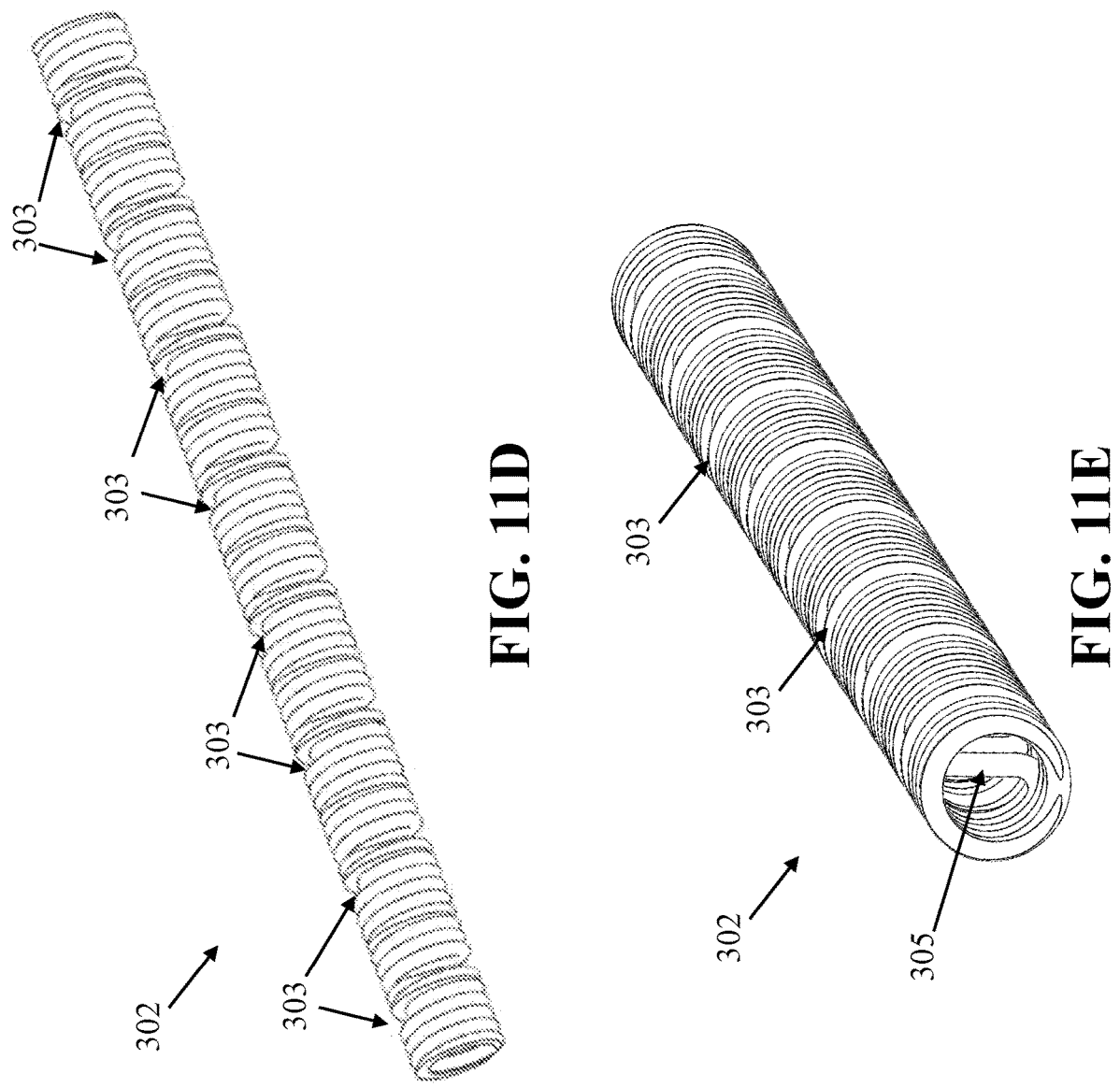
FIGS. 11D and 11E are perspective views of a catheter according to one embodiment.
Figure 11F:
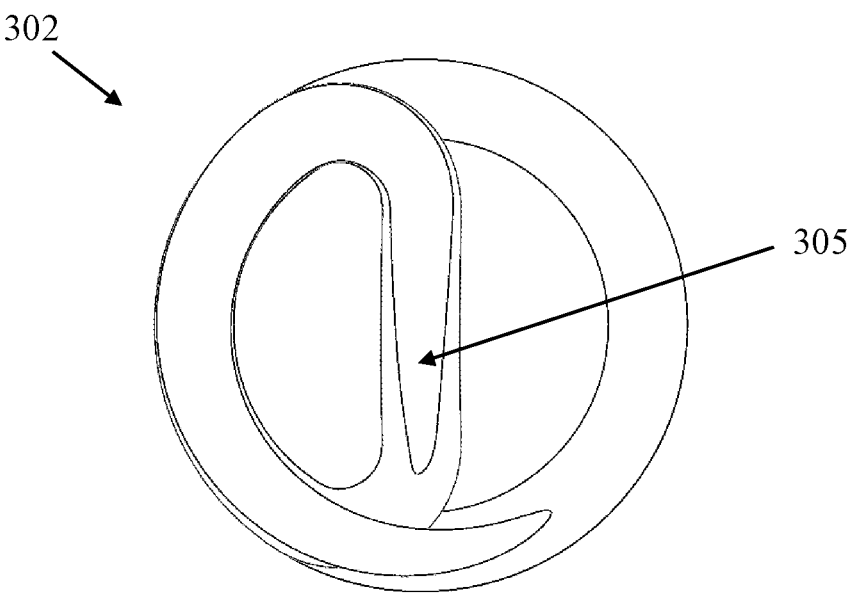
FIG. 11F is a front view of the catheter of FIGS. 11D-11E.
Figure 11G:
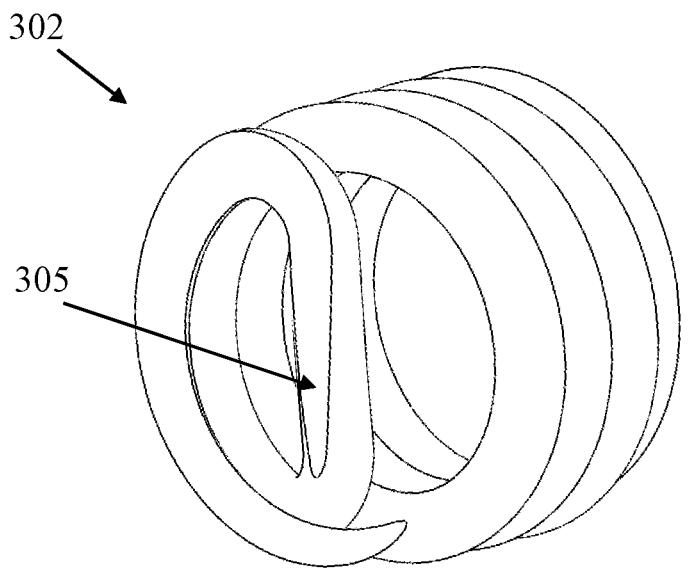
FIG. 11G is a perspective view of a distal portion of the catheter of FIGS. 11D-11E according to one embodiment.

In some embodiments, as shown in FIGS. 11B-11C, one or more actuation elements 208 may have a non-circular cross-section, such as to reduce friction between the actuation element 208 between the catheter 302 and/or the sheath 304. For example, the actuation elements 208 may have a cross-section which decreases the surface area of the actuation element 208 in contact with the catheter 302 and/or sheath 304, such as during operation of the device 100. In the illustrated embodiment, the actuation element 208 has a substantially rectangular cross-section that is twisted along a length of the actuation element. However, it will be understood that the actuation element 208 may have other shapes to decrease the friction between the catheter 302 and/or the sheath 304. For example, the actuation element 208 may be ovular, obround, elliptical, triangular, hexagonal, D-shaped, crescent-shaped, pie-shaped, grooved, tapered, or other suitable shape.

As shown in FIGS. 11B-11C, the actuation element 208 may also be twisted to further decrease the frictional contact between the actuation element 208 and the catheter 302 and/or the sheath 304. It will be understood that the twisting of the actuation element 208 also encompasses actuation elements 208 with helical or spiraled profiles. The twist of the actuation element 208 may also make it easier for a user to identify that the actuation element 208 is turning. Further, the twist of one of the actuation elements 208 may help a user identify which actuation element 208 is being operated. For example, as shown in FIG. 11C, a first actuation element 208a with a rectangular cross-section that is twisted along the length of the actuation element 208a is coupled with a first grasping device 104a and a second actuation element 208b with a substantially circular cross-section is coupled with a second actuation element 208b. The difference in shapes between the first and second actuation elements 208a, 208b may assist a user in identifying which actuation element 208a, 208b and which grasping device 104a, 104b is being operated, such as via the actuation assembly 200. In the illustrated embodiment, the first actuation element 208a has a rectangular cross-section that is twisted along the length of the actuation element 208 and the second actuation element 208b is substantially circular. However, it will be understood that both actuation elements 208 may have a rectangular cross-section that is twisted along the length of the actuation element 208.

In some embodiments, the catheter 302 may be configured to increase the compressive resistance of the catheter 302 during operation. As shown in FIGS. 11D-11G, the catheter 302 may be a spring sheath wound into a spiraled coil with a plurality of compressions 303 disposed along the length of the catheter 302. The compressions 303 may be formed by winding the coil into a narrower spiral at predetermined intervals along the length of the catheter 302.

The catheter 302 may also include a plurality of struts 305 extending across the cross-section of the catheter 302 at predetermined intervals. The struts 305 may be formed by bending the coil across the cross-section of the catheter 302 which may create the compressions 303. The struts 305 may provide radial support to the catheter 302 to act against compressive forces acting on the catheter 302 during operation. The struts 305 may also be substantially aligned such that the struts 305 separate the catheter 302, such as to prevent the actuation elements 208 from tangling during operation. The struts 305 may define pseudo-lumens extending through the catheter 302. In some embodiments, only the distal coil of the catheter 302 is bent to form a strut 305, such as to separate the actuation elements 208 at the distal end of the device 100 and prevent the actuation elements 208 from tangling during operation.

Figures 12A, 12B, 12C, 12D:
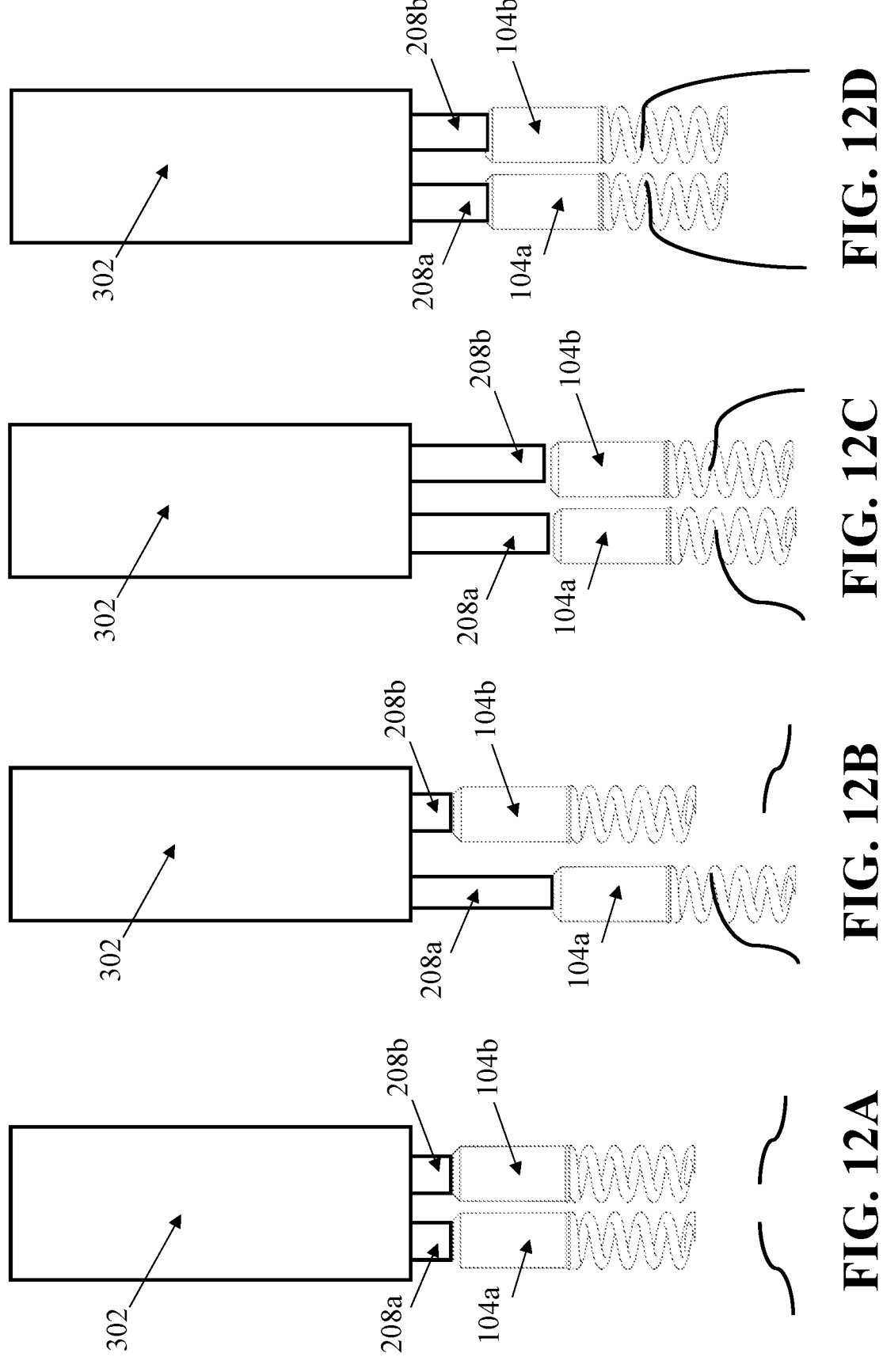
FIGS. 12A-12D are schematic illustrations showing an illustrative example of grasping and recruiting tissue using the grasping devices of FIGS. 7-10 with the tissue recruiting device of FIG. 11A.

As shown in FIGS. 12A-12D, two grasping devices 104 with helical coils 114 may be operated, such as via the actuation assembly 200 of FIG. 11, to grasp and recruit tissue. As shown in FIG. 12A, the endoscope and/or the catheter 302 may be oriented above an identified defect such that the first grasping device 104*a* and the second grasping device 104*b* are disposed substantially above the defect. As shown in FIG. 12B, the first grasping device 104*a* may be operated, such as via the first control actuator 230*a* of the actuation assembly 200, to grasp tissue on a first side of the defect. For example, the first actuation element 208*a* may be rotated and translated such that the first grasping device 104*a* pierces the tissue and spirals into the tissue to securely grasp the tissue.

As shown in FIG. 12C, the second grasping device 104*b* may be operated, such as via the second control actuator 230*b* actuation assembly 200, to grasp tissue on a second side of the defect. The endoscope and/or the catheter 302 may be manipulated such that the second grasping device 104*b* is in a position above the second side of the defect after the first grasping device 104*a* has been maneuvered to grasp tissue. The second actuation element 208*b* may be rotated and translated such that the second grasping device 104*b* pieces the tissue on the opposite side of the defect and spirals into the tissue to securely grasp the tissue.

As shown in FIG. 12D, the first and second actuation elements 208*a*, 208*b* may be proximally retracted toward the catheter 302. The actuation elements 208*a*, 208*b* may be proximally retracted, such as via the first and second control actuators 230*a*, 230*b* of the actuation assembly 200, such that the grasping devices 104*a*, 104*b* and grasped tissue are brought toward the catheter 302. Optionally, a hemostatic clip may be deployed around the tissue recruited by the first and second grasping devices 104*a*, 104*b*.

Referring now to FIGS. 13A-18B, the grasping device 104 may have a variety of shapes and configurations, such as depending upon the desired use and/or tissue of the grasping device 104. As shown in FIGS. 13A-14B, the grasping portion 112 of the grasping device 104 may include a proximal portion 124 at the proximal end of the grasping portion 112 and a distal portion 126 extending distally from the proximal portion 124. The distal portion 126 may be configured to be inserted into and retained in target tissue. The proximal portion 124 may be configured to increase the flexibility of the grasping device 104 as it is retracted into a shroud, as described below. The proximal portion 124 may also be configured to provide a visual indication to a user regarding the desired depth the grasping device 104 should be inserted into tissue. The proximal portion 124 may limit the depth that the grasping portion may be inserted into tissue. For example, the proximal portion 124 may be configured to prevent the grasping device 104 from being inserted into tissue past the distal portion 126. In some embodiments, the proximal portion 124 may be configured to increase the flexibility of the grasping device 104. In some embodiments, the distal portion 126 may also be configured to allow the grasping device 104 to flex or bend, such as when the grasping device 104 grasps tissue and a subsequent grasping device 104 is maneuvered.

Figure 13A:
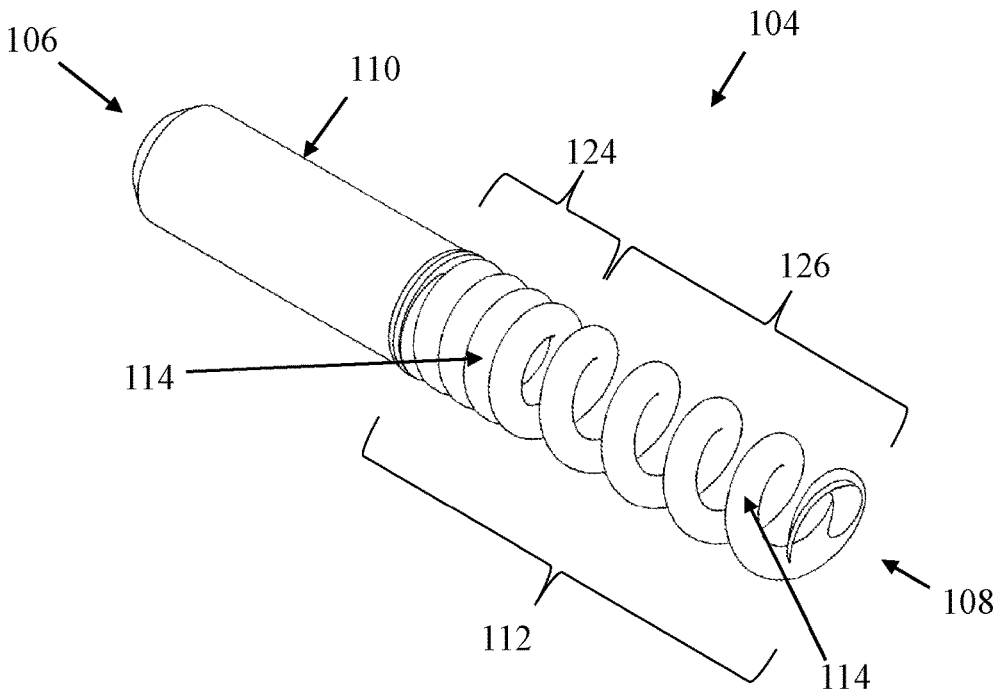
FIGS. 13A and 13B show various views of a grasping device according to another embodiment.
Figure 13B:
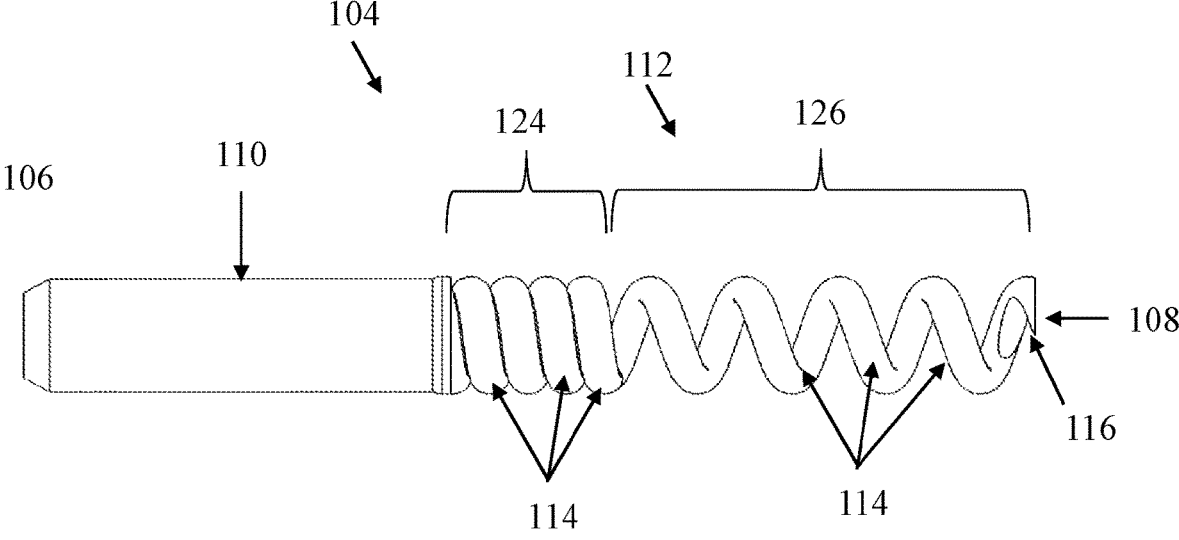

As shown in FIGS. 13A-13B, the pitch of the helical coils 114 of the proximal portion 124 may be lower than the pitch of the helical coils 114 in the distal portion 126 such that the helical coils 114 of the proximal portion 124 are closer together or more compact than the helical coils 114 of the distal portion 126. For example, the helical coils 114 of the proximal portion 124 may have a pitch and configuration such that each helical coil 114 abuts an adjacent helical coil 114 without gaps therebetween. The helical coils 114 of the distal portion 126 may have a pitch and configuration such that each helical coil 114 is spaced apart from an adjacent helical coil 114 with a gap therebetween. The different pitch of the helical coils 114 of the proximal portion 124 and the distal portion 126 may improve the flexibility of the grasping portion 112 as the grasping device 104 is retracted, such as toward a shroud. The helical coils 114 of the proximal and distal portions 124, 126 may also reduce bending stresses when the grasping devices 104 are retracted, such as to prevent the grasping portion 112 from pulling out of tissue. The difference in pitch of the helical coils 114 of the proximal portion 124 and the distal portion 126 may also provide a visual indication and/or operate as a physical stop so that tissue does not continue past the distal portion 126 when the grasping portion 112 is inserted into tissue.

Figure 14A:
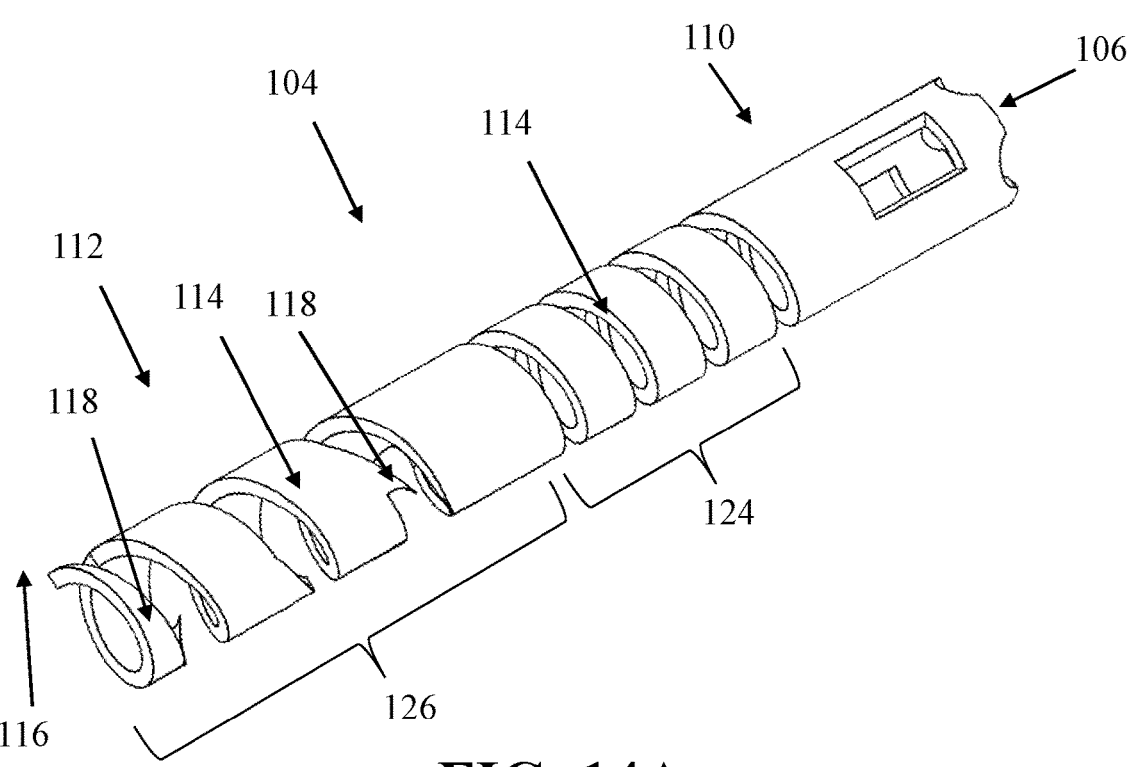
FIGS. 14A and 14B are front and rear perspective views of a grasping device according to another embodiment.
Figure 14B:
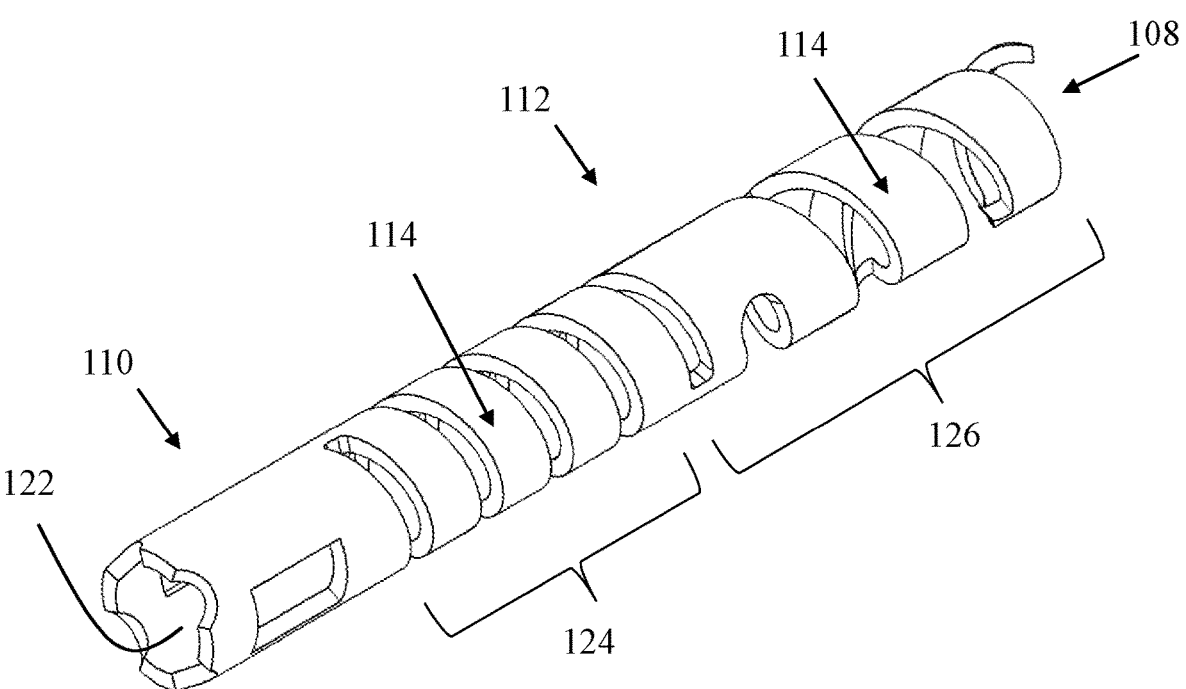

As shown in FIGS. 14A-14B, the helical coils 114 of the proximal portion 124 may be narrower than the helical coils 114 in the distal portion 126. The thicker helical coils 114 of the distal portion 126 may grasp the target tissue more securely. The narrower helical coils 114 of the proximal portion 124 may increase the flexibility of the grasping device 104 and/or reduce the stress and strain exerted on the device 100, such as when the grasping device 104 is proximally retracted via the actuation element 208 to recruit the grasped tissue. In some embodiments, the helical coils 114 of the distal portion 126 may include one or more barbs 118 disposed proximally from the tip 116. The distal barbs 118 may further secure the tissue after the grasping device 104 is inserted into the tissue. For example, barbs 118 may be included on the distal side of one or more of the helical coils 114 to further secure the grasping device 104 in tissue when the helical coils 114 of the distal portion 126 are inserted into the tissue. The barbs 118 may be disposed at varying points around the circumference of the helical coils 114.

In some embodiments, the grasping device 104 may include a stop or other component at the transition between the distal portion 126 and the proximal portion 124 to prevent or otherwise restrict tissue from engaging with the proximal portion 124. For example, the grasping device 104 may include a flange or shoulder substantially perpendicular to the helical coils 114 at the transition between the distal portion 126 and the proximal portion 124 configured to abut tissue when the distal portion 126 is inserted into the tissue. Additionally or alternatively, the grasping device 104 may include a weld between the proximal and distal portions 124, 126 that disrupts the coiling path of the helical coils 114 such that tissue is substantially prevented from advancing to the proximal portion 124.

Figure 15A:
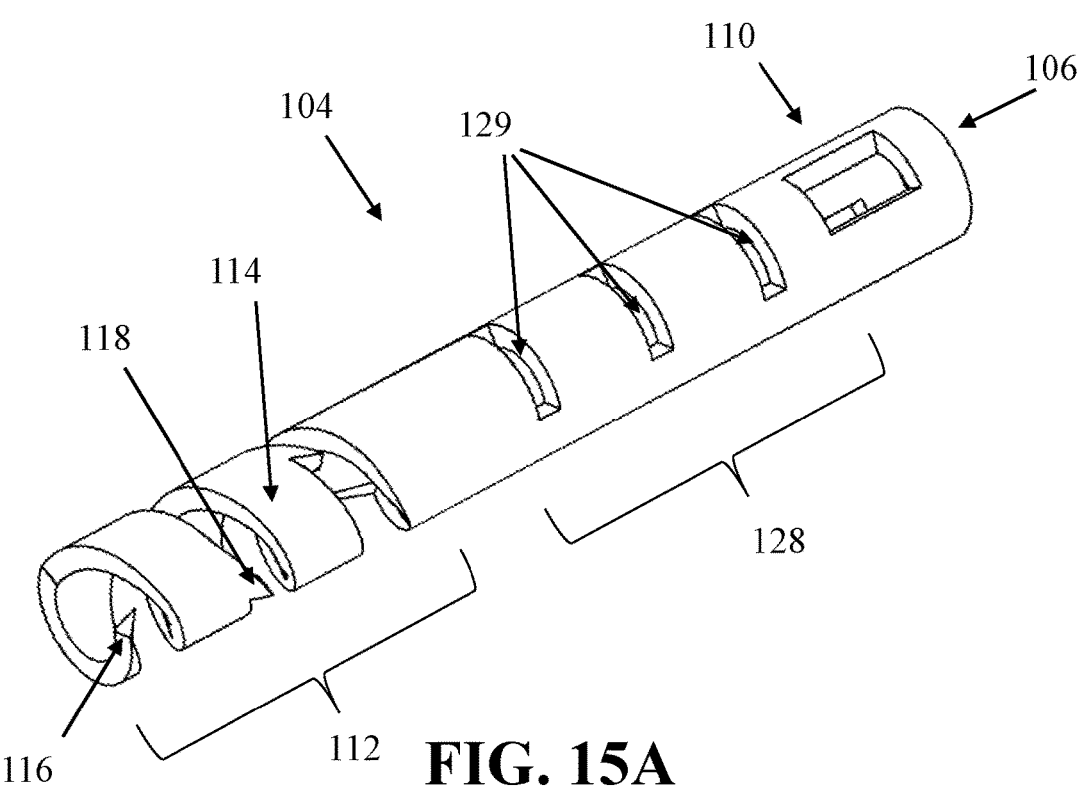
FIGS. 15A and 15B are front and rear perspective views of a grasping device according to another embodiment.
Figure 15B:
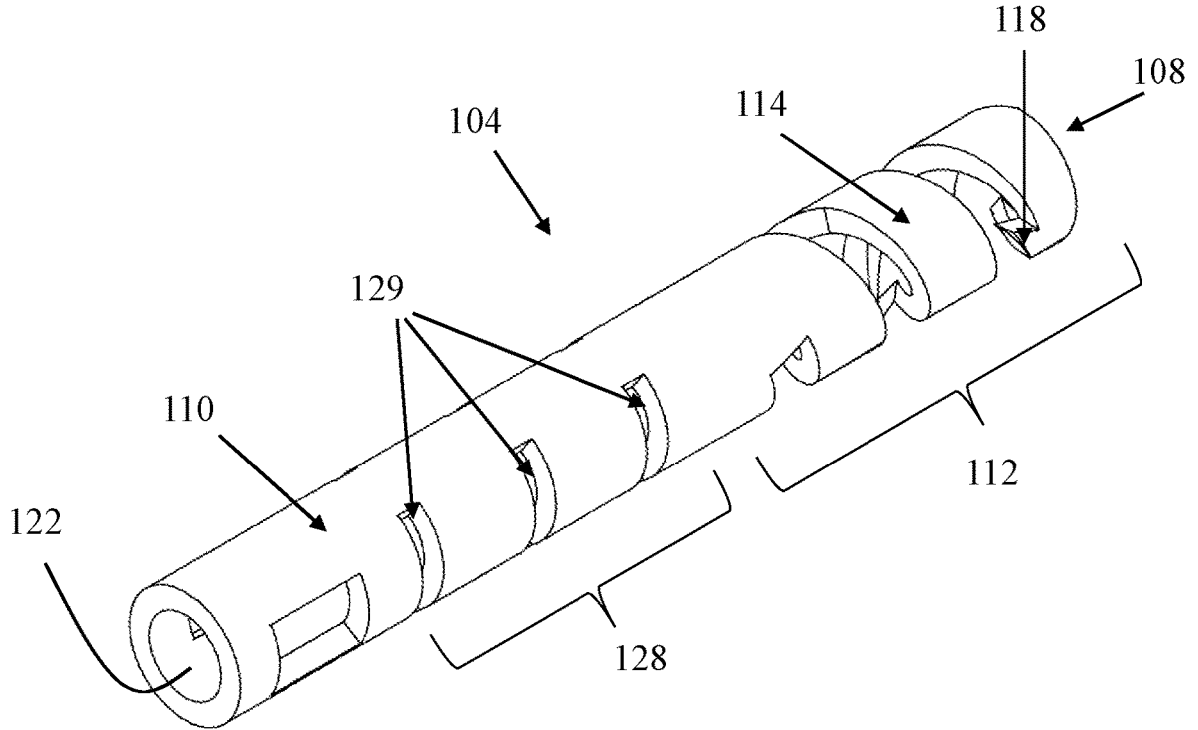

Referring now to FIGS. 15A-15B, in some embodiments, the grasping device 104 may include a flexible region or portion 128 configured to permit the grasping device 104 to flex or otherwise bend, such as when the grasping portion 112 of the grasping device 104 is secured in tissue or during operation of a subsequently manipulated grasping device 104. The flexible portion 128 may be spaced from the distal end of the grasping device 104 a preset distance, such as at a medial portion of the grasping device 104. For example, the flexible portion 128 may be spaced from the distal end of the grasping device 104 such that the flexible portion 128 is disposed proximally to the tissue when the grasping device 104 is deployed in tissue.

The flexible portion 128 may be sized, shaped, and configured to assist in deploying the grasping device 104 or another grasping device 104. For example, the grasping device 104 may flex at the flexible portion 128 to assist in inserting the grasping portion 112 into tissue via rotation and translation of the actuation element 208, such as when the grasping portion 112 is inserted into tissue at an angle different from the longitudinal axis of the distal end of the actuation element 208. The flexible portion 128 may also be stiff enough such that the grasping device 104 may be positioned and controlled to grasp target tissue. The flexible portion 128 may also be sized, shaped, and configured to assist in deploying a second grasping device 104 after the first grasping device 104 has been secured in tissue. For example, after the grasping portion 112 of the first grasping device 104 is secured in tissue, the flexible portion 128 may permit the coupling portion 110 of the first grasping device 104 to flex such that the device 100 may be operated to position and deploy the second grasping device 104.

In the illustrated embodiment, the flexible portion 128 includes a plurality of slots 129 laterally extending through the body of the grasping device 104. The slots 129 may permit the flexible portion 128 to bend or flex around the slots 129. Additionally or alternatively, the flexible portion 128 may comprise thinner helical coils 114, larger spaces between the helical coils 114, closed pitches between the helical coils 114, reduced material (e.g., the inclusion of apertures) and/or a more flexible material, or combinations thereof, such that the flexible portion 128 may flex or otherwise bend. The flexible portion 128 of the grasping device 104 may improve tissue approximation. For example, the flexible portion 128 may make it easier to manipulate the grasping devices 104, such as after the distal end of the grasping device 104 has been deployed in tissue, such as to engage an additional grasping device 104 with the tissue. The flexible portion 128 may also reduce the forces applied to the tissue as a subsequent grasping device 104 is deployed, such as to reduce the likelihood that the initially inserted grasping device 104 is pulled out of the tissue.

The actuation elements 208 may also be flexible enough such that the actuation elements 208 and the tissue recruiting assembly 102 may be extended to the desired location in a body, such as through the endoscope, and such that the endoscope may be maneuvered with the actuation elements 208 extending therethrough. The actuation elements 208 may also be stiff enough such that the actuation elements 208 may be operated to grasp tissue, such as described below. In some embodiments, the actuation elements 208 are solid core Nitinol wires with a diameter between about 0.018 inches (0.46 mm) and about 0.030 inches (0.76 mm), such as about 0.024 inches (0.61 mm). In some embodiments the actuation elements 208 provide one-to-one torque response over an endoscopic length, such that the distal end of the actuation element 208 rotates equivalently to rotation of the proximal end of the actuation element 208.

Figures 16A, 16B:
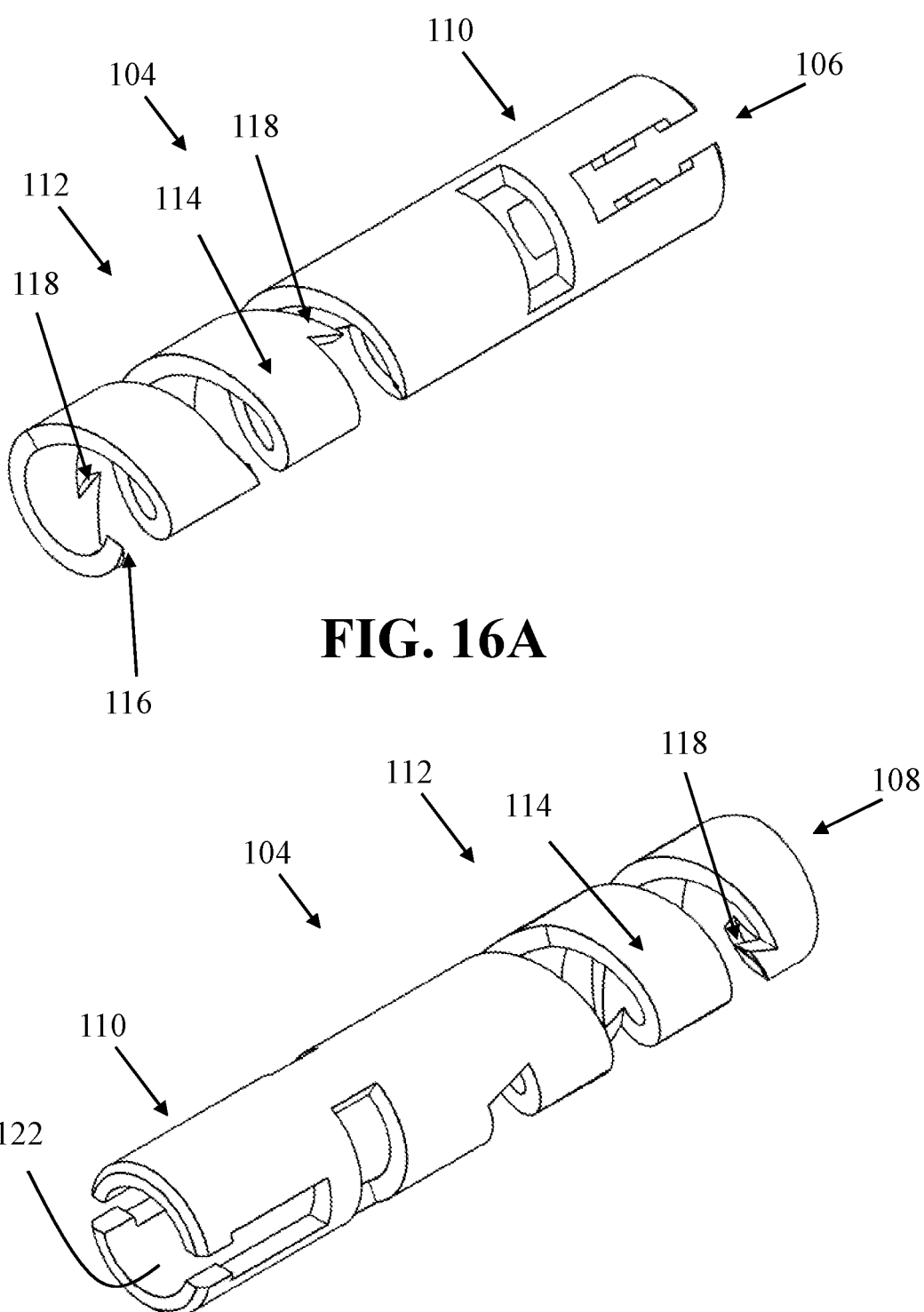
FIGS. 16A and 16B are front and rear perspective views of a grasping device according to another embodiment.
Figure 17A:
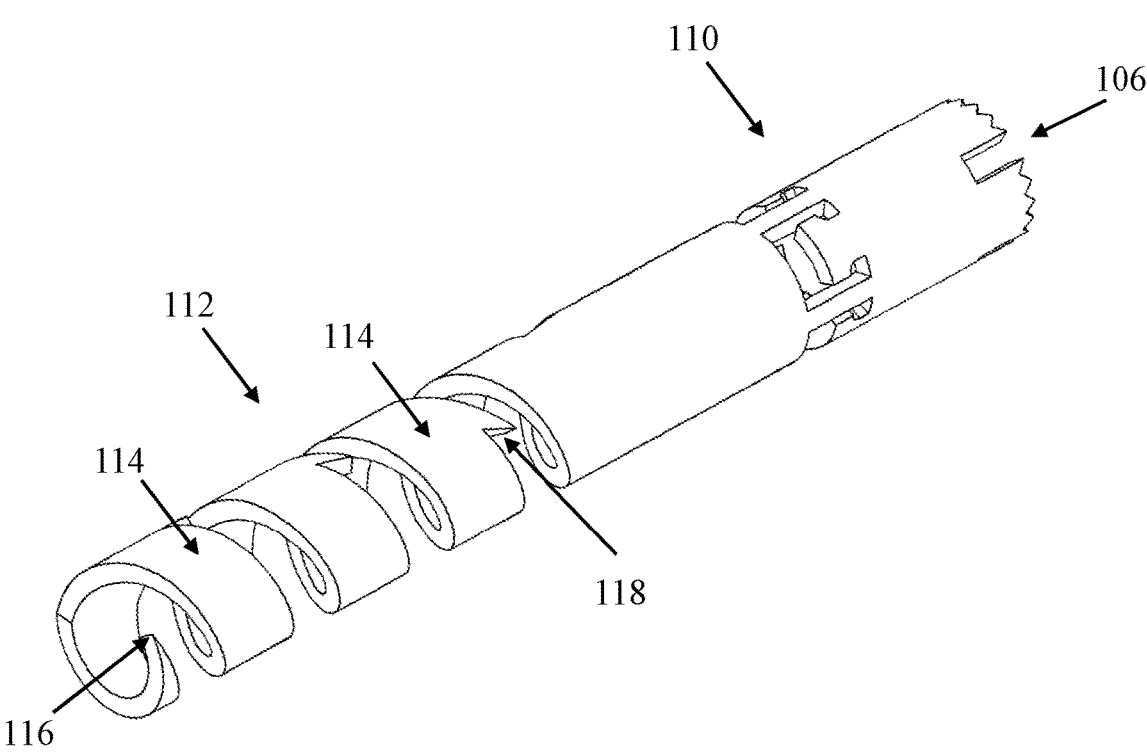
FIGS. 17A and 17B are front and rear perspective views of a grasping device according to another embodiment.
Figure 17B:
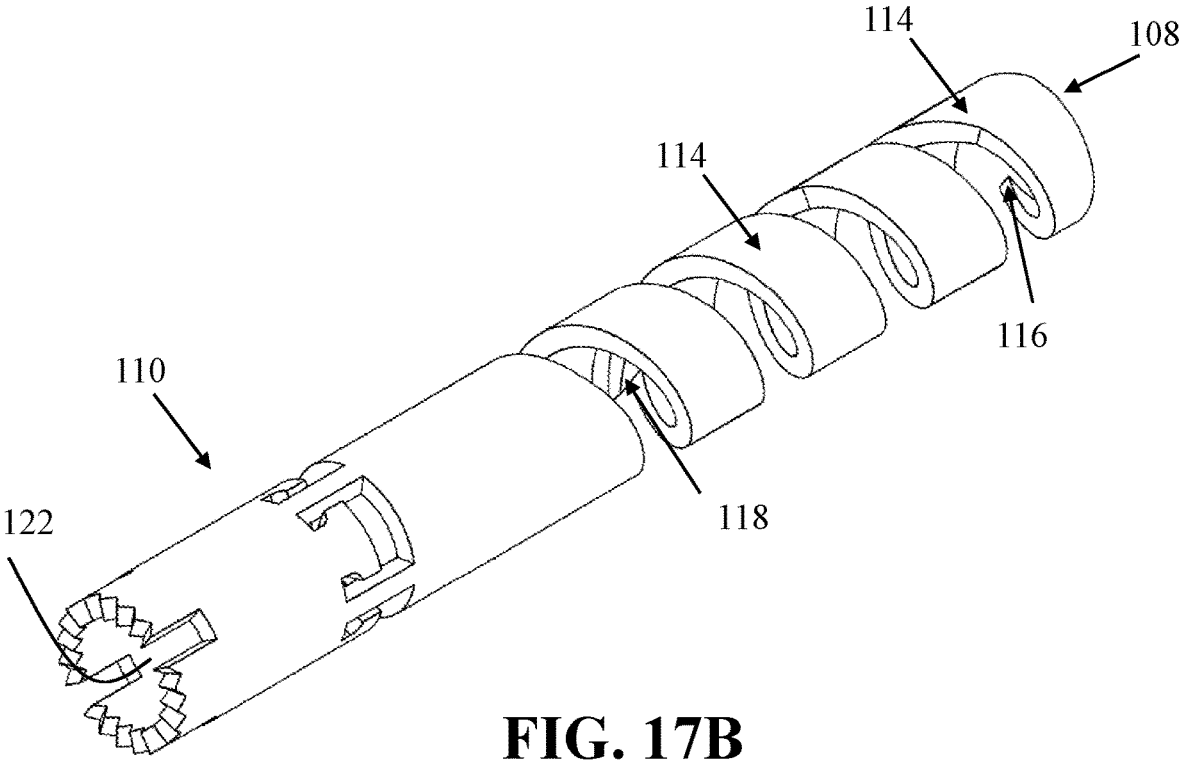

As shown in FIGS. 16A-17B, the coupling portion 110 and the grasping portion 112 may have a variety of sizes, shapes, and configurations, such as based on the tissue to be grasped and the other components of the device 100. As shown in FIGS. 16A-16B, the grasping portion 112 may be shorter and include two helical coils 114. As shown in FIGS. 17A-17B, the grasping portion 112 may be longer and include three helical coils 114. The grasping portion 112 may also include more than three helical coils 114. Additionally, as shown in FIGS. 16A-17B, the coupling portion 110 may include a variety of configurations, such as including tabs, slots, teeth, or apertures. For example, the coupling portion 110 of the grasping device 104 may be sized, shaped, and configured based upon the coupling of the grasping device 104 with the actuation element 208, as described below. As shown in FIG. 17B, the coupling portion 110 may include a plurality of serrations which may be operable to couple the grasping device 104 to the distal end of the actuation element 208, such as described below.

Figure 18A:
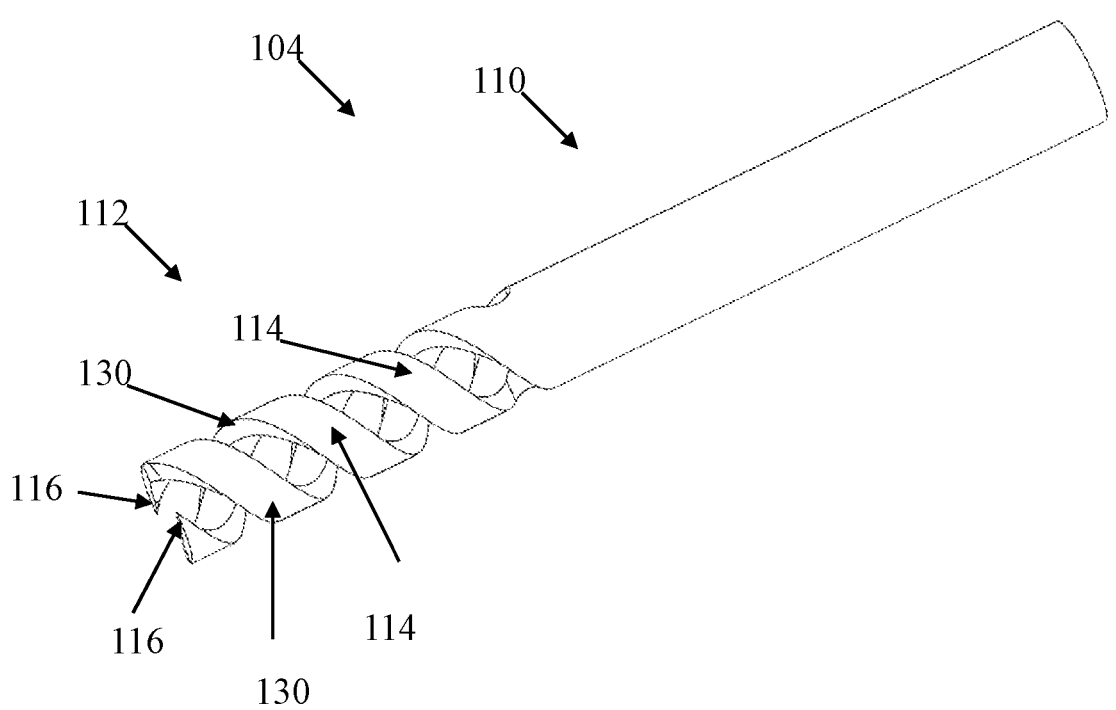
FIGS. 18A and 18B show various views of a grasping device with two flutes.
Figure 18B:
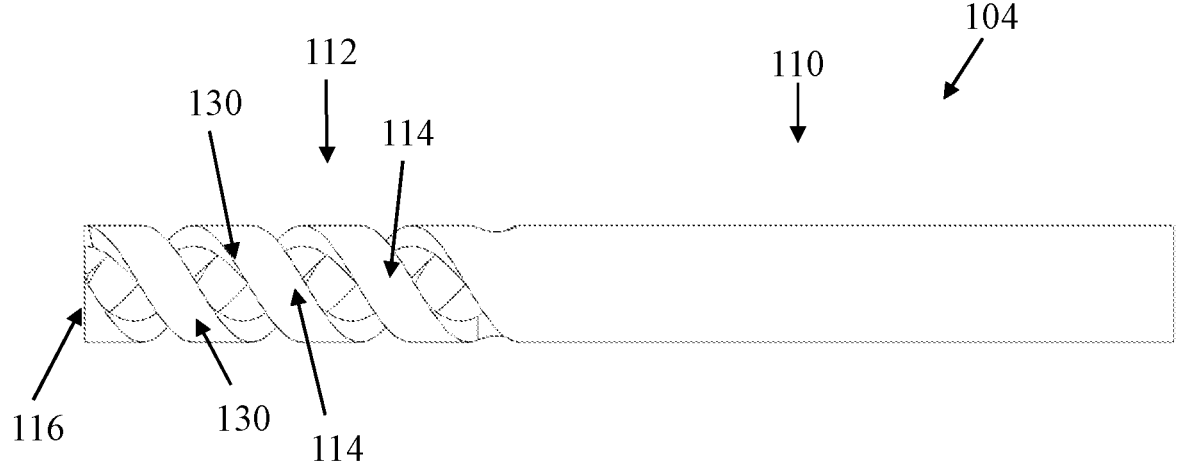

As shown in FIGS. 18A-18B, the grasping device 104 may comprise two flutes 130 disposed opposite each other. Each flute 130 may include helical coils 114 extending toward the distal end of the grasping device 104 and extending to a tip 116. The tips 116 of the flutes 130 may be disposed equidistant from the grasping portion 112 of the grasping device 104 such that the tips 116 of each flute 130 may simultaneously engage tissue. In some embodiments, each flute 130 may include a barb 118 with an angled shoulder 120, such as described above in reference to FIG. 9. The inclusion of two flutes 130 with helical coils 114 may increase tissue engagement when the grasping device 104 is deployed in tissue. Additionally, any of the other grasping devices 104 with helical coils 114 described above, such as the grasping devices 104 of FIGS. 7-10 and 13A-17B, may be configured to include two flutes 130.

The one or more grasping devices 104 may be operably coupled to the respective actuation element 208 such that the grasping device 104 may be decoupled from the actuation element 208, such as after the grasping device 104 has been deployed to grasp target tissue. For example, the grasping device 104 may be operably coupled with the actuation element 208 such that the actuation element 208 may translate and rotate the grasping device 104, such as via the actuation assembly 200, during operation and to decouple the grasping device 104 from the actuation element 208 after the grasping device 104 is deployed in the target tissue, such as to close the defect. The actuation element 208 may be initially coupled with the grasping device 104 to control the operation of the grasping device 104 to grasp tissue. After the grasping device 104 has been deployed or otherwise actuated to grasp tissue, the grasping device 104 may be decoupled from the actuation element 208, such as with the grasping device 104 grasping the tissue. The actuation element 208 may then be retracted from the deployed or actuated grasping device 104.

Referring now to FIGS. 19A-20D, in some embodiments, the tissue recruiting assembly 102 includes one or more shrouds 170. The shrouds 170 may configured to substantially cover the grasping devices 104 when the grasping devices 104 are in an undeployed or retracted state. The one or more shrouds 170 may be coupled directly or indirectly to the distal end of the catheter 302 (not shown). The one or more shrouds 170 may be configured to protect the endoscope and/or the grasping devices 104 during operation. The one or more shrouds 170 may comprise any suitable material for protecting the endoscope, the grasping devices 104, and/or maintaining recruited tissue therein. In some embodiments, the one or more shrouds 170 comprise polymer. Additionally or alternatively, the shroud 170 may comprise metal, polymer, a flexible metal, PEEK, Polyimide, Polyamide, a thermoplastic material, HDPE, PTFE, heat shrink, RNF, Polyolefin, or a compressive spring, or combinations thereof, or be an extension of the catheter 302. Further, it will be understood that the shroud 170 may be an over sheath and/or extend an entire length of the device 100, such as along an entire length of the catheter 302.

Figure 19A:
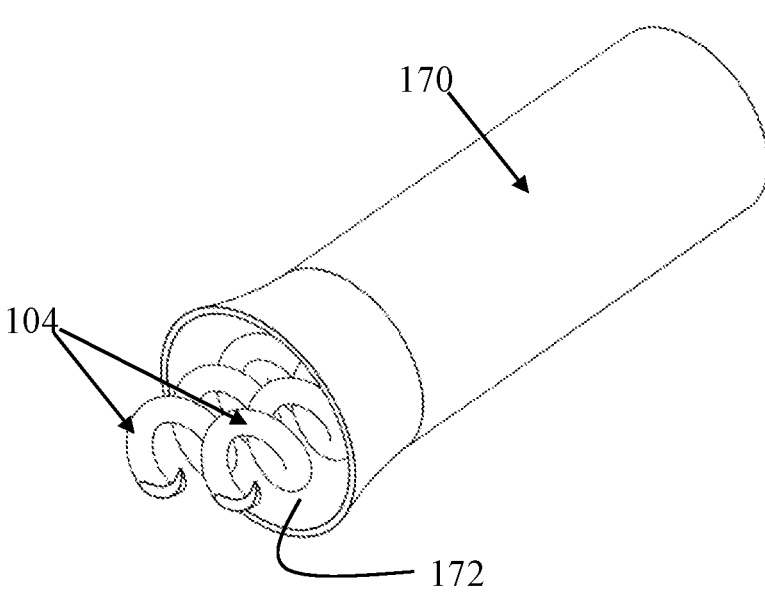
FIGS. 19A and 19B are perspective views of grasping devices retracted into and extended from a shroud according to one embodiment.
Figure 19B:
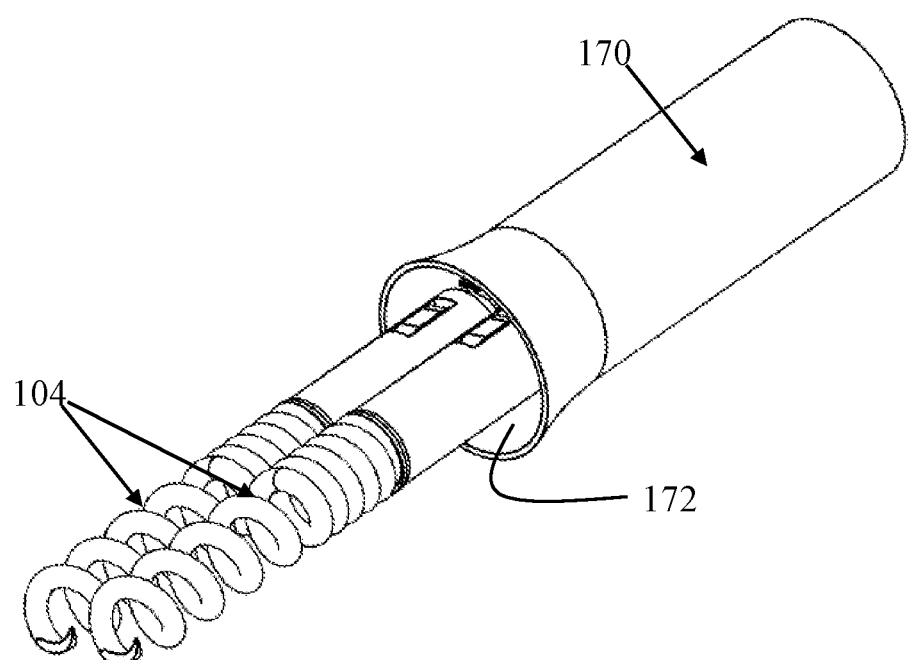

The one or more shrouds 170 may be substantially hollow cylinders defining a tissue recruitment area 172 configured to receive one or more grasping devices 104 and tissue recruited by the grasping devices 104, such as to maintain the tissue in a recruited position to close the defect after the grasping devices 104 have been decoupled from the actuation elements 208, as described below. The tissue recruitment area 172 may have a length in the longitudinal direction configured to substantially encase or surround the grasping devices 104 when the grasping devices 104 are in the undeployed state or retracted state, such as a fully retracted state, such that the grasping devices 104 are substantially disposed in the tissue recruitment area 172 (FIG. 19A). The grasping devices 104 may be distally extended from the shroud 170 (FIGS. 19B and 20A), such as to grasp tissue. In some embodiments, the distal end of each shroud 170 is flared radially outwardly to facilitate the deployment and retraction of the grasping devices 104. In other embodiments, the distal end of the shroud 170 is tapered or spear cut.

A proximal end of each shroud 170 may be coupled directly to the distal end of one of the catheters 302 or indirectly to the distal end of the catheter 302, such as via a connector, as described below. In the illustrated embodiment, the tissue recruiting assembly 102 includes one shroud 170 configured to encase both grasping devices 104. However, it will be understood that the tissue recruiting assembly 102 may have other configurations. For example, the catheter sheath assembly 300 may include two catheters 302 and the tissue recruiting assembly 102 may include a separate shroud 170 for covering each grasping device 104.

The tissue recruitment area 172 may have an inner diameter larger than the outer diameter of the one or more grasping devices 104 housed within the shroud 170 such that the one or more grasping devices 104 may move relatively freely within the tissue recruitment area 172, such as being extended and retracted therefrom. For example, the tissue recruitment area 172 may have an inner diameter configured to allow deployment of the second grasping device 104 after the first grasping device 104 has been maneuvered to grasp tissue. The tissue recruitment area 172 may also be sized, shaped, and configured to receive tissue grasped by the grasping devices 104 when the grasping devices 104 are retracted back into the tissue recruitment area 172, such as to maintain closure of a defect.

The shroud 170 may be sized, shaped, and configured such that the grasping devices 104 retained in, extended from, and retracted into the shroud 170. The shroud 170 may substantially cover the grasping device 104 when the grasping devices 104 are in an unactuated position, such as when the tissue recruiting assembly 102 is inserted into the desired position in a body, such as through an endoscope. The shroud 170 may permit the grasping devices 104 to be extended from the shroud 170 via the actuation elements 208 to grasp tissue in different locations. For example, the shroud 170 may be configured to permit the actuation elements 208 to flex or bend such that the grasping devices 104 may independently grasp tissue at spaced apart locations, such as opposite sides of a defect. The shroud 170 may also be configured such that the grasping devices 104 may be retracted into the shroud 170 in a retracted position such that the grasped tissue is received in the tissue recruitment area 172.

In some embodiments, the shroud 170 is operable to retain the grasping devices 104 in a locked position. The locked position may substantially correspond to the retracted position of the grasping devices 104. The proximal end of the shroud 170 may be narrower than a distal portion of the shroud 170, such as the portion of the shroud 170 defining the tissue recruitment area 172. The proximal end of the shroud 170 may be narrower such that the proximal end of the shroud 170 maintains the position of the grasping device 104 when the grasping devices 104 are retracted into the retracted position, such as to retain the grasped tissue in the tissue recruitment area 172. The proximal end of the shroud 170 may substantially retain the grasping devices 104 in the retracted position via a compression fit, an interference fit, and/or frictional force. For example, the shroud 170 may comprise polymer, metal, or a combination thereof and/or may comprise a polymer liner such that the shroud 170 substantially conforms to the proximal ends of the grasping devices 104, such as the coupling portions 110, when the grasping devices 104 are retracted to the retracted position, such as to maintain the position of the coupling portions 110 of the grasping devices 104. The grasping devices 104 may be substantially prevented from translating and/or rotating when the grasping devices 104 are in the locked position in the shroud 170.

Figure 20A:
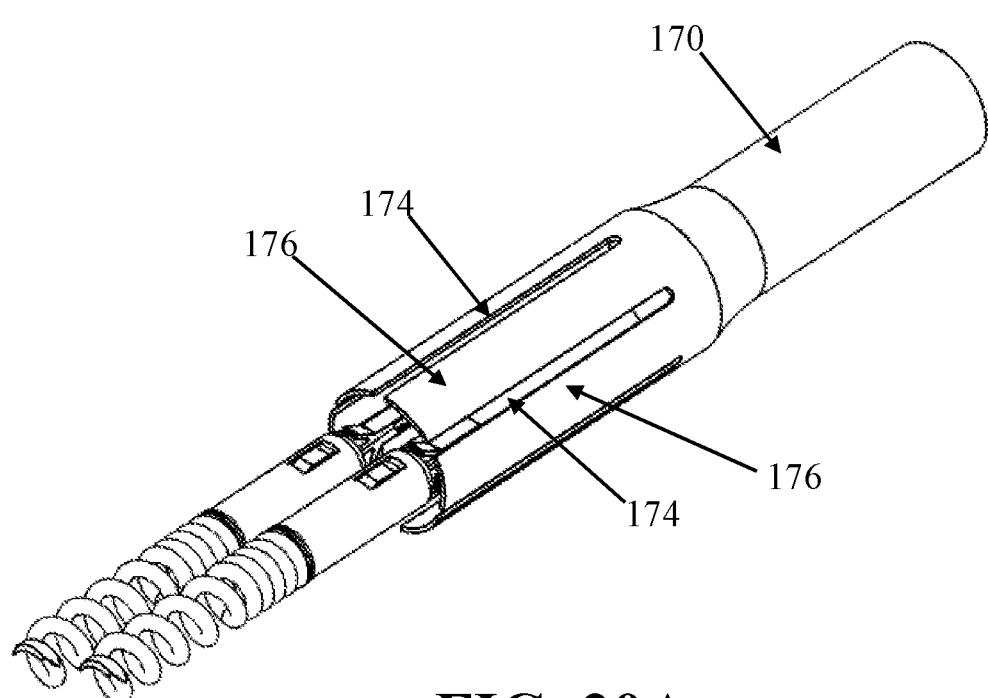
FIG. 20A is a perspective view of grasping devices extending from a shroud according to another embodiment.
Figure 20B:
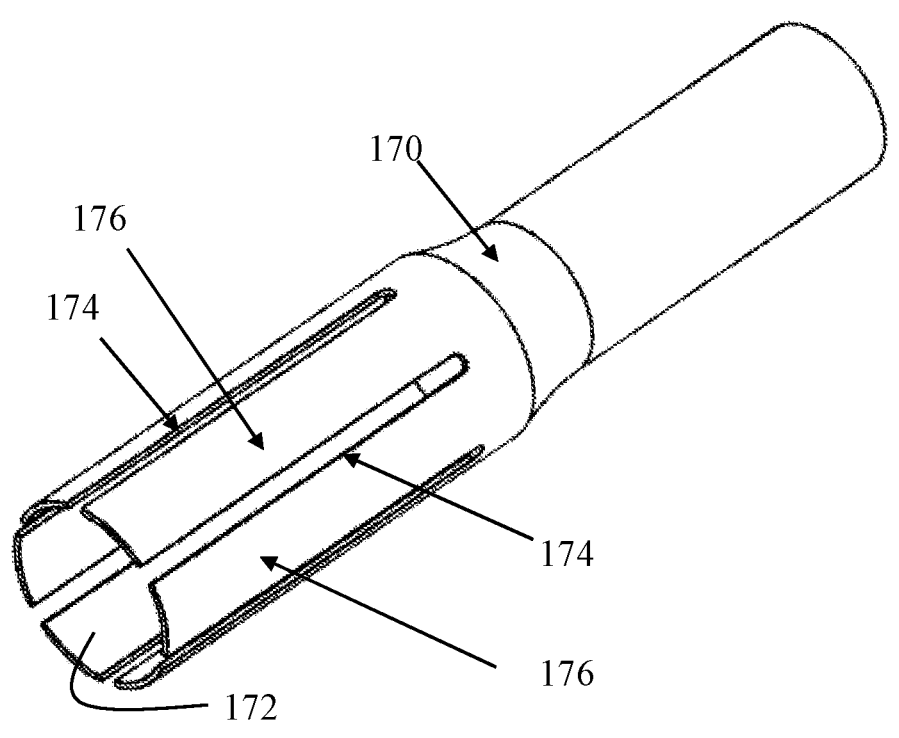
FIG. 20B is a perspective view of the shroud of FIG. 20A.
Figure 20C:
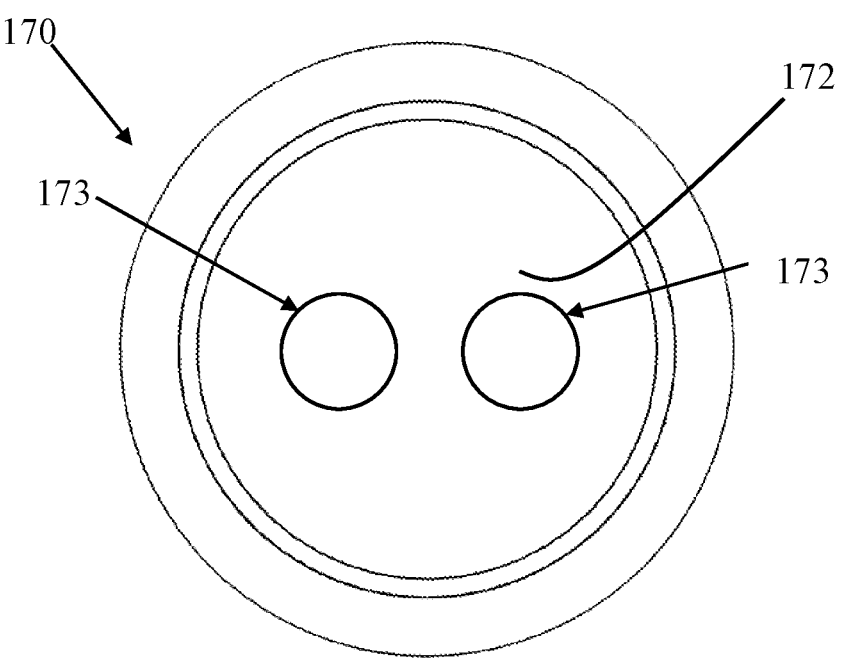
FIG. 20C is a front view of the shroud of FIG. 20A according to one embodiment.
Figure 20D:
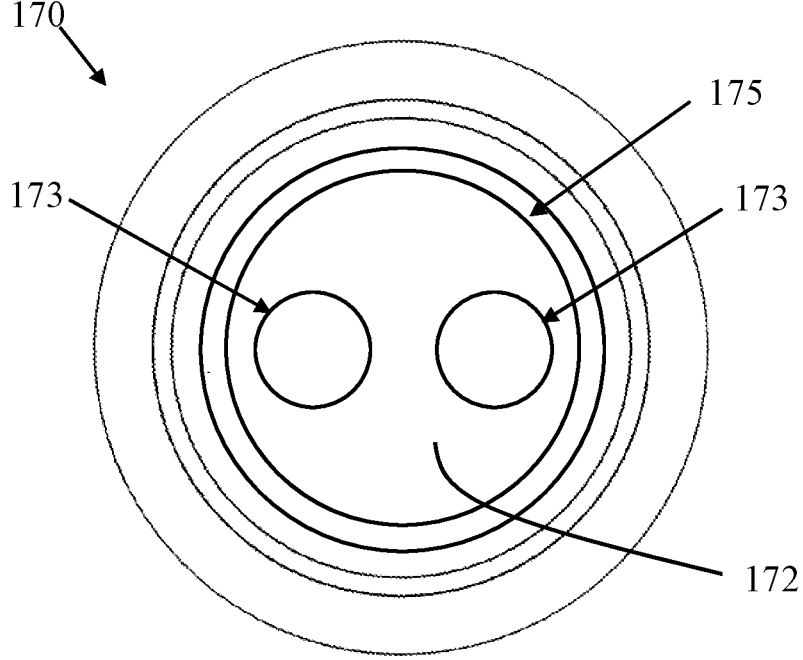
FIG. 20D is a front view of the shroud of FIG. 20B according to another embodiment.

In some embodiments, as shown in FIGS. 20C-20D, the shroud 170 may include or otherwise incorporate one or more lumens 173 extending at least partially through the shroud 170. The lumens 173 may be substantially hollow tubes configured to permit the grasping devices 104 to extend therefrom. The lumens 173 may be flexible such that the grasping devices 104 and actuation elements 208 may be maneuvered such that the grasping devices 104 may grasp tissue at different locations. The lumens 173 may prevent the actuation elements 208 from tangling when the actuation elements 208 are extended, rotated, and retracted, such as to control the operation of the grasping devices 104. The lumens 173 may also assist in the retraction of the actuation elements 208 and grasping devices 104 after the grasping devices 104 grasp tissue such that the tissue is properly recruited into the tissue recruitment area 172. For example, the lumens 173 may guide the extension and retraction of the actuation elements 208 and grasping devices 104 such that the actuation elements 208 do not tangle and such that actuation elements 208 are substantially aligned when retracted, such as aligned in a center portion of the shroud 170. In some embodiments, the lumens 173 are configured to maintain the retracted position of the grasping devices 104, such as by via a compression fit, an interference fit, and/or frictional force with the coupling portions 110 of the grasping devices 104. In some embodiments, the proximal end of the shroud 170 may be substantially solid except for the openings defined by the lumens 173.

Figure 20E:
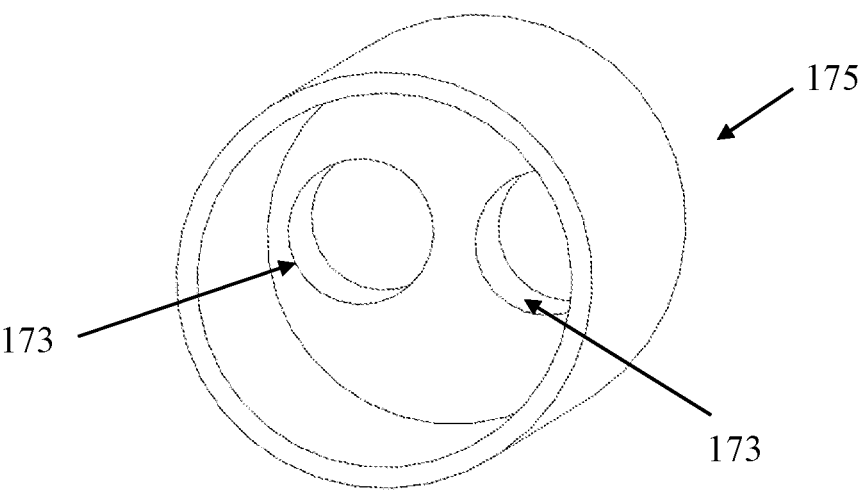
FIG. 20E is a perspective view of a hood of the shroud of FIG. 20B according to one embodiment.
Figure 20F:
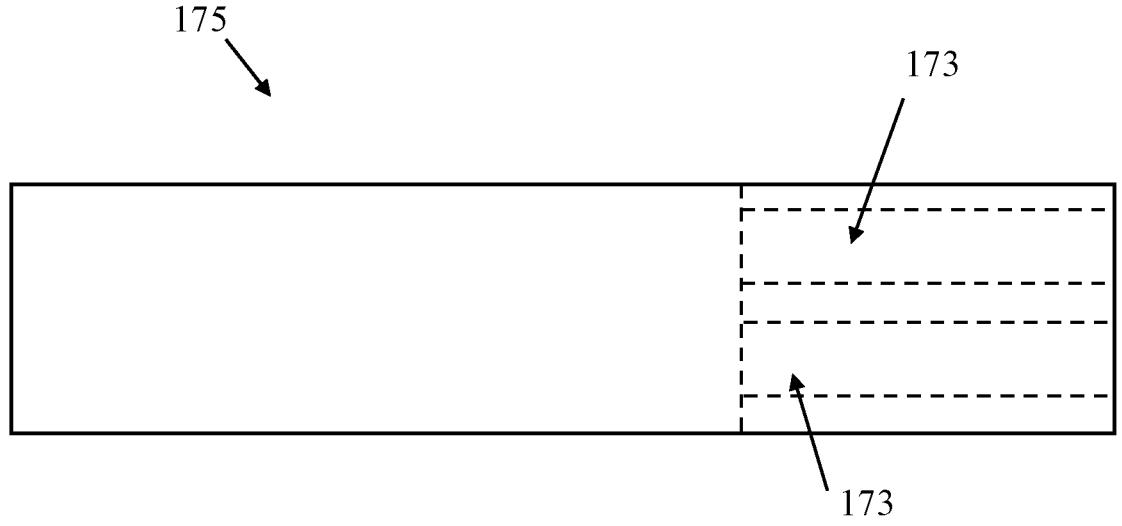
FIG. 20F is a side schematic illustration of the hood of FIG. 20E.

As shown in FIG. 20D-20F, the shroud 170 may include a hood 175 disposed in the tissue recruitment area 172. The hood 175 may be substantially cylindrical and may have a substantially solid proximal end defining the one or more lumens 173. The distal end of the hood 175 may be substantially hollow and sized, shaped, and configured to receive the grasping devices 104. The hood 175 may also be configured to prevent the actuation elements 208 from tangling when the actuation elements 208 are extended, rotated, and retracted, such as to control the operation of the grasping devices 104, and assist in the retraction of the actuation elements 208 and grasping devices 104 after the grasping devices 104 grasp tissue such that the tissue is properly recruited into the tissue recruitment area 172. The hood 175 may be configured to retain the grasping devices 104 in the retracted position, such as by via a compression fit, an interference fit, and/or frictional force with the coupling portions 110 of the grasping devices 104. In some embodiments, the device 100 may not include a hood 175 and the catheter 302 may prevent the actuation elements 208 from tangling during operation. For example, the struts 305 of the catheter 302 of FIGS. 11D-11G may prevent the actuation elements 208 from tangling during operation. The catheter 302 may also include individualized lumens formed from a polymer.

In some embodiments, the one or more shrouds 170 are configured to proximally collapse or retract or compress against the tissue after the grasping devices 104 secure tissue and are retracted proximally, such as into the tissue recruitment area 172. For example, the one or more shrouds 170 may include a stress relief feature which allows the distal end of the shroud 170 to proximally collapse or retract after the grasping devices 104 have been maneuvered to grasp tissue and proximally retracted into the tissue recruitment area 172 to recruit the grasped tissue. The shrouds 170 may also be configured to fan outwardly against the tissue as the grasping devices 104 are recruited, such as to decrease the longitudinal length of the shroud.

As shown in FIGS. 20A-20B, the shroud 170 includes a plurality of slots 174 extending through the body of the shroud 170 from the distal end toward the proximal end. The slots 174 may define a plurality of projections 176 extending toward the distal end of the shroud 170. The projections 176 may substantially cover the grasping devices 104 when the grasping devices 104 are in the undeployed state. After the grasping devices 104 have been maneuvered to grasp tissue, the retraction of the grasping devices 104 may cause the recruited tissue to abut the distal end of the shroud 170. Further proximal retraction of the grasping devices 104 into the tissue recruitment area 172 may collapse or otherwise move the projections 176 toward the proximal end of the shroud 170, such as to reduce the length of the shroud 170. For example, the slots 174 may permit the projections 176 to compress after the grasping devices 104 have been maneuvered to grasp tissue and recruited into the tissue recruitment area 172 of the shroud 170, such as to reduce the distance the shroud 170 extends outwardly from the tissue when the grasping devices 104 are deployed to close the defect. The projections 176 may compress in an elastic fashion such that the projections 176 may return to the original shape after being compressed. For example, the projections 176 may compress when tissue is recruited toward the shroud 170 and the projections 176 may return to the original shape after the tissue is released.

While the shroud 170 has been described as including a plurality of slots 174 defining the stress relief feature, it will be understood that the one or more shrouds 170 may include other suitable stress relief features. For example, additionally or alternatively, the one or more shrouds 170 may include crumple zones, circumferential folds which permit the shroud 170 to fold proximally, helical coils which permit the shroud 170 to compress as the grasping devices 104 are recruited, and/or apertures extending around the tissue recruiting portions (FIG. 30) and materials which permit the shroud 170 to roll or fold proximally, or combinations thereof.

In some embodiments, the grasping devices 104 may be locked in position in the shroud 170 when the grasping devices 104 are sufficiently retracted into the shroud 170 such that the positions of the grasping devices 104 are maintained relative to the shroud 170, such as described below. In some embodiments, the shroud 170 is operable to retain the positions of the grasping devices 104 in the retracted position by a compression fit, an interference fit, and/or frictional force with the coupling portions 110 of the grasping devices 104, such as described below. In some embodiments, the force required to lock the grasping devices 104 in the shroud 170 is between about 4 pounds and about 5 pounds.

Figures 21A, 21B, 21C, 21D:
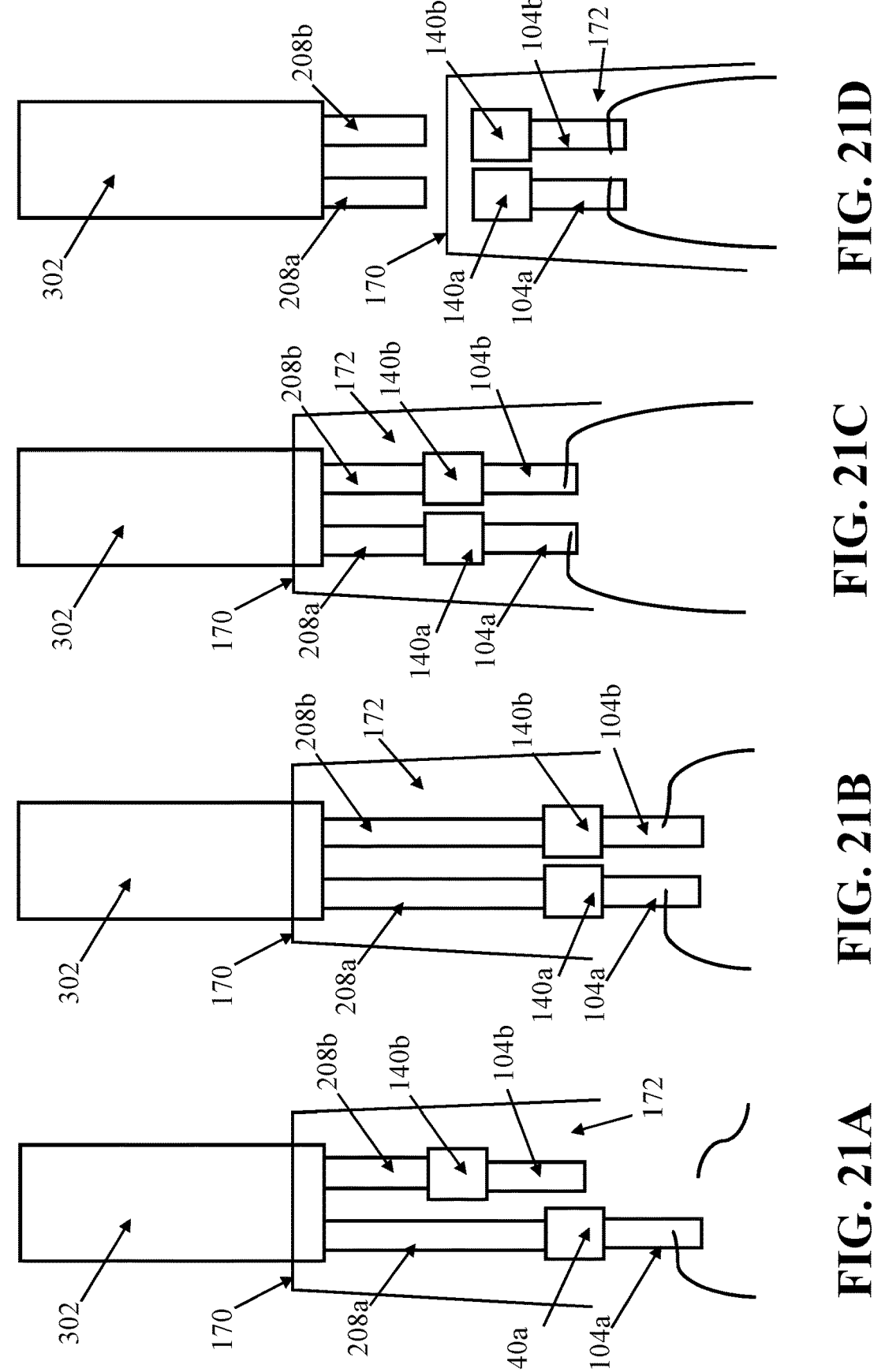
FIGS. 21A-21D are schematic illustrations showing an illustrative example of recruiting tissue into a shroud to close a defect and deploying the grasping devices and shroud to maintain the closure of the defect.

As shown in FIGS. 21A-21B, two grasping devices 104 may be maneuvered to grasp target tissue, such as on opposite sides of a defect, and recruited into the shroud 170, such as to recruit the grasped tissue toward or into the tissue recruitment area 172 of the shroud 170 and close the defect. The grasping devices 104 may be decoupled from the actuation elements 208 and the shroud 170 may be decoupled from the catheter 302, such as to maintain the closure of the defect via the grasping devices 104. In the illustrated embodiment, a first grasping device 104a is coupled with a first actuation element 208a and a second grasping device 104b is coupled with a second actuation element 208b. A first coupler 140a is included to operably couple the first grasping device 104a with the first actuation element 208a and a second coupler 140b is included to operably couple the second grasping device 104b with the second actuation element 208b. While the grasping devices 104a, 104b are described as being operably coupled with the actuation elements 208a, 208b via couplers 140a, 140b, it will be understood that the grasping devices 104a, 104b may be operably coupled directly to the actuation elements 208a, 208b.

The endoscope and/or the catheter 302 may be oriented above an identified defect such that the grasping devices 104a, 104b are disposed substantially above the defect. As shown in FIG. 21A, the first grasping device 104a may be operated, such as via the actuation assembly 200, to grasp tissue on a first side of the defect. For example, the first actuation element 208a may be rotated and translated such that the first grasping device 104a securely grasps the tissue.

As shown in FIG. 21B, the second grasping device 104b may be operated, such as via the actuation assembly 200, to grasp tissue on a second side of the defect. The endoscope and/or the catheter 302 may be manipulated such that the second grasping device 104b is in a position above the second side of the defect when the second actuation element 208b is manipulated to control the second grasping device 104b. For example, the second actuation element 208b may be rotated and translated such that the second grasping device 104b securely grasps tissue.

As shown in FIG. 21C, the first and second actuation elements 208a, 208b may be proximally retracted toward the catheter 302. The actuation elements 208a, 208b may be proximally retracted, such as via the actuation assembly 200, such that the grasping devices 104a, 104b and grasped tissue are brought toward the catheter 302 and toward or into the tissue recruitment area 172 of the shroud 170. The grasping devices 104a, 104b may be proximally retracted into the shroud 170 via the actuation elements 208a, 208b such that the shroud 170 locks the grasping devices 104a, 104b into the retracted position, such as to maintain the translational and rotational positions of the grasping devices 104a, 104b.

As shown in FIG. 21D, the grasping devices 104a, 104b may be decoupled from the respective actuation elements 208a, 208b and the shroud 170 may be decoupled from the catheter 302. The grasping devices 104a, 104b may be disposed in the shroud 170 such that grasped tissue from opposing sides of the defect are held together by the grasping devices 104a, 104b, such as to maintain substantial closure of the defect. The grasping devices 104a, 104b may be decoupled from the actuation elements 208a, 208b by operably decoupling the couplers 140a, 140b from the actuation elements 208a, 208b, as described below. The shroud 170 may be decoupled from the catheter 302 as described below. The tissue recruiting assembly 102 may be configured to lock the grasping devices 104 in the shroud 170 after the grasping devices 104 have been decoupled from the actuation elements 208 and the shroud 170 has been decoupled from the catheter 302, as described below. While the couplers 140 have been described as remaining with the grasping devices 104 when the grasping devices 104 are decoupled from the actuation elements 208, it will be understood that the couplers 140 may be coupled to the actuation elements 208.

The grasping devices 104 may be operably coupled with the actuation elements 208 in a variety of manners such that the grasping devices 104 may be decoupled from the actuation elements 208, such as after the grasping devices 104 have grasped tissue and been recruited toward or into the tissue recruitment area 172 of the shroud 170. In some embodiments, the coupling portions 110 of the grasping devices 104 are operably coupled directly to the distal end of the actuation elements 208. In other embodiments, the coupling portions 110 of the grasping devices 104 are operably coupled to the distal end of the actuation elements 208 via couplers 140.

As shown in FIGS. 22A-23B, the grasping device 104 may include one or more tabs 132 configured to operably couple the grasping device 104 with the actuation element 208. The tabs 132 extend from the proximal end of the coupling portion 110 and are flexible or pivotable, such as to couple with the actuation element 208, as described below. In some embodiments, the tabs 132 are laser cut from the distal end of the grasping device 104. In other embodiments, the tabs 132 are laser cut from the distal end of the actuation element 208 and the detents 134 are disposed in the proximal end of the grasping device 104.

Figures 22A, 22B:
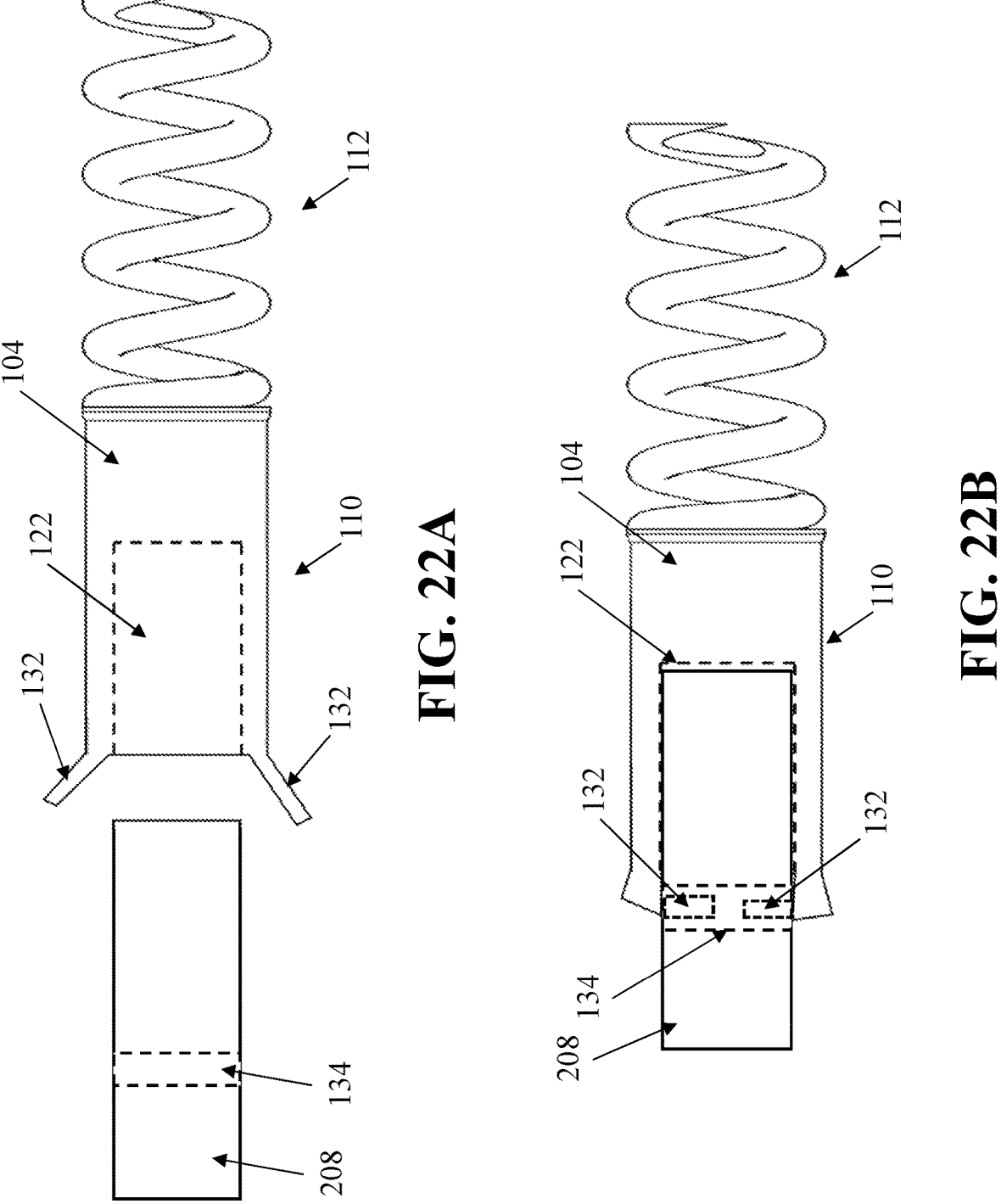
FIGS. 22A and 22B are schematic illustrations showing an actuation element coupled to a grasping device according to one embodiment.

In some embodiments, as shown in FIGS. 22A-22B, the actuation element 208 includes one or more detents 134 configured to engage with and operably retain the tabs 132 of the grasping device 104. The detents 134 may extend into the outer surface of the actuation element 208 near the distal end. The detents 134 may be recessed, apertures, cut outs, or slots extending radially inwardly into the outer surface of the actuation element 208. In the illustrated embodiment, the detent 134 extends through the actuation element 208. In other embodiments, the detents 134 may be recesses, grooves, bores, or slots extending partially into the outer surface of the actuation element 208. The actuation element 208 may have a number of detents 134 in a configuration around the outer surface of the actuation element 208 corresponding with the number and position of tabs 132 of the grasping device 104. In other embodiments, the tabs 132 may couple with the outer surface of the actuation element 208 via friction such that the detents 134 may be omitted.

The tabs 132 of the grasping device 104 may be operable to couple the grasping device 104 to the actuation element 208. The distal end of the actuation element 208 may be inserted into the receiving portion 122 of the grasping device 104 and the tabs 132 of the grasping device 104 may be bent radially inwardly to insert into or otherwise engage with the detents 134 of the actuation element 208. When the tabs 132 of the grasping device 104 are inserted into or otherwise engaged with the detents 134 the grasping device 104 may remain coupled, either directly or indirectly, with the distal end of the actuation element 208. The translational and rotational movement of the actuation element 208 may be transferred to the grasping device 104, such as to maneuver the grasping device 104 to grasp tissue, when the tabs 132 of the grasping device 104 couple with the detents 134 of the actuation element 208.

The tabs 132 are also operable to decouple the grasping device 104 from the actuation element 208, such as after the grasping device 104 has been maneuvered to grasp tissue. The actuation element 208 may be retracted proximally with sufficient force, such as via the actuation assembly 200, to disengage the tabs 132 from the detents 134, such as to push or pivot the tabs 132 radially outwardly from the detents 134. When the tabs 132 are disengaged from the detents 134, the grasping device 104 may be decoupled from the actuation element 208. For example, the grasping device 104 may be graspingly inserted into tissue and the actuation element 208 may be proximally retracted, such as via the actuation assembly 200, to disengage the tabs 132 of the grasping device 104 from the detents 134 of the actuation element 208. The force required to decouple the grasping device 104 from the actuation element 208 may be more than the force required to pull the grasping device 104 out of the tissue. In some embodiments, the force required to decouple the grasping device 104 from the actuation element 208 is between about 3 pounds and about 6 pounds. After the tabs 132 have been decoupled from the detents 134, the actuation element 208 may be retracted proximally from the grasping device 104, such as with the grasping device 104 graspingly inserted into the tissue.

Figures 23A, 23B:
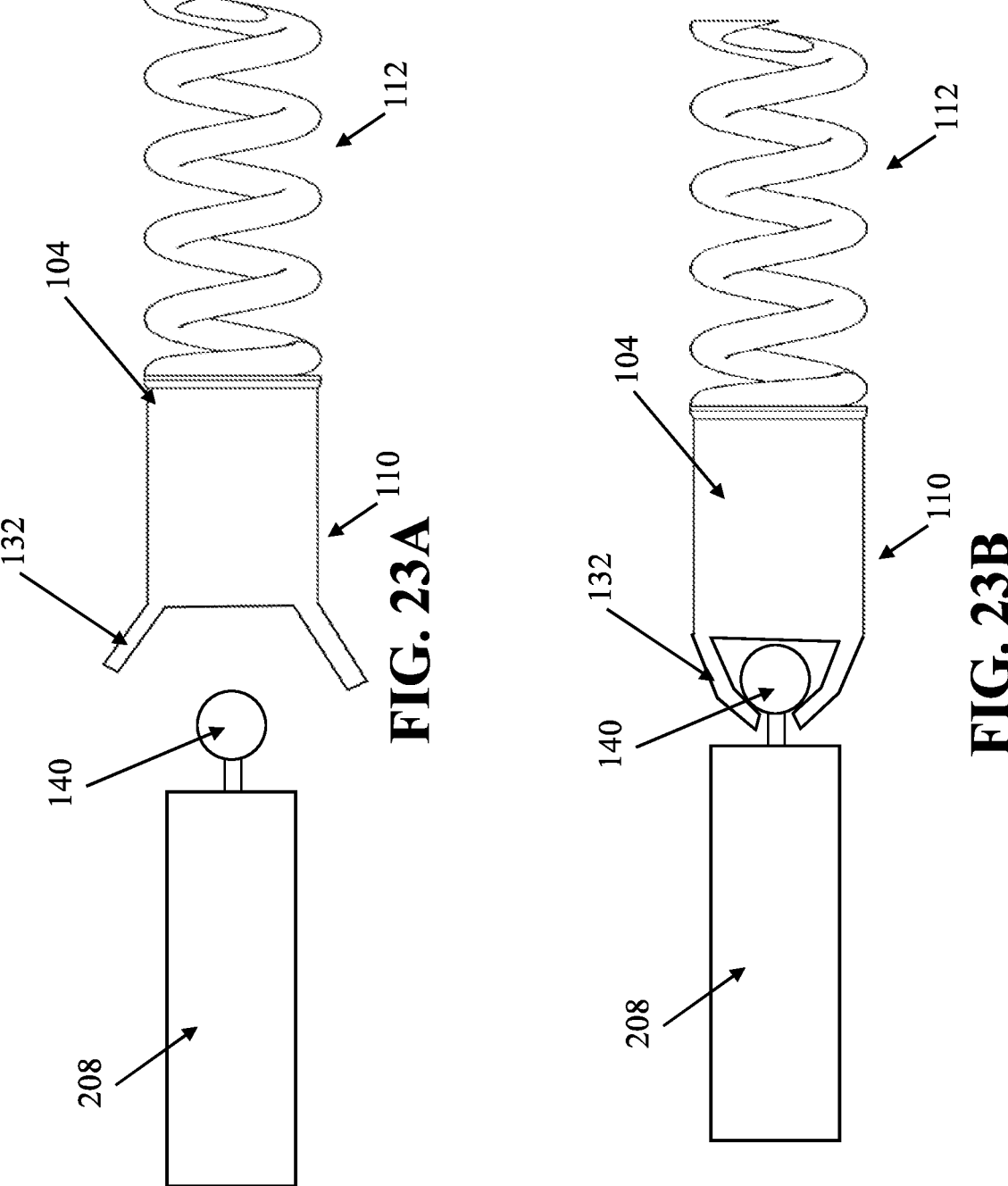
FIGS. 23A and 23B are schematic illustrations showing an actuation element coupled to a grasping device via a coupler according to one embodiment.

As shown in FIGS. 23A-23B, the tissue recruiting assembly 102 includes one or more couplers 140 operable to couple the grasping devices 104 to the actuation elements 208. The couplers 140 may be sized, shaped, and configured to couple the grasping devices 104 to the actuation elements 208 during operation, such as to maneuver the grasping devices 104 to grasp tissue on opposite sides of a defect, and to decouple the grasping devices 104 from the actuation elements 208, such as after the grasping devices 104 have been maneuvered to grasp tissue.

As shown in FIGS. 23A-23B, the coupler 140 may be attached to the distal end of the actuation element 208 to operatively couple the actuation element 208 with the grasping device 104. The coupler 140 may be sized, shaped, and configured to be operably retained by the tabs 132 of the grasping device 104 to couple the actuation element 208 to the grasping device 104. In the illustrated embodiment, the coupler 140 has a substantially spherical coupling portion at a distal end configured to couple with the tabs 132 of the grasping device 104. In other embodiments, the coupler 140 is asymmetric, rectangular, obround, triangular, or the like. In some embodiments, the coupler 140 is welded to or from the distal end of the actuation element 208. In some embodiments, the coupler 140 includes a neck portion fixed to the distal end of the actuation element 208 to the grasping device 104 such that the actuation element 208 may control the position and rotation of the grasping device 104. The coupler 140 may also be sized, shaped, and configured to decouple from the grasping device 104 after the grasping device 104 has been actuated or otherwise deployed.

The tabs 132 of the grasping device 104 may be configured to operably retain the coupling portion of the coupler 140. The tabs 132 may be configured to flex or bend around the coupler 140, such as the spherical coupling portion of the coupler 140, to couple the actuation element 208 with the grasping device 104. In some embodiments, the tabs 132 are laser cut from the proximal end of the grasping device 104.

The coupler 140 may be disposed near the coupling portion 110 of the grasping device 104, such as being inserted in the receiving portion 122 of the grasping device 104, and the tabs may be bent radially inwardly around the coupling portion of the coupler 140. The bent tabs 132 may prevent or otherwise restrict the coupler 140 from being retracted from the grasping device 104. For example, the tabs 132 may be sized, shaped, and configured such that the coupler 140 remains partially disposed in the receiving portion 122 of the grasping device 104 during deployment of the grasping device 104. For example, the tabs 132 may be sized and shaped to substantially cover a proximal side of the coupler 140. Additionally, the tabs 132 may be configured such that the tabs 132 remain in position around the coupler 140 during positioning and rotation of the grasping device 104.

The grasping device 104 may also be decoupled from the coupler 140, such as after the grasping device 104 has been maneuvered to grasp tissue. The actuation element 208 may be retracted proximally with sufficient force, such as via the actuation assembly 200, to disengage the tabs 132 from retaining the coupler 140 to the grasping device 104. The actuation element 208 may be retracted with a force sufficient such that the retraction of the coupler 140 bends the tabs 132 of the grasping device 104 radially outwardly such that the tabs 132 no longer surround the coupling portion of the coupler 140. The force required to decouple the grasping device 104 from the actuation element 208 may be greater than the force required to pull the grasping device 104 out of the tissue. The tabs 132 may be configured to flex or otherwise release the coupler 140 when a force between about 1 pound and about 10 pounds, such as between about 3 pounds and about 6 pounds, is applied to the actuation element 208.

The coupler 140 may then be retracted from the grasping device 104 to decouple the actuation element 208 and the coupler 140 from the grasping device 104. The coupler 140 may remain coupled to the actuation element 208. For example, the grasping device 104 may be graspingly inserted into tissue and the actuation element 208 may be proximally retracted such that the coupler 140 bends the tabs 132 radially outwardly. After tabs 132 have bent radially outwardly, the actuation element 208 and the coupler 140 may be retracted proximally from the grasping device 104, such as with the grasping device 104 graspingly inserted into the tissue and locked in the shroud 170.

In some embodiments, the coupler 140 has a size, shape, and configuration which permits the actuation element 208 to be operably coupled with the grasping device 104. The coupler 140 may have a size, shape, or configuration that permits the coupler 140 to be inserted into the receiving portion 122 of the grasping device 104 when the coupler 140 is in a certain orientation and/or is disposed at a certain orientation relative to the receiving portion 122. The coupler 140 may interlock with the receiving portion 122 of the grasping device 104 after the coupler 140 is inserted into the receiving portion 122. For example, the coupler 140 may be rotated in the receiving portion 122, the coupler 140 may expand in the receiving portion 122, or the receiving portion 122 may be closed around the coupler 140. The coupler 140 may remain interlocked with the coupling portion 110 of the grasping device 104 such that the translation and rotation of the actuation element 208 is transferred to the grasping device 104. The coupler 140 may be decoupled from the receiving portion 122 of the grasping device 104, such as after the grasping device 104 has been maneuvered to grasp tissue and the grasping device 104 has been locked in the retracted position, and the actuation element 208 may be retracted from the grasping device 104.

Figures 24A, 24B:
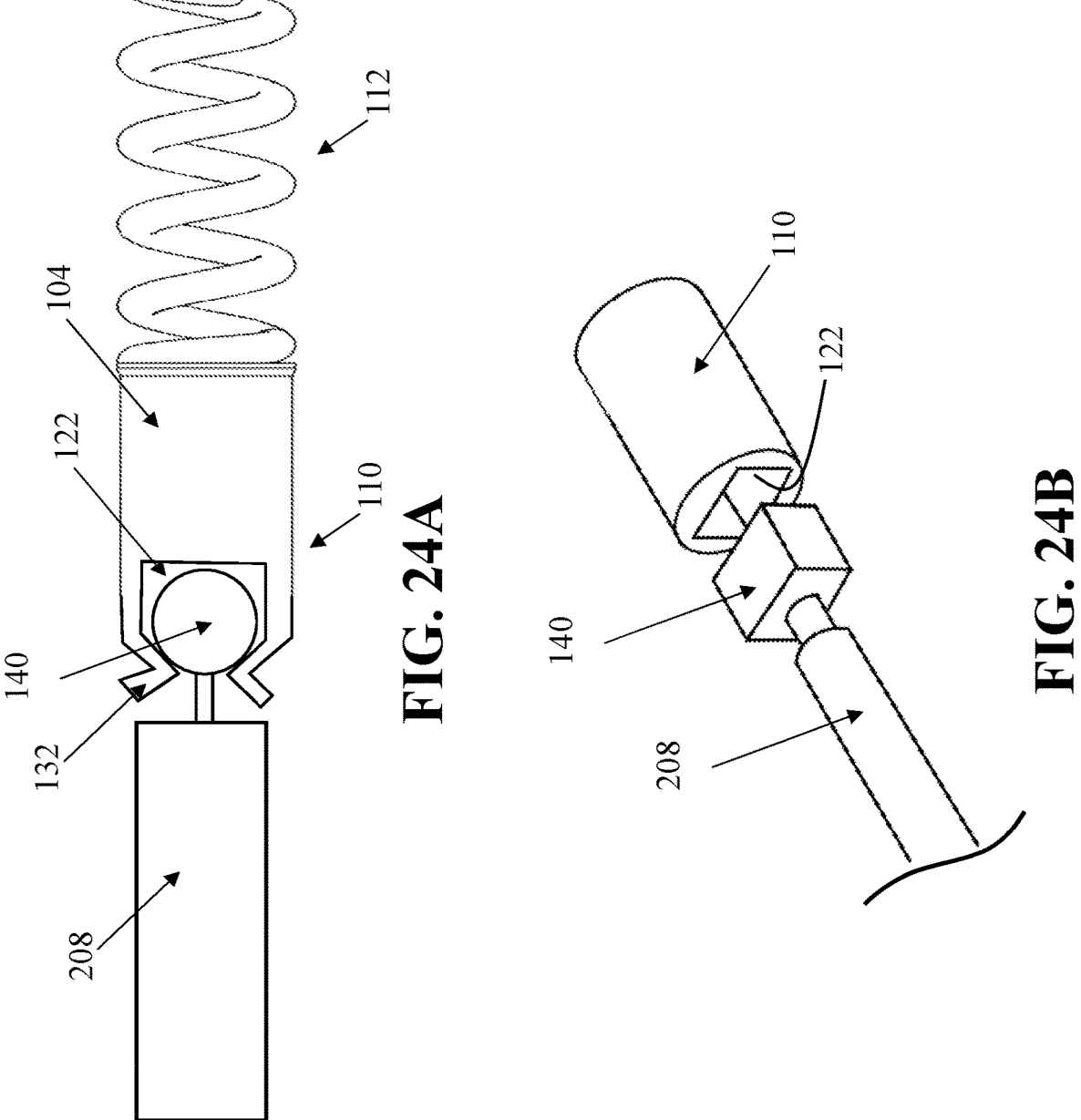
FIG. 24A is a schematic illustration showing an actuation element coupled to a grasping device via a coupler according to one embodiment.
FIG. 24B is a perspective view of an actuation element coupling with a connecting portion of a grasping device via a coupler according to another embodiment.

As shown in FIG. 24A, the coupler 140 may have a substantially spherical coupling portion at a distal end configured to couple with the grasping device 104. The coupler 140 may be substantially similar to the coupler 140 of FIGS. 23A-23B. The coupler 140 may be inserted into the receiving portion 122 of the grasping device 104 such that the coupling portion of the coupler 140 is disposed in the receiving portion 122. The receiving portion 122 may have a substantially circular opening (FIG. 10) sized to receive the coupling portion of the coupler 140. After the coupling portion of the coupler 140 is inserted into the receiving portion 122, the coupling portion 110 of the grasping device 104 may be crimped proximally from the coupling portion of the coupler 140 (e.g., the ball) to operably retain the coupler 140 in the receiving portion 122 of the grasping device 104. The actuation element 208 may remain coupled to the grasping device 104 while the coupler 140 is disposed in the receiving portion 122 such that translation and rotation of the actuation element 208 may transfer to the grasping device 104, such as to grasp tissue with the grasping device 104. In some embodiments, the coupling portion 110 of the grasping device 104 may also be crimped, welded, swaged, or otherwise connected distally from the coupler 140, such as to further secure the coupler 140 in the receiving portion 122.

The coupler 140 may be operably decoupled from the grasping device 104, such as after the grasping device 104 has been maneuvered to grasp tissue. The actuation element 208 may be proximally retracted with sufficient force to break or otherwise disrupt the one or more connections, such as the crimp, in the grasping device 104 such that the coupler 140 may be retracted from the receiving portion 122. The force required to decouple the grasping device 104 from the actuation element 208 may be greater than the force required to pull the grasping device 104 out of the tissue. The actuation element 208 and the coupler 140 may be retracted proximally from the grasping device 104, such as with the grasping device 104 deployed in the tissue and the locked in the shroud 170.

While the coupler 140 of FIG. 24A has been described as substantially spherical, it will be understood that the coupler 140 and the receiving portion 122 may have other suitable sizes, shapes, and configurations. For example, the coupler 140 may be rectangular, helical, screw-shaped, asymmetrical, or other shape suitable to translate the translation and rotation of the actuation element 208 to the grasping device 104 when the coupler 140 is received in the receiving portion 122 of the grasping device 104.

In some embodiments, the coupler 140 has a size, shape, and configuration that permits the coupler 140 to be inserted into the receiving portion 122 of the grasping device 104 and interlocked with the grasping device 104 until the coupler 140 is moved to an unlocked position. As shown in FIG. 24B, the receiving portion 122 of the grasping device 104 may have a proximal opening which substantially corresponds to a shape of the coupler 140. The distal portion of the receiving portion 122 may have a width or diameter larger than the proximal opening of the receiving portion 122. The coupler 140 may be inserted into the receiving portion 122 in a position corresponding to the shape of the proximal opening. After the coupler 140 is inserted through the proximal opening into the retaining portion, the coupler 140 may be rotated to operably secure the coupler 140 in the receiving portion 122.

In some embodiments, the receiving portion 122 is configured such that the coupler 140 may be rotated a predetermined amount in the receiving portion 122 such that the coupler 140 operably locks in place in the receiving portion 122. For example, rotating the coupler 140 may cause the cross section of the coupler 140 to have a shape which prevents the coupler 140 from being retracted from the proximal opening of the receiving portion 122. In some embodiments, the coupler 140 operably locks in place in the receiving portion 122 when the coupler 140 is rotated 90 degrees after being inserted through the opening of the receiving portion 122. The receiving portion 122 may include one or more locking elements which prevent or otherwise restrict the coupler 140 from rotating or translating in the receiving portion 122 during deployment of the grasping device 104. For example, the receiving portion 122 may include one or more tabs which bend once the coupler 140 is properly disposed in the receiving portion 122 and restrict the opposite rotation of the coupler 140 to operably retain the coupler 140 in position in the receiving portion 122. In some embodiments, the coupler 140 may be magnetically locked in the receiving portion 122 until a sufficient force is exerted on the actuation element 208 to overcome the magnetic attraction.

During operation, the actuation element 208, such as via the actuation assembly 200, may be controlled to deploy the grasping device 104. For example, the actuation element 208 may be positioned and rotated such that the grasping device 104 is deployed in the tissue. After the grasping device 104 has been deployed, the actuation element 208 may be rotated, such as in a direction opposite the rotation to lock the coupler 140 in the receiving portion 122, such that the shape of the coupler 140 is aligned with the shape of the proximal opening of receiving portion 122. The actuation element 208 may be retracted proximally to retract the coupler 140 from the receiving portion 122 thereby decoupling the actuation element 208 and the grasping device 104.

In the illustrated embodiment, the coupler 140 is a substantially rectangular block and the proximal opening of the receiving portion 122 is similarly rectangular. However, it will be understood that the coupler 140 and the proximal opening of the receiving portion 122 may have any suitable shapes and configurations. For example, the coupler 140 may be ovular, obround, elliptical, triangular, pentagonal, helical, or any other suitable shape.

Additionally, the coupling portion 110 of the grasping device 104 may have additional features which operatively retain the coupler 140 in the receiving portion 122. The coupling portion 110 may have a plurality of cut-outs or slots extending proximally into the grasping device 104 from the distal end (e.g., FIGS. 14A-17B) which may receive a portion of the coupler 140. The coupler 140 may be inserted into the receiving portion 122 and the slots may allow the proximal end of the coupling portion 110 to flex radially outwardly. The coupler 140 may be inserted farther into the receiving portion 122 such that the sides of the coupler 140 extend at least partially into the receiving areas defined by the slots. For example, radial outer portions of the coupler 140 may extend radially outwardly from the receiving portion 122 through the slots. The proximal end of the coupling portion 110 may then move radially inwardly to surround the proximal end of the coupling portion of the coupler 140 to retain the coupler 140 in the receiving portion 122.

The configuration of the coupling portion 110, such as the receiving areas and the inner diameter of the receiving portion 122, may retain the coupler 140 in the receiving portion 122 of the grasping device 104 during actuation of the grasping device 104. After the grasping device 104 has been inserted into tissue, the actuation element 208 may be proximally retracted with sufficient force to flex the proximal end of the coupling portion 110 radially outwardly, such as via contact with the coupler 140, such that the coupler 140 may be retracted from the receiving portion 122. The force required to decouple the grasping device 104 from the actuation element 208 may be greater than the force required to pull the grasping device 104 out of the tissue. The actuation element 208 and the coupler 140 may be retracted proximally from the grasping device 104, such as with the grasping device 104 deployed in the tissue and locked in the shroud 170.

While the coupler 140 has been described as being substantially spherical or rectangular to couple with the receiving portion 122 of the grasping device 104, it will be understood that the coupler 140 may have other shapes and configurations to operably couple with the grasping device 104. For example, in some embodiments, the coupler 140 may have one or more projections which extend radially outwardly to be secured in the receiving portion 122 of the grasping device 104, such as in the receiving areas defined by the slots. The coupler 140 may be sized, shaped, and configured to operably interlock with the receiving portion 122 of the grasping device 104 such that the actuation element 208 may control the deployment of the grasping device 104 and to decouple the coupler 140 from the grasping device 104 after deployment of the grasping device 104, such as by rotation of the coupler 140.

Figures 25A, 25B, 25C:
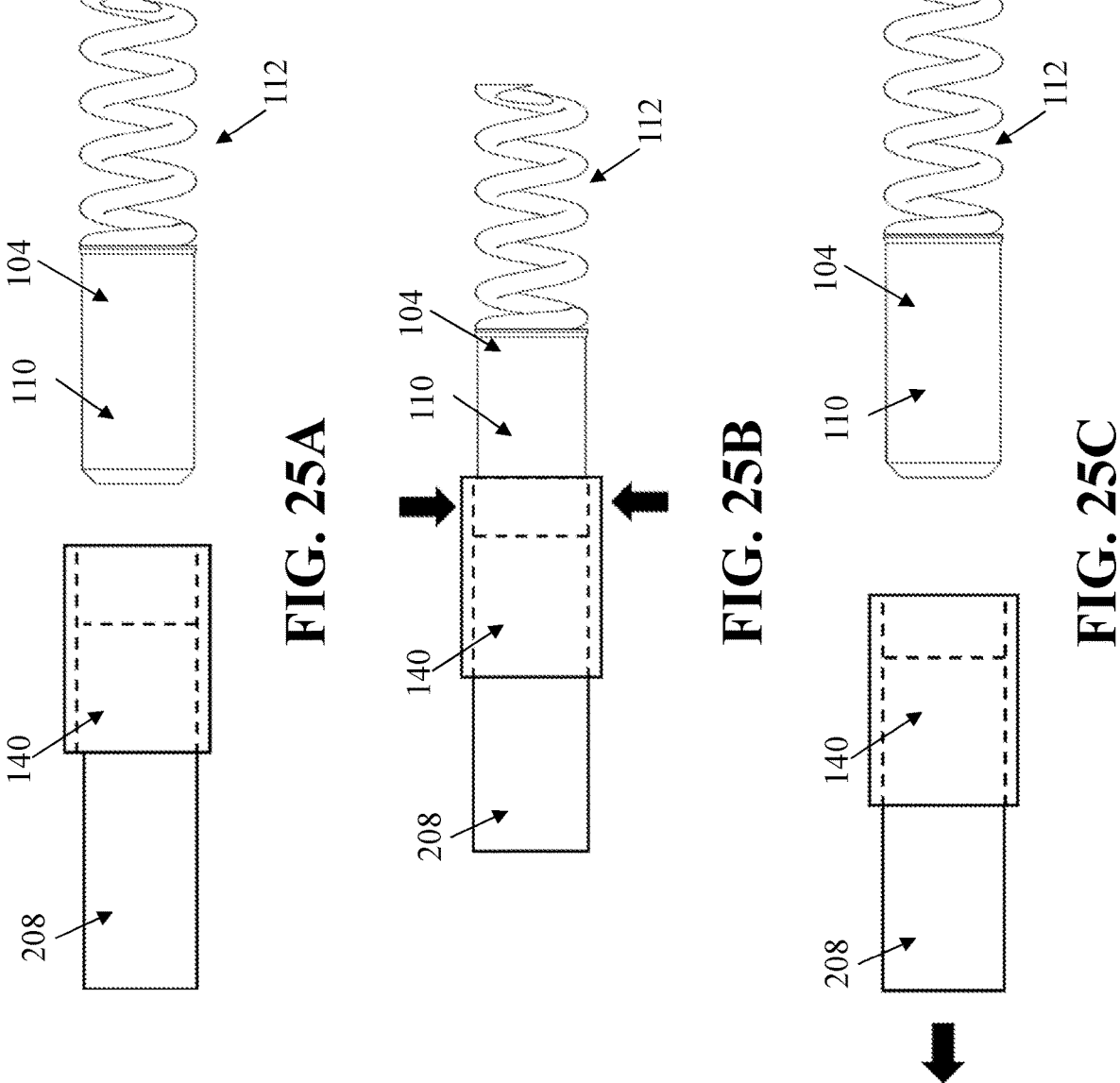
FIGS. 25A-25C are schematic illustrations showing an actuation element coupled to and decoupled from a grasping device via a coupler according to another embodiment.

In some embodiments, the coupler 140 may be a tubular element disposed around the distal end of the actuation element 208 and the coupling portion 110 of the grasping device 104 to operably couple the actuation element 208 with the grasping device 104. In some embodiments, the coupler 140 is a hypotube. As shown in FIGS. 25A-25C, the coupler 140 may be disposed at least partially around the distal end of the actuation element 208 (FIG. 25A). The coupler 140 may be fixed to the actuation element 208 via a swage, such as a swaging the inner surface of the coupler 140 to the actuation element 208. The coupler 140 may also be crimped or welded to the actuation element 208. In other embodiments, the coupler 140 is a flexible wire, such as a spiral wire or coil, such as a stainless steel or Nitinol wire. The coupling portion 110 of the grasping device 104 may be inserted into distal end of the coupler 140 and the coupler 140 may be operably secured with the coupling portion 110 of the grasping device 104. The distal end of the coupler 140 may be connected, such as via a crimp, distally to the proximal end of grasping device 104 (FIG. 25B) such that the grasping device 104 is coupled with the actuation element 208 via the coupler 140, such as to maneuver the grasping device 104 to grasp tissue.

The coupler 140 may operably decouple the grasping device 104 from the actuation element 208, such as after the grasping device 104 has been maneuvered to grasp tissue. The actuation element 208 may be retracted proximally with sufficient force to break or otherwise disrupt the connection, such as the crimp, between the grasping device 104 and the coupler 140. When the connection between the grasping device 104 and the coupler 140 is broken or disrupted, the grasping device 104 may be decoupled from the actuation element 208 and the coupler 140 (FIG. 25C). The coupler 140 may remain coupled to the actuation element 208. For example, the grasping device 104 may be graspingly inserted into tissue and the actuation element 208 may be proximally retracted, such as via the actuation assembly 200, to break the connection between the grasping device 104 and the coupler 140. The force required to decouple the connection may be greater than the force required to pull the grasping device 104 out of the tissue. After the connection has been broken, the actuation element 208 and the coupler 140 may be retracted proximally from the grasping device 104, such as with the grasping device 104 graspingly inserted into the tissue. For example, the grasping devices 104 may be locked into position in the shroud 170 and the connection between the grasping device 104 and the actuation element 208 may be broken or otherwise disrupted such that the actuation element 208 may be decoupled from the grasping device 104 and the grasping device 104 may remain locked in the retracted position in the shroud 170.

Figure 26A:
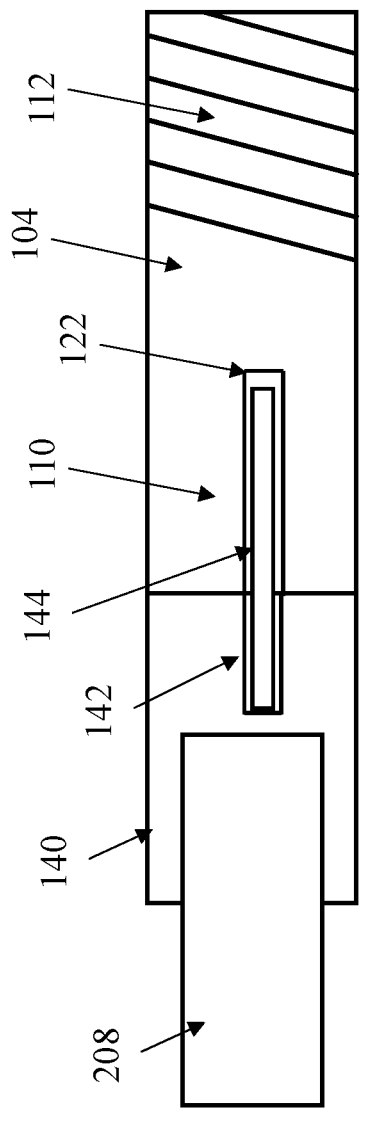
FIGS. 26A and 26B are schematic illustrations showing an actuation element coupled to and decoupled from a grasping device via a coupler according to another embodiment.
Figure 26B:
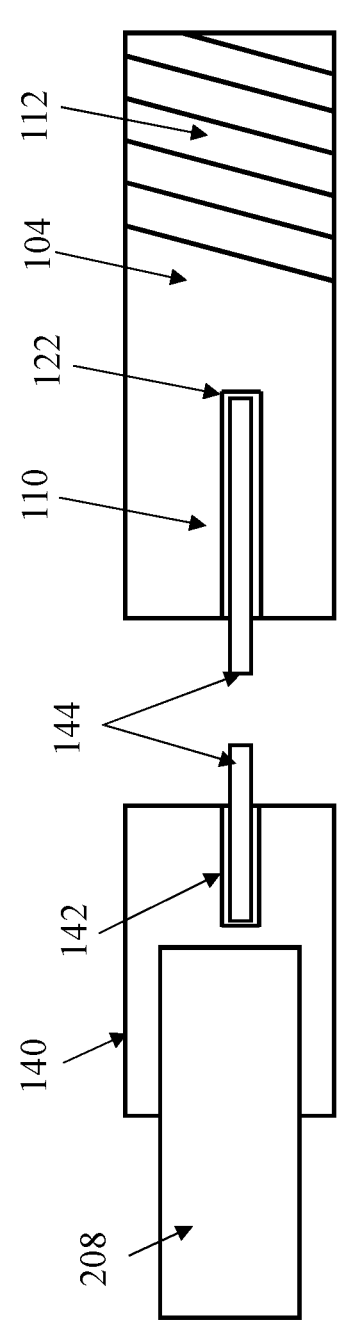

As shown in FIGS. 26A-26B, the coupler 140 is substantially cylindrical and is fixed to the distal end of the actuation element 208. In some embodiments, the coupler 140 may be welded to the distal end of the actuation element 208. The coupler 140 includes a distal channel 142 extending proximally from the distal end of the coupler 140. A coupling link 144 extends into and is secured in the distal channel 142. The distal end of the coupling link 144 may extend into and be secured in the receiving portion 122 of the grasping device 104. When secured, the coupling link 144 may operably couple the actuation element 208 to the grasping device 104. In some embodiments, the coupling link 144 is laser welded into the distal channel 142 of the coupler 140 and the receiving portion 122 of the grasping device 104.

The coupling link 144 may be sized, shaped, and configured such that movement and rotation of the actuation element 208 is translated to the grasping device 104 when the coupling link 144 couples the coupler 140 and the grasping device 104. The coupling link 144 may also be sized, shaped, and configured such that it breaks when subjected to a desired tensile load, such as the force applied to the coupling link 144 when the grasping device 104 is deployed in tissue and the actuation element 208 is proximally retracted. The force required to break the coupling link 144 may be greater than the force required to pull the grasping device 104 out of the tissue. In some embodiments, the coupling link 144 may have a width or diameter between about 0.003 inches and about 0.020 inches, such as between about 0.006 inches and about 0.010 inches. For example, after the grasping device 104 has been maneuvered to grasp tissue, the actuation element 208 may be retracted, such as via the actuation assembly 200, with sufficient force to break the coupling link 144 (FIG. 26B) such the coupling link 144 no longer couples the coupler 140 and the grasping device 104 and such that the coupler 140 and actuation element 208 may be retracted from the grasping device 104. In some embodiments, the coupling link 144 comprises stainless steel or Nitinol, or combinations thereof. In some embodiments, the coupling link 144 has a diameter between about 0.001 inches and about 0.006 inches. Further, the coupler 140 may include a sheath or coating on the coupling link 144 to reduce torsional loads on the coupling link 144 and to prevent the coupling link 144 from breaking prematurely.

Figure 27A:
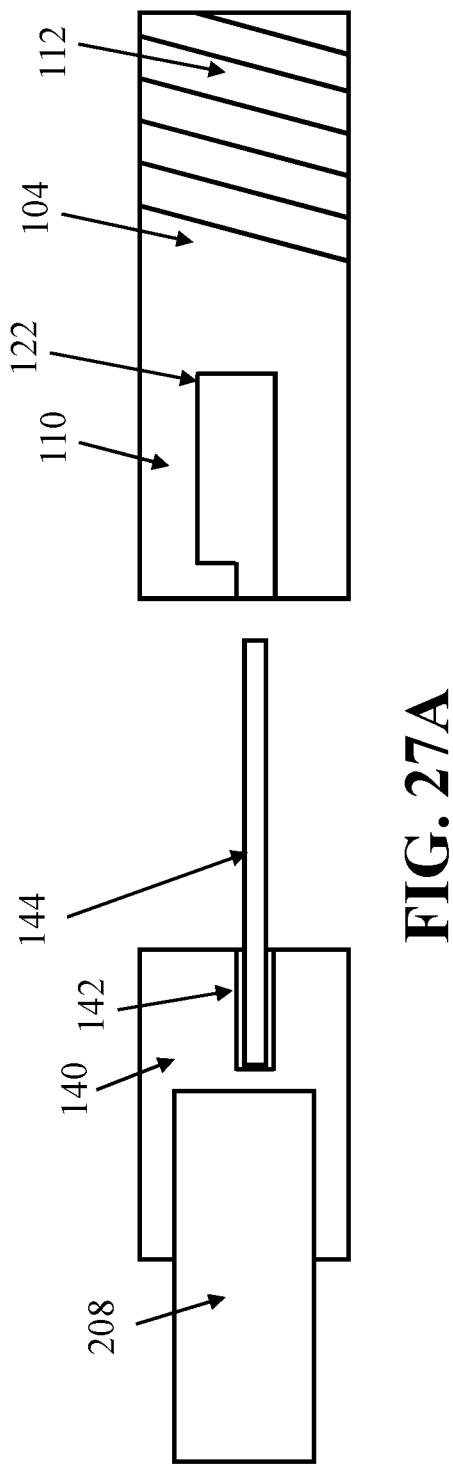
FIGS. 27A and 27B are schematic illustrations showing an actuation element coupled to and decoupled from a grasping device via a coupler according to another embodiment.
Figure 27B:
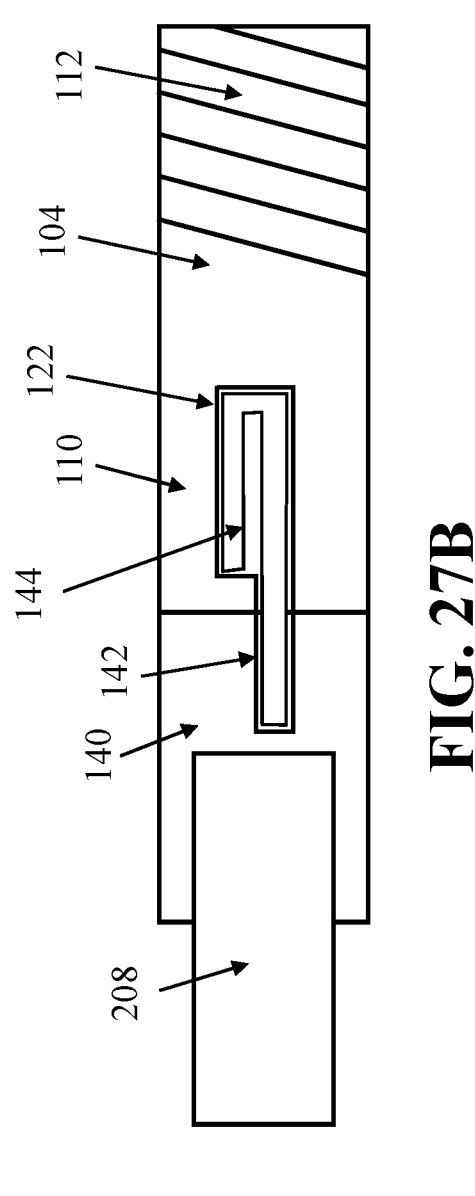
Figure 28A:
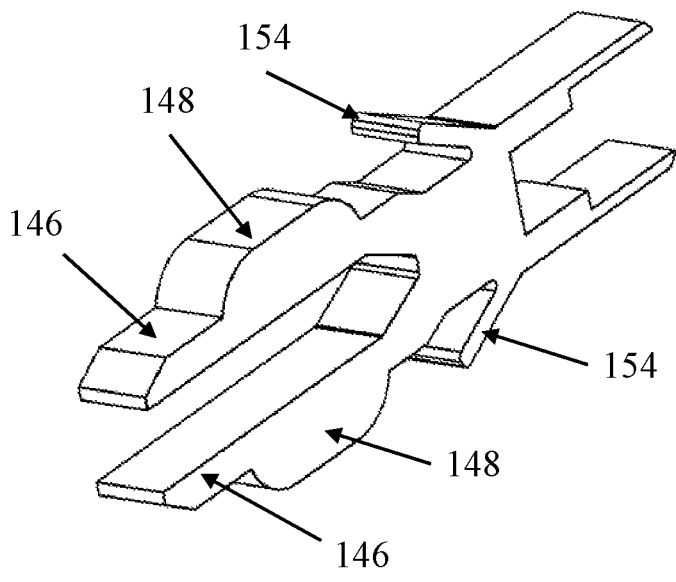
FIG. 28A is a perspective view of a coupler according to one embodiment.
Figure 28B:
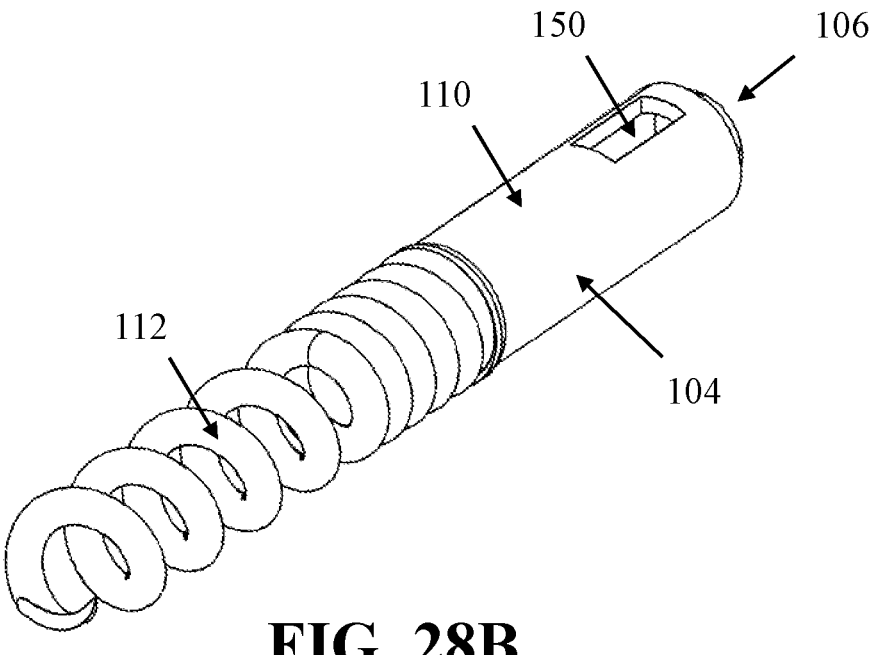
FIG. 28B is a perspective view of a grasping device configured to operably couple with the coupler of FIG. 28A.
Figure 28C:
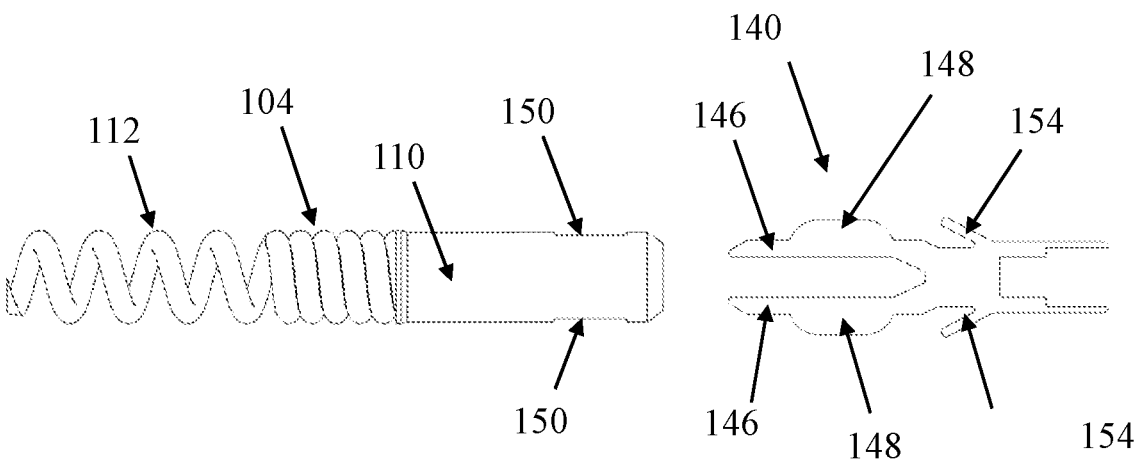
FIGS. 28C and 28D show various views of the coupler of FIG. 28A coupling with the grasping device of FIG. 28B.
Figure 28D:
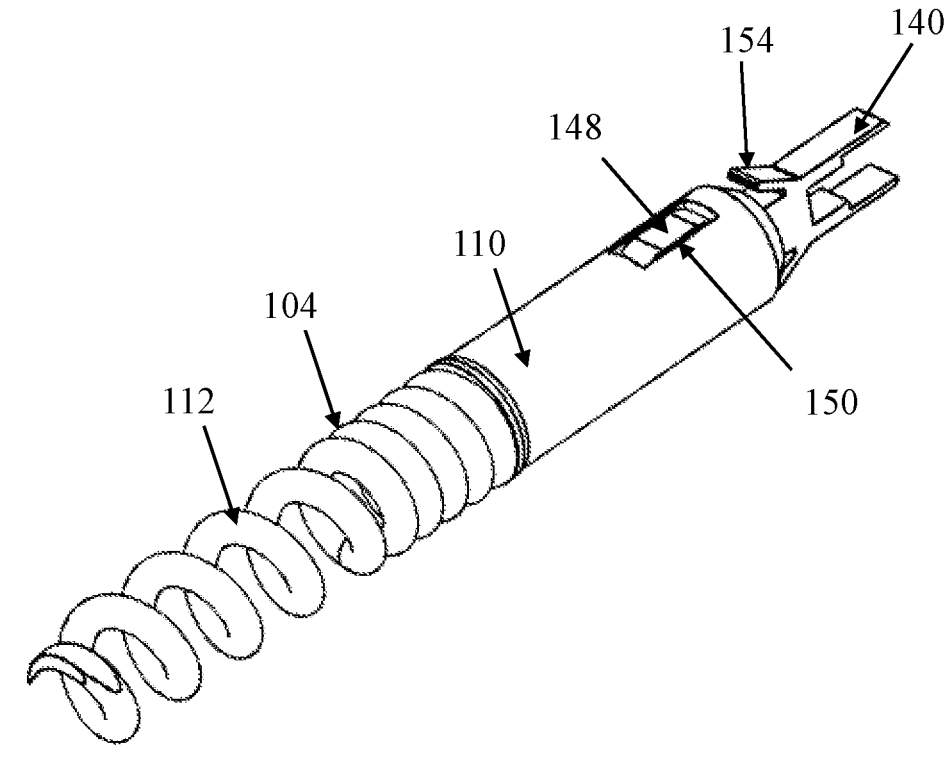

As shown in FIGS. 27A-27B, the coupler 140 may be substantially similar to the coupler 140 of FIGS. 26A-26B (above) with the proximal end of a coupling link 144 secured in the distal channel 142 of the coupler 140. The receiving portion 122 of the grasping device 104 may have a proximal opening that is narrower than the distal portion of the receiving portion 122. The coupling link 144 may be deformable such that the coupling link 144 may be inserted into the receiving portion 122 of the grasping device 104 and operably retained in the receiving portion 122 of the grasping device 104. For example, the coupling link 144 may be inserted into the proximal opening of the receiving portion 122 and may bend or otherwise deform in the receiving portion 122 such that the coupling link 144 has a width greater than the proximal opening of the receiving portion 122 thereby preventing the coupling link 144 from being retracted from the receiving portion 122 during ordinary operation. The coupling link 144 may be a shape memory material, such as Nitinol, such that the coupling link 144 remains in the deformed state without fracturing when inserted into the receiving portion 122.

During operation, the actuation element 208 may be controlled, such as via the actuation assembly 200, to deploy the grasping device 104. The coupling link 144 may be configured to translate the rotational and translational movements of the actuation element 208 to the grasping device 104. For example, the actuation element 208 may be positioned and rotated such that the grasping device 104 is deployed in the tissue. After the grasping device 104 has been deployed, the actuation element 208 may be proximally retracted with sufficient force to pull the coupling link 144 out of the deformed state such that the coupling link 144 may be retracted from the receiving portion 122. The force required to remove the coupling link 144 from the receiving portion 122 may be greater than the force required to pull the grasping device 104 out of the tissue. The actuation element 208 and the coupler 140 may then be retracted proximally from the grasping device 104, such as with the grasping device 104 deployed in the tissue and locked in the shroud 170.

In some embodiments, the coupler 140 may be configured to be operably inserted into the receiving portion 122 of the grasping device 104 and biased into coupling engagement with the grasping device 104 such that the actuation element 208 is operably coupled with the grasping device 104. As shown in FIGS. 28A-28D, the coupler 140 may include two or more prongs 146 extending distally from the remainder of the coupler 140, such as from the proximal portion of the coupler 140 which couples to the actuation element 208 (not shown). The prongs 146 are configured to be inserted into the receiving portion 122 (FIG. 10) of the grasping device 104 to operably couple the coupler 140 with the grasping device 104. The prongs 146 may be shaped and configured to bias radially outwardly in a normal state and such that the prongs 146 may be compressed radially inwardly, such as to insert the prongs 146 into the receiving portion 122. In some embodiments, the coupler 140 comprises a shape memory material, such as Nitinol, that is laser cut into the desired shape. In some embodiments, the proximal end of the coupler 140 is welded to the distal end of the actuation element 208.

The prongs 146 may be compressed together and inserted into the receiving portion 122 of the grasping device 104. After insertion, the compressive force may be released such that the prongs 146 pivot radially outwardly. The radially outward bias of the prongs 146 may retain the prongs 146 in the receiving portion 122 to operably couple the coupler 140 with the grasping portion 112. The prongs 146 may be disposed in the receiving portion 122 of the grasping device 104 such that the position and rotation of the grasping device 104 may be controlled by the actuation element 208 via the coupler 140, such as via the outward bias of the prongs 146 against the receiving portion 122.

The prongs 146 may also be operable to decouple the coupler 140 from the grasping device 104, such as after the grasping device 104 has been maneuvered to grasp tissue. For example, the prongs 146 of the coupler 140 may be compressed such that the prongs 146 may be retracted from the receiving portion 122 of the grasping device 104. After the grasping device 104 has been maneuvered to grasp tissue, the actuation element 208 may be proximally retracted with sufficient force to compress the prongs 146 of the coupler 140 against the proximal opening of the receiving portion 122 such that the prongs 146 may be withdrawn from the receiving portion 122. The compressed prongs 146 of the coupler 140 may be retracted from the receiving portion 122 to decouple the coupler 140 and the grasping device 104. The force required to retract the prongs 146 from the receiving portion 122 may be greater than the force required to pull the grasping device 104 out of the tissue. After the coupler 140 is decoupled from the grasping device 104, the actuation element 208 and the coupler 140 may be retracted from the grasping device 104, such as with the grasping device 104 deployed in the tissue and locked in the shroud 170.

In some embodiments, the coupler 140 includes one or more projections 148 extending radially outwardly from an outer side or edge (top or bottom) of one or more of the prongs 146. The projections 148 are each configured to be received in a detent 150 extending radially outwardly from the inner surface of the receiving portion 122 of the grasping device 104. The detents 150 may be depressions, slots, or apertures configured to receive the projections 148 of the prongs 146. In the illustrated embodiment, the detents 150 extend through the body of the grasping device 104. When the prongs 146 are inserted into the receiving portion 122 of the grasping device 104, the projections 148 may bias radially outwardly into the detents 150 of the receiving portion 122, further locking the prongs 146 into place in the receiving portion 122. The projections 148 may be configured to prevent the prongs 146 from translating or rotating from the coupling position with the grasping device 104 when the projections 148 are disposed in the detents 150. For example, the detents 150 may have a shape or cross-section substantially similar to the shape or cross-section of the projections 148 such that the projections 148 are prevented from translating or rotating within the detents 150 when the projections 148 are disposed in the detents 150. To decouple the coupler 140 from the grasping device 104, the actuation element 208 may be proximally retracted with sufficient force to compress the prongs 146 such that the projections 148 are retracted from the detents 150 such that the prongs 146 may be withdrawn from the receiving portion 122.

Figures 29A, 29B:
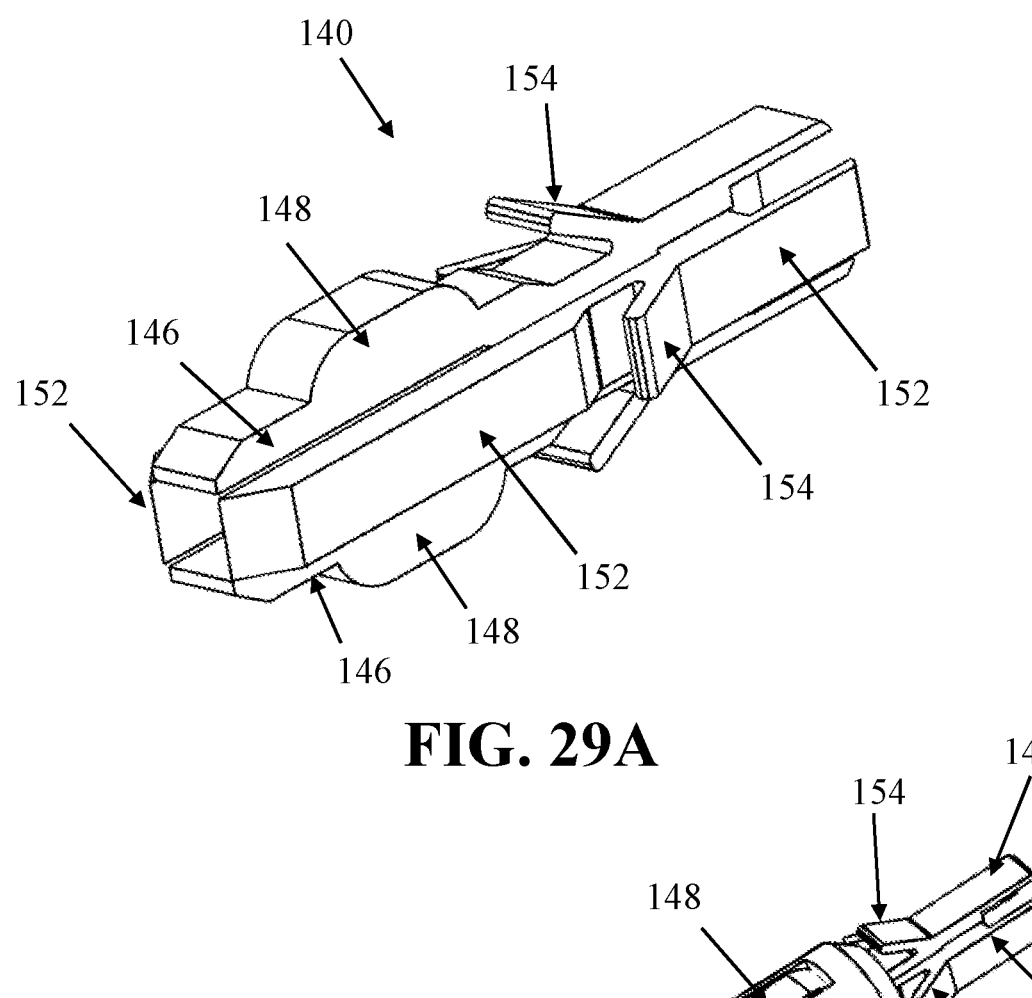
FIG. 29A is a perspective view of a coupler according to another embodiment.
FIG. 29B is a perspective view of the grasping device of FIG. 28B coupled the coupler of FIG. 29A.

As shown in FIGS. 29A-29B, the coupler 140 of FIGS. 28A-28D may include one or more guide arms 152 configured to further secure the coupler 140 in the receiving portion 122 of the grasping device 104. The guide arms 152 may be disposed on the lateral sides of the prongs 146 and may operate similarly to the prongs 146. For example, the guide arms 152 may be configured to bias radially outwardly to further couple the coupler 140 in the receiving portion 122 and/or to contact the inner surface of the receiving portion 122, such as perpendicularly to the prongs 146. The guide arms 152 may be inserted into the receiving portion 122 and may abut the inner surface of the receiving portion 122 to retain the coupler 140 in the receiving portion 122. The guide arms 152 ensure a better coupling between the coupler 140 and the grasping device 104. The guide arms 152 may remain coupled to the grasping device 104 when the grasping device 104 and/or the coupler 140 are put under a load or subjected to an external force. For example, the guide arms 152 may prevent the connection between the coupler 140 and the grasping device 104 from snapping or otherwise breaking during operation. The guide arms 152 may also increase the stability of the coupling between the grasping device 104 and the actuation element 208. The guide arms 152 may be retracted from the receiving portion 122 similarly to the prongs 146. For example, the guide arms 152 may be similarly compressed via proximal movement of the actuation element 208 such that the coupler 140 may be retracted from the receiving portion 122. In some embodiments, the guide arms 152 may also include projections 148 which engage with detents 150 of the grasping device 104.

In some embodiments, the coupler 140 of FIGS. 28A-28D or the coupler 140 of FIGS. 29A-29B may include flanges 154 configured to guide the grasping device 104 during coupling and operation and to prevent the grasping device 104 from sliding proximally beyond the coupler 140. The flanges 154 may extend distally and radially outwardly from the remainder of the coupler 140. The flanges 154 may be operable to abut the proximal end of the grasping device 104 to prevent the coupler 140 from extending further into the receiving portion 122, such as to prevent the coupler 140 from moving to a position in which the projections 148 cannot move out of the detents 150. The flanges 154 may also stabilize the coupler 140 during operation, such as by preventing wobbling at the coupling between the grasping device 104 and the actuation element 208 and keeping the grasping device 104 concentric with the actuation element 208. The flanges 154 may also be configured to cause the prongs 146 and/or the guide arms 152 to compress such that the coupler 140 may be decoupled from the grasping device 104, as described below. The proximal and distal ends of the flanges 154 may be rounded or tapered such that the flanges 154 to facilitate the coupling and decoupling of the coupler 140 and the grasping device 104.

While the couplers 140 have been described as operably coupling an actuation element 208 to a grasping device 104 with helical coils 114, it will be understood that any of the couplers 140 or coupling methods described herein may be used with any of the grasping devices 104 described herein. For example, couplers 140 and coupling methods described above may be used to operably couple an actuation element 208 to the grasping device 104 with a movable jaw 113 of FIG. 6.

In some embodiments, the shroud 170 may be operably coupled to the distal end of the catheter 302 such that the shroud 170 may be decoupled from the catheter 302. For example, the shroud 170 may be operably coupled to the distal end of the catheter 302 such that the shroud 170 may be decoupled from the catheter 302 after the grasping devices 104 have been maneuvered to grasp tissue and recruited into the tissue recruitment area 172 of the shroud 170, such as to keep the grasping devices 104 in position to close the defect and such that the catheter sheath assembly 300 and actuation elements 208 may be retracted from the body.

Referring now to FIGS. 30-34B, the tissue recruiting assembly 102 may include a connector 180 configured to operably couple the shroud 170 with the catheter 302. The connector 180 may couple the shroud 170 to the catheter 302 while the grasping devices 104 are maneuvered to grasp tissue and subsequently retracted toward or into the tissue recruitment area 172. The connector 180 may also decouple the shroud 170 from the catheter 302 after the grasping devices 104 have been recruited toward or into the tissue recruitment area 172, such as to keep the grasping devices 104 retracted into the shroud 170 to maintain the closure of the defect.

Figure 30A:
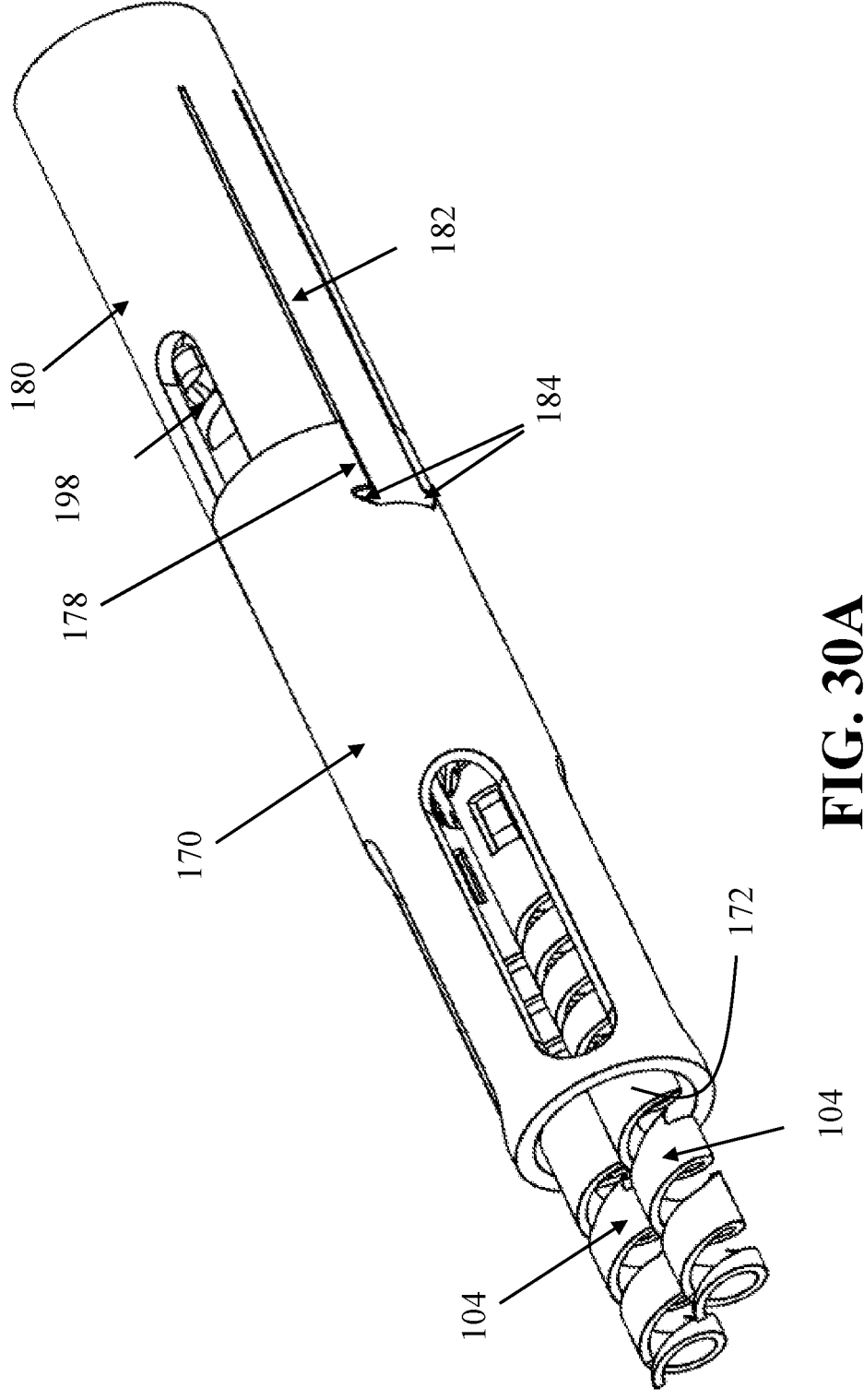
FIGS. 30A and 30B are perspective views showing a shroud coupled with a connector.
Figure 30B:
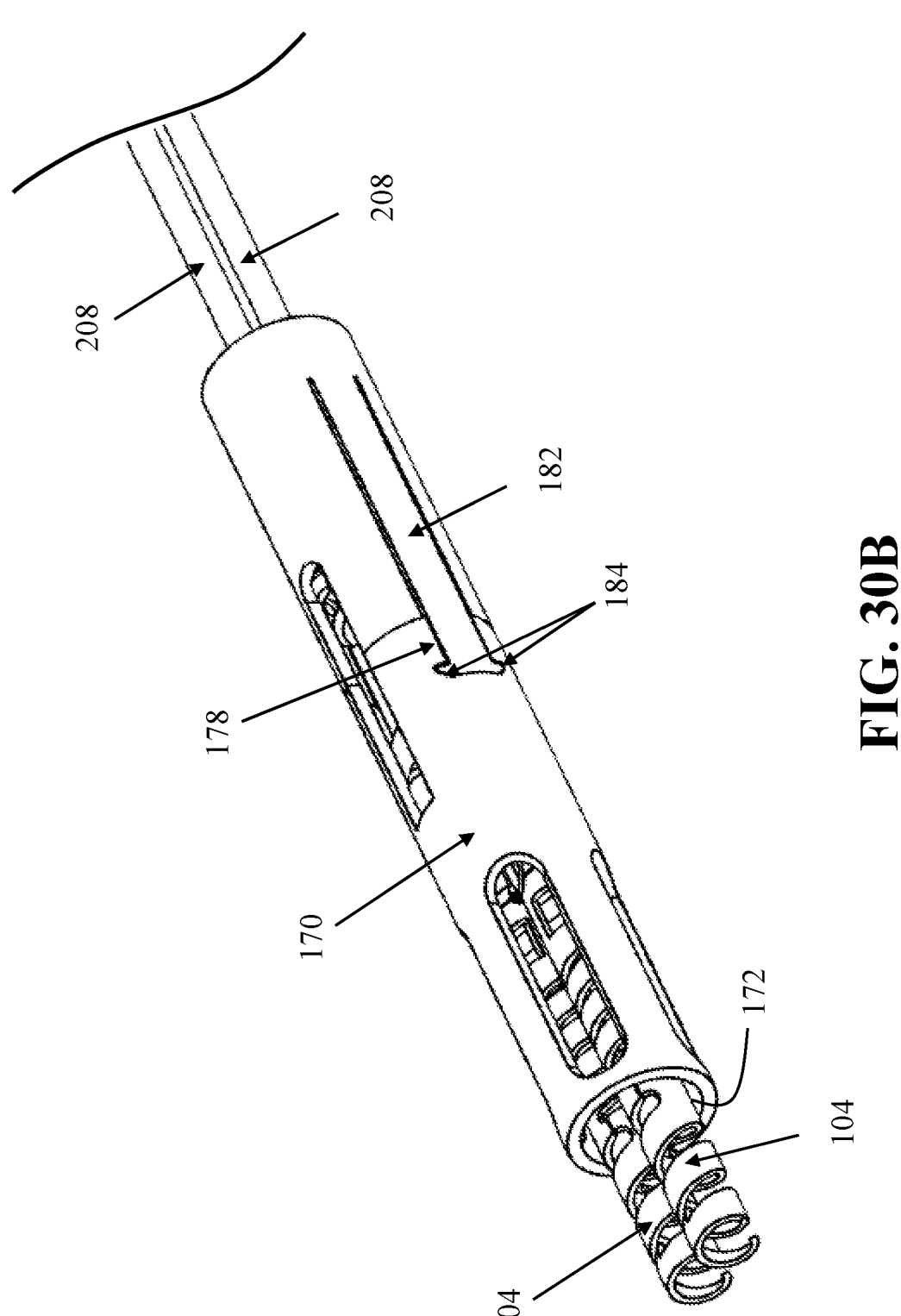

As shown in FIGS. 30A-30B, the connector 180 includes one or more connecting projections 182 operable to couple the connector 180 to the shroud 170. The connecting projections 182 extend distally from the remainder of the connector 180 and are operably received in corresponding connecting slots 178 of the shroud 170 to couple the shroud 170 to the connector 180. The shroud 170 may be translated and rotated with the catheter 302 when the connecting projections 182 are coupled with the connecting slots 178. In some embodiments, each connecting projection 182 includes lateral flanges 184 extending laterally from the distal end of the connecting projection 182 to retain the connecting projection 182 in the corresponding connecting slot 178 during operation. The proximal end of the connector 180 may be fixed to the distal end of the catheter 302 (not shown). In some embodiments, the connector 180 is welded to the distal end of the catheter 302.

The connecting projections 182 may be decoupled from the connecting slots 178 to decouple the shroud 170 from the connector 180, such as after the grasping devices 104 have been maneuvered to recruit tissue toward or into the tissue recruitment area 172 of the shroud 170 and the grasping devices 104 have been locked in the shroud 170. The connecting projections 182 may be flexed radially outwardly from the connecting slots 178, such as by flexing the connecting projections 182 such that the lateral flanges 184 are flexed radially outwardly from the connecting slot 178. For example, connecting projections 182 may be flexed radially outwardly via sufficient proximal retraction of the actuation elements 208, as described below. After the connecting projections 182 are flexed out of the connecting slots 178, the connector 180, the actuation elements 208, and catheter 302 may be retracted from the shroud 170 and the grasping devices 104, such as with the grasping devices 104 recruiting tissue to close a defect. Additionally, the tissue recruiting assembly 102 may include a release slider and a locking slider disposed within the shroud 170 and the connector 180 configured to decouple the grasping devices 104 from the actuation elements 208 and to decouple the connector 180 from the shroud 170, such as described below.

Referring now to FIGS. 31A-34B and 32A-34B, the connector 180 may include a proximal connector portion 181 and a distal connector portion 183. The proximal end of the proximal connector portion 181 may be fixed to the distal end of the catheter 302. The proximal connector portion 181 may be coupled to the distal end of the catheter 302 via adhesives, welding, fasteners, or the like. In an exemplary embodiment, the proximal connector portion 181 is welded to the catheter 302. The distal end of the distal connector portion 183 is coupled to the shroud 170. For example, the distal end of the distal connector portion 183 may be coupled to the outer surface of the shroud 170 such that the grasping devices 104 may be extended from and retracted into the shroud 170. The distal connector portion 183 may be coupled to the shroud 170 via adhesives, heat bonding, welding, fasteners, or the like. In an exemplary embodiment, the distal connector portion 183 is heat bonded to the shroud 170. The proximal connector portion 181 may be operably coupled with the distal connector portion 183 to operably couple the shroud 170 with the catheter 302. The distal end of the proximal connector portion 181 has a geometry or configuration which may be coupled with and decoupled from the proximal end of the distal connector portion 183.

As shown in FIGS. 32A-32F, the proximal connector portion 181 and the distal connector portion 183 each include a connecting portion 186 with one or more connecting projection 182 and define one or more receiving areas 188. The connecting portion 186 the proximal connector portion 181 defines the distal end of the proximal connector portion 181 with the connecting projection 182 extending distally from the remainder of the proximal connector portion 181 and the receiving area 188 proximally inset from a portion of the connecting projection 182. The connecting portion 186 of the distal connector portion 183 defines the proximal end of the distal connector portion 183 with the connecting projection 182 extending proximally from the remainder of the distal connector portion 183 and the receiving area 188 distally inset from a portion of the connecting projection 182. The connecting projection 182 of the proximal connector portion 181 is configured to be received in the receiving area 188 of the distal connector portion 183 and the connecting projection 182 of the distal connector portion 183 is configured to be received in the receiving area 188 of the proximal connector portion 181. When the coupling pr of the proximal and distal connector portions 181, 183 are received in the receiving areas 188 of the other connector portion 181, 183 the proximal connector portion 181 may interlock with the distal connector portion 183 such that the connector portions 181, 183 may rotate and translate together. The shroud 170 is operably coupled to the catheter 302 when the proximal connector portion 181 is interlocked with the distal connector portion 183.

In some embodiments, the connecting projections 182 of the connector portions 181, 183 each include lateral flanges 184 extending laterally from the sides of the connecting projections 182 The lateral flanges 184 of the proximal connector portion 181 may extend laterally from the sides at the distal end of the connecting projection 182. The lateral flanges 184 of the distal connector portion 183 may extend laterally from the sides at the proximal end of the connecting projection 182. The lateral flanges 184 of the proximal connector portion 181 may interlockingly hook around the lateral flanges 184 of the distal connector portion 183 to further secure the coupling of the proximal and distal connector portions 181, 183.

The lateral flanges 184 of the proximal connector portion 181 may be disposed distally behind the lateral flanges 184 of the distal connector portion 183 when the connecting projection 182 of the proximal connector portion 181 is disposed in the receiving area 188 of the distal connector portion 183. The lateral flanges 184 of the distal connector portion 183 may be disposed proximally behind the lateral flanges 184 of the proximal connector portion 181 when the connecting projection 182 of the distal connector portion 183 is disposed in the receiving area 188 of the proximal connector portion 181. The overlap of the lateral flanges 184 may further secure the coupling between the proximal and distal connector portions 181, 183. In some embodiments, the lateral flanges 184 are arcuate such that the proximal and distal connector portions 181, 183 are substantially cylindrical when the proximal connector portion 181 is coupled with the distal connector portion 183.

The proximal connector portion 181 may be decoupled from the distal connector portion 183 such that the shroud 170 is decoupled from the catheter 302, such as to decouple the connecting portions 186 of the proximal and distal connector portions 181, 183. The connecting projection 182 of the proximal connector portion 181 may be moved out of the receiving area 188 of the distal connector portion 183 and/or the connecting projection 182 of the distal connector portion 183 may be moved out of the receiving area 188 of the proximal connector portion 181, such as via the actuation assembly 200, such that the proximal connector portion 181 may be decoupled from the distal connector portion 183. Additionally or alternatively, the proximal connector portion 181 may be decoupled from the distal connector portion 183 by removing a component disposed within the proximal and distal connector portions 183 between the connecting portion 186 of the proximal and distal connector portions 181, 183, as described below. In some embodiments, the proximal connector portion 181 and/or the distal connector portion 183 are configured to decouple via proximal retraction of one or more actuation elements 208, as described below. When the proximal connector portion 181 is decoupled from the distal connector portion 183, the catheter 302, actuation elements 208, and proximal connector portion 181 may be withdrawn from the shroud 170 and the grasping devices 104, such as with the grasping devices 104 recruiting tissue to close a defect.

In some embodiments, the proximal connector portion 181 is sized, shaped, and configured to further secure the proximal connector portion 181 to the distal end of the catheter 302. In some embodiments, the proximal end of the proximal connector portion 181 is coupled with the distal end of the catheter 302 by fitting the proximal end of the proximal connector portion 181 to a polymer dual lumen extrusion flowing a melted polymer, such as thermoplastic material, around coupling between the proximal connector portion 181 and the catheter 302.

Figure 33A:
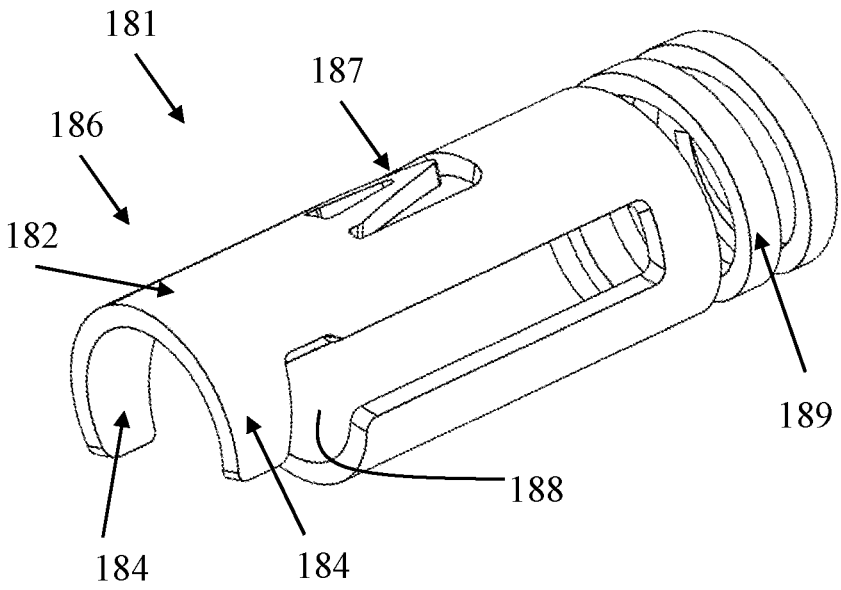
FIGS. 33A and 33B are front and rear perspective views of a proximal connector portion according to another embodiment.
Figure 33B:
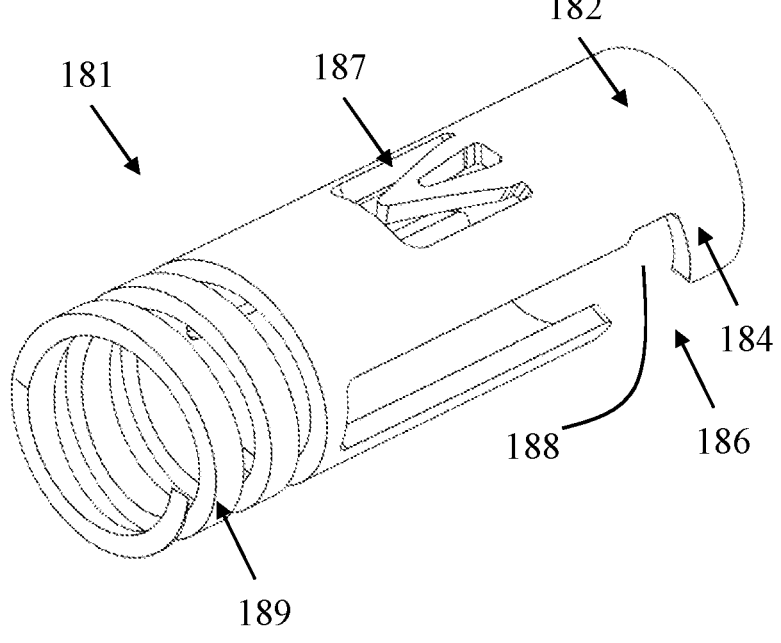

In some embodiments, as shown in FIGS. 33A-33B, the proximal portion of the proximal connector portion 181 includes a coil 189 configured to further secure the proximal connector portion 181 to the catheter 302. The coil 189 extends proximally from the remainder of the proximal connector portion 181 (e.g., opposite the connecting portion 186) in a substantially helical or spiral manner. The coil 189 may reduce strain on the coupling of the catheter 302 and the proximal connector portion 181, such as to allow slight bending of the connection between the catheter 302 and the proximal connector portion 181. The coil 189 may be laser cut to form a spiral or corkscrew. The proximal connector portion 181 may be connected to the distal end of the catheter 302 with melted polymer applied to the catheter 302. For example, when the polymer is applied to the proximal connector portion 181 and/or the catheter 302, the polymer may melt into the gaps between the coil 189. In some embodiments, the proximal connector portion 181 includes one or more struts in the gaps between the coil 189 and extending longitudinally to connect adjacent portions of the coil 189. The struts between the spirals of the coil 189 may space the spirals of the coils 189 apart, such as to minimize or otherwise reduce the spring or biasing effect of the coil 189.

Alternatively, a helical spring may be disposed around a distal portion of the catheter 302 and the proximal end of the proximal connector portion 181 may be secured to the spring, such as via welding. The spring may be sleeved underneath the polymer applied to the catheter 302.

Figure 34A:
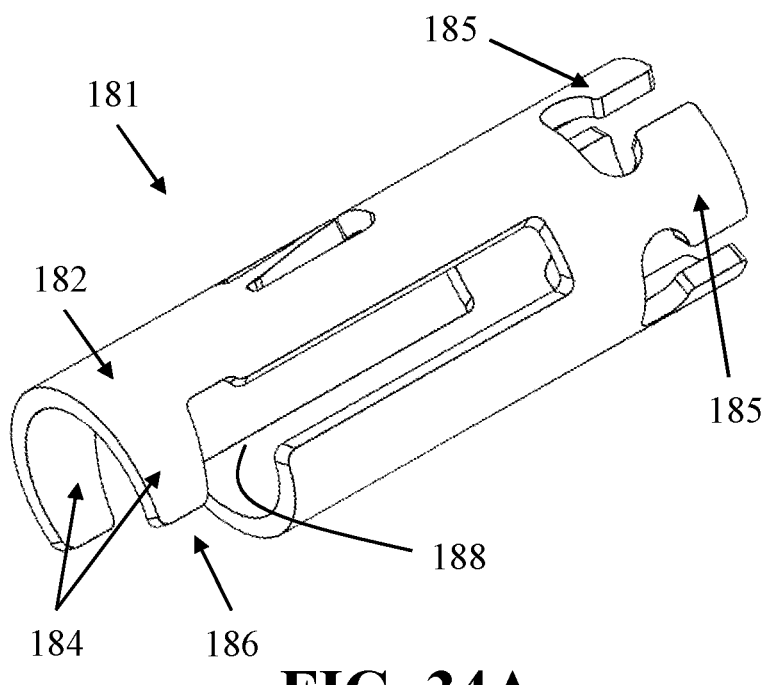
FIGS. 34A and 34B are front and rear perspective views of a proximal connector portion according to another embodiment.
Figure 34B:
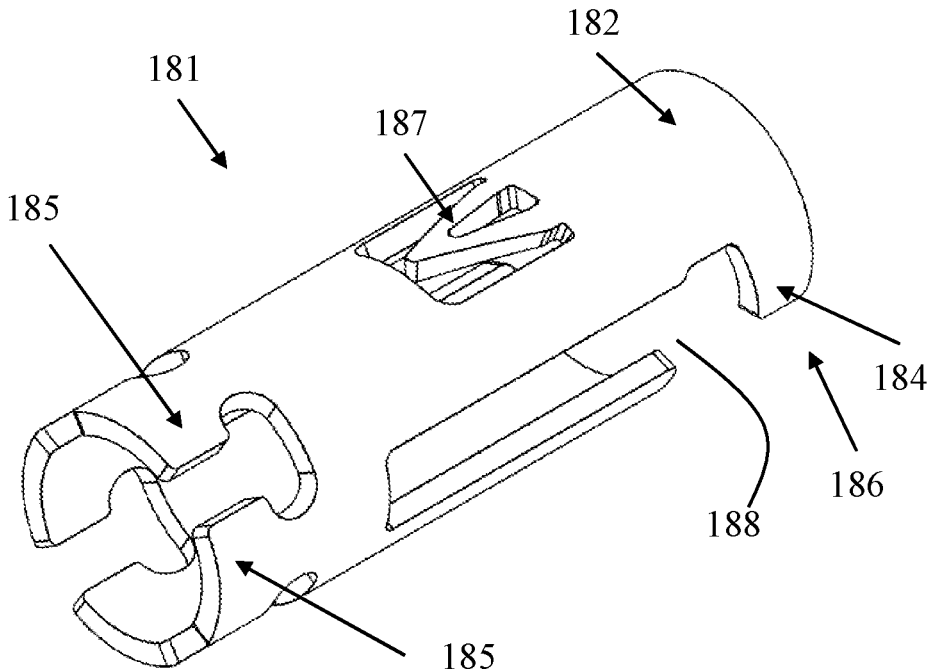
Figure 35:
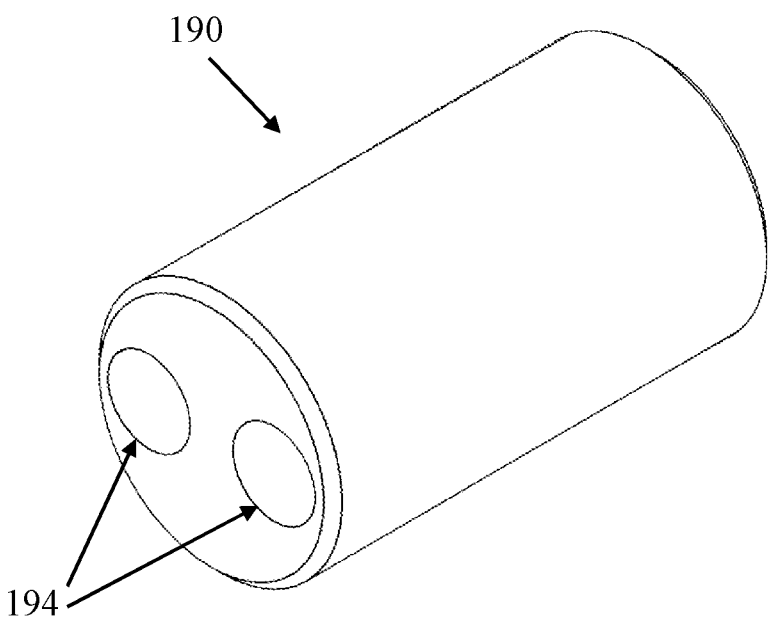
FIG. 35 is a front perspective view of a lock slider of the tissue recruitment assembly of FIG. 31A.
Figure 36:
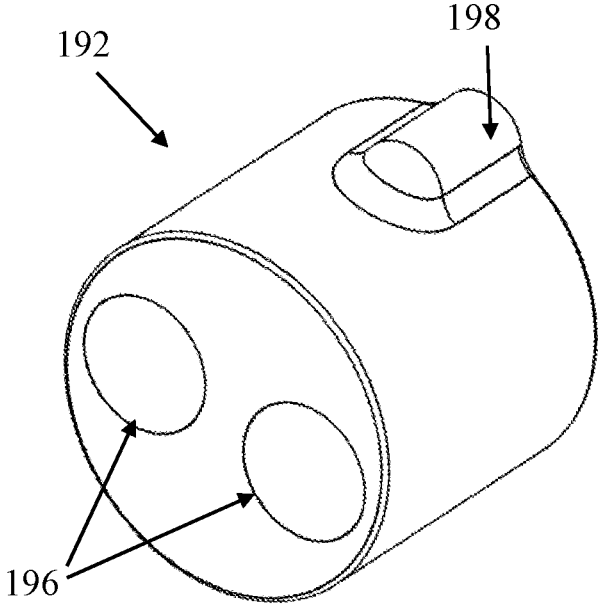
FIG. 36 is a front perspective view of a release slider of the tissue recruitment assembly of FIG. 31A.

Additionally or alternatively, the proximal end of the proximal connector portion 181 may include other features or configurations to further secure the proximal connector portion 181 to the distal end of the catheter 302. As shown in FIGS. 34A-34B, the proximal end of the proximal connector portion 181 may include one or more flared tabs 185 disposed around the circumference of the proximal connector portion 181. When the polymer is applied to the proximal connector portion 181 and/or the catheter 302, the polymer may melt into the gaps between the flared tabs 185 and around the flared tabs 185, such as to further secure the proximal connector portion 181 to the catheter 302. The proximal end of the proximal connector portion 181 may also include a plurality of apertures disposed around the circumference of the proximal connector portion 181 to similarly strengthen the coupling between the proximal connector portion 181 and the catheter 302.

While the proximal connector portion 181 has been described as being coupled to the catheter 302 via a polymer, it will be understood that the proximal connector portion 181 may be coupled to the catheter 302 in other manners. For example, in some embodiments, the proximal connector portion 181 may be welded to the distal end of the catheter 302. Further, the features of the proximal connector portion 181 may be incorporated into the distal end of the catheter 302 and/or the features of the distal connector portion 183 may be incorporated into the proximal end of the shroud 170.

The tissue recruiting assembly 102 may include one or more components configured to operably control the coupling of the proximal and distal connector portions 181, 183 and/or to operably control the coupling of the grasping devices 104 with the actuation elements 208. For example, FIGS. 31B-31C shows the tissue recruiting assembly 102 with the proximal and distal connector portions 181, 183 removed.

As shown in FIGS. 31B-31C and 35-37B, the tissue recruiting assembly 102 may include a release slider 190 slidably disposed along the actuation elements 208 and a release member 192 disposed around along the actuation elements 208 distally from the release slider 190. The release slider 190 may be disposed along the actuation elements 208 proximally to the release member 192. The release slider 190 may be operable to maintain the coupling of the proximal and distal connector portions 181, 183, and to operably decouple the proximal and distal connector portions 181, 183, such as after the grasping devices 104 have grasped tissue and been retracted into the locked position. The release member 192 may be operable to decouple the grasping devices 104 from the actuation elements 208, such as to decouple the grasping devices 104 from the couplers 140. The release member 192 may also be operable to maintain the position and rotation of the grasping devices 104 in the locked position. The release slider 190 and the release member 192 may comprise a polymer, PEEK, ABS, ceramic, polymer, metal, or other plastics or metals operable to withstand the operational forces, or any combination thereof.

Figure 37A:
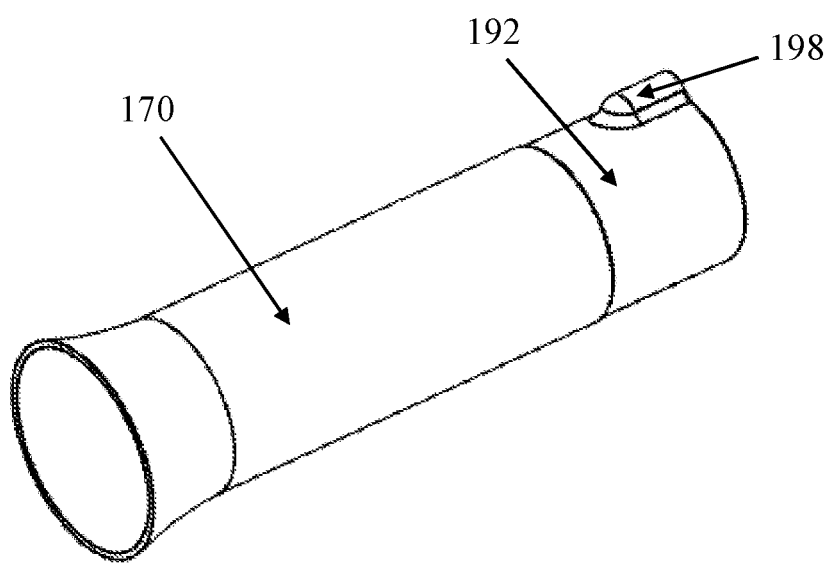
FIG. 37A is a front perspective view of the release slider of FIG. 36 coupled with a shroud.
Figure 37B:
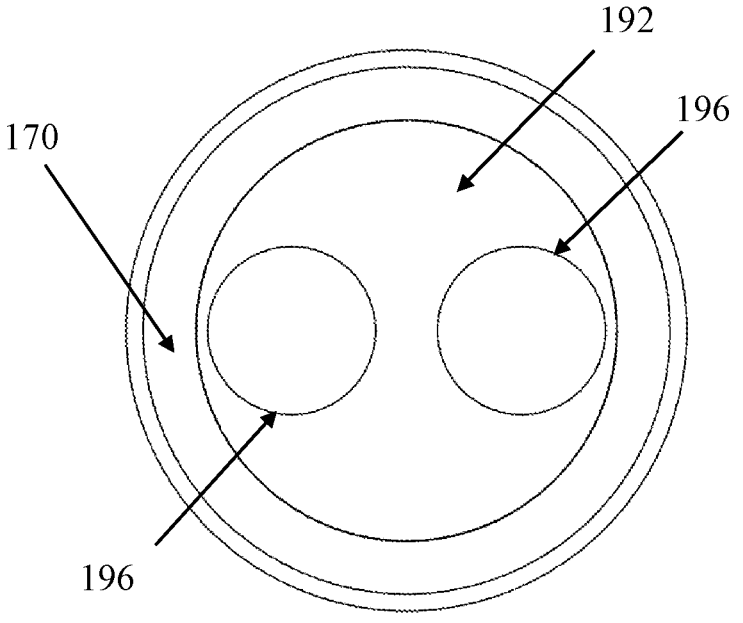
FIG. 37B is a front view of the release slider and shroud of FIG. 37A.

The position of the release member 192 may be fixed relative to the shroud 170 and/or the distal connector portion 183. The distal end of the release member 192 may be fixed to the proximal end of the shroud 170 and/or the inner surface of the distal connector portion 183 (FIGS. 37A-37B). For example, the release member 192 may be welded to the inner surface of the distal connector portion 183 (which is coupled with the shroud 170) such that the release member 192 is disposed at the proximal end of the shroud 170.

The release slider 190 may be relatively free sliding on the actuation elements 208 such that the actuation elements 208 may be extend through the release member 192 such that the actuation elements 208 may rotate and translate therethrough. During the tissue recruiting operation, the release slider 190 may be disposed along the actuation elements 208 and within the proximal and distal connector portions 181, 183 such that the release slider 190 maintains the coupling between the proximal and distal connector portions 181, 183. The release slider 190 may also be slidable within the proximal and distal connector portions 181, 183 such that release slider 190 no longer maintains the coupling between the proximal and distal connector portions 181, 183, thereby decoupling the proximal connector portion 181 from the distal connector portion 183.

The release slider 190 and release member 192 may both be substantially cylindrical. The release slider 190 may include two actuation passages 194 extending through the release slider 190 and each configured to receive an actuation element 208 therethrough. The release member 192 may include two release passages 196 extending through the release member 192 and each configured to receive an actuation element 208 therethrough. The actuation passages 194 of the release slider 190 may be sized, shaped, and configured to permit the actuation elements 208 to translate and rotate when disposed therein. The actuation passages 194 of the release slider 190 may also be sized, shaped, and configured to prevent the couplers 140 from extending therein. The actuation passages 194 may have a diameter or cross section which allows the actuation element 208 to translate and rotate therethrough and which prevents the couplers 140 from proximally extending therethrough, such as having a diameter greater than the diameter of the actuation elements 208 and less than a diameter of the couplers 140. For example, the actuation passages 194 of the release slider 190 may be sized, shaped, and configured to lockingly receive the proximal portions of the coupler 140 therein and to prevent the distal end of the couplers 140, such as the prongs 146 of the coupler 140 from inserting therein. Additionally or alternatively, the actuation passages 194 may be undersized such that the couplers 140 bend or flex to conform to the inner diameter of the actuation passages 194, such as to secure at least a portion of the couplers 140 in the actuation passages 194.

The release passages 196 of the release member 192 may be sized, shaped, and configured to operably decouple the grasping devices 104 from the couplers 140. The release passages 196 may be sized, shaped, and configured, to allow the couplers 140 to pass therethrough and to prevent the grasping device 104 from extending therethrough. For example, the release passages 196 may have a diameter or cross section greater than the diameter of the couplers 140 and less than the diameter of the grasping devices 104, such as a diameter less than a diameter of the coupling portion 110 of the grasping devices 104.

The release slider 190 and the release member 192 may be disposed around the actuation elements 208 and within the proximal and/or distal connector portions 181, 183. The actuation elements 208 may rotate and translate through the release slider 190 and the release member 192, such as to maneuver the grasping devices 104 during the tissue grasping operation. The release slider 190 and the release member 192 may have an outer surface slightly smaller than the inner diameters of the proximal and distal connector portions 181, 183. The outer surface of the release slider 190 may be sized such that the release slider 190 may slide within the inner surfaces of the proximal and distal connector portions 181, 183. The outer surface of the release member 192 may be sized such that the release member 192 may be fixed, such as via welding, within the distal connector portion 183.

During the tissue grasping operation, the release slider 190 may be disposed in an operational position within the connector 180 such that the release slider 190 maintains or otherwise prevents the proximal and distal connector portions 181, 183 from decoupling. The release slider 190 may be disposed within the proximal and distal connector portions 181, 183 such that the outer surface of the release slider 190 abuts the inner surfaces of the proximal and distal connector portions 181, 183. The outer surface of the release member 192 may abut the inner surfaces of the connecting portions 186 of the proximal and distal connector portions 181, 183 to prevent the proximal and distal connector portions 181, 183 from decoupling. For example, the outer surface of the release slider 190 may simultaneously abut the connecting portions 186 of the connector 180 to prevent the connecting projection 182 of the proximal connector portion 181 from moving out of the receiving area 188 of the distal connector portion 183 and to prevent the connecting projection 182 of the distal connector portion 183 from moving out of the receiving area 188 of the proximal connector portion 181.

The release slider 190 may also be slidable within the proximal and distal connector portions 181, 183 such that the release slider 190 may be moved out of the operational position. The release slider 190 may be proximally retracted from the operational position, such as by proximal retraction of the actuation elements 208, such that the release slider 190 no longer maintains the coupling of the proximal and distal connector portions 181, 183. When the release slider 190 is moved out of the operational position, the proximal connector portion 181 may be decoupled from the distal connector portion 183.

In some embodiments, the proximal connector portion 181 includes a retention tab 187 configured to operably retain the release slider 190 in the operational position to maintain the coupling between the shroud 170 and the catheter 302, such as to maintain the coupling between the proximal and distal connector portions 181, 183. The retention tab 187 may be bent or flexed radially inwardly to abut the proximal end of the release slider 190 when the release slider 190 is in the operational position. The abutment between the retention tab 187 and the release slider 190 may prevent the release member 192 from proximally retracting during the tissue grasping operation. The retention tab 187 may flex or bend radially outwardly when the release slider 190 is proximally retracted with sufficient force, such as via the actuation element 208, thereby allowing the release slider 190 to be proximally retracted.

Figures 38A, 38B:
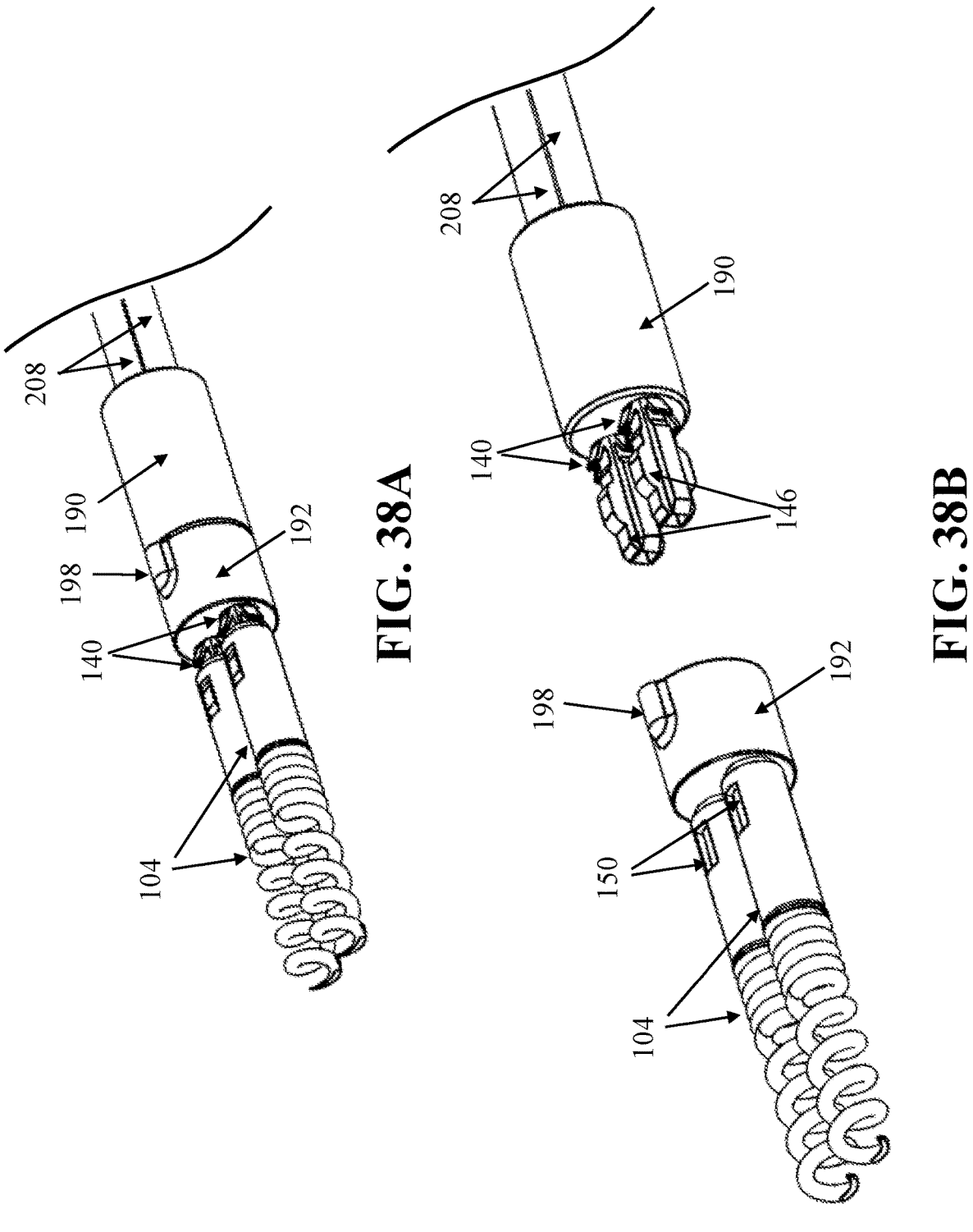
FIG. 38A is a perspective view of grasping devices in a locked position with the release and lock sliders of FIGS. 35 and 36.
FIG. 38B is a perspective view of the grasping devices of FIG. 38A decoupled from the couplers of FIG. 38A by the release and lock sliders of FIGS. 35 and 36.

The release member 192 is operable to decouple the grasping devices 104 from the actuation elements 208, such as to decouple the grasping devices 104 from the couplers 140, when the actuation elements 208 and grasping devices 104 are retracted a sufficient distance, such as via the actuation assembly 200. As shown in FIG. 38A, the actuation elements 208 and the grasping devices 104 may be proximally retracted into a locked position. The shroud 170, such as the proximal portion of the shroud 170, may narrowed such that the shroud 170 is operable to retain the positions of the grasping devices 104 in the fully retracted position, such as by applying a compression fit, an interference fit, and/or frictional force with the grasping devices 104, such as the coupling portions 110 of the grasping devices 104. The translational and rotational positions of the grasping devices 104 may be maintained when grasping devices 104 are locked in the shroud 170, such as to maintain the grasp of the grasping devices 104 on the target tissue.

The grasping devices 104 may be retracted into the shroud 170, such as when the grasping devices 104 are retracted into the locked position, such that the couplers 140 extend at least partially through the release passages 196 of the release member 192. The grasping devices 104 may be retained in the locked position such that the grasping portions 112 of the grasping devices 104 are distal to the release member 192. In some embodiments, the coupling portions 110 of the grasping devices 104 are distal to the release member 192 when the grasping devices 104 are in the locked position. In other embodiments, the coupling portions 110 of the grasping devices 104 extend at least partially into the release passages 196 of the release member 192 when the grasping devices 104 are in the locked position such that the release member 192 is operable to further retain the grasping devices 104 in the locked position. The release passages 196 may be sized, shaped, and configured to retain the position of the grasping devices 104 when the coupling portions 110 are at least partially disposed in the release passages 196. For example, the release passages 196 may comprise a polymer such that the release passages 196 conform to coupling portions 110 of the grasping devices 104 to retain the grasping devices 104 in the locked position.

As shown in FIG. 38B, the couplers 140 may be decoupled from the grasping devices 104 such that the grasping devices 104 are decoupled from the actuation elements 208, such as after the grasping devices 104 have been retracted into the locked position. The actuation elements 208 may be proximally retracted, such as via the actuation assembly 200, to proximally retract the actuation elements 208 through the release passages 196 of the release member 192. The proximal retraction of the actuation elements 208 may pull the couplers 140 proximally through the release passages 196 of the release member 192. The release member 192, such as the release passages 196, may be sized, shaped, and configured to prevent the grasping devices 104 from retracting through the release passages 196 with the actuation elements 208 and the couplers 140. For example, the distal end of the release member 192 may abut a portion of the grasping devices 104 to prevent the grasping devices 104 from being proximally retracted through the release passages 196.

The actuation elements 208 may be proximally retracted farther such that the couplers 140 are proximally retracted through the release passages 196 and decoupled from the grasping devices 104 which are prevented from proximally retracting via abutment with the release member 192. The actuation elements 208 may be proximally retracted with sufficient force to pull or otherwise decouple the couplers 140 from the receiving portions 122 of the grasping devices 104. For example, the actuation elements 208 may be retracted with sufficient force to proximally retract the prongs 146 of the couplers 140 from the receiving portions 122 of the grasping devices 104, as described above.

After the couplers 140 are decoupled from the grasping devices 104, the actuation elements 208, release slider 190, and couplers 140 may be retracted from the grasping devices 104 and release member 192 (and shroud 170), such as after the grasping devices 104 have grasped tissue and been recruited toward or into the tissue recruitment area 172 of the shroud 170, such as into the locked position. The force required to decouple the decouple the grasping devices 104 from the actuation elements 208 via the release member 192 may be greater than the force required to pull the grasping device 104 out of the tissue. In some embodiments, the force required to lock the grasping devices 104 in the shroud 170 is between about 4 pounds and about 5 pounds and the force required to decouple the grasping devices 104 from the actuation elements 208 is between about 3 pounds and about 6 pounds. The force required to lock each of the individual grasping devices 104 may be less than the force required to decouple the shroud 170 from the catheter 302. For example, the force required to lock the grasping devices 104 may be evenly distributed between the grasping devices 104 such that each grasping devices experiences between about 2.0 pounds and about 2.5 pounds of force.

The release slider 190 may be configured to decouple the shroud 170 from the catheter 302 via further proximal retraction of the actuation elements 208, such as after the grasping devices 104 have grasped and recruited tissue into the tissue recruitment area 172 of the shroud 170, been locked in position, and been decoupled from the actuation elements 208. The actuation element 208 may be retracted further proximally such that the distal end of the actuation element 208 and/or the couplers 140 abuts a distal surface of the release slider 190 and such that the distal end of the actuation element 208 and/or the couplers 140 are prevented from extending through the actuation passages 194. For example, the actuation element 208 may be retracted such that the prongs 146 of the coupler 140 abut the distal surface of the release slider 190 such that the prongs 146 are prevented from extending through the actuation passages 194. Additionally or alternatively, at least a portion of the couplers 140 may bend or flex within the actuation passages 194 to secure the couplers 140 in a portion of the actuation passages 194 such that the position of the couplers 140 is fixed relative to the release slider 190.

The actuation element 208 may then be retracted with sufficient proximal force that the abutment between the actuation element 208 and/or the couplers 140 and the release member 192 proximally retracts the release slider 190 from the operational position. The actuation element 208 may be retracted with sufficient force to flex the retention tab 187 radially outwardly such that release slider 190 may be proximally retracted with the actuation element 208. The release slider 190 may then be proximally retracted relative to the proximal and distal connector portions 181, 183. When the release slider 190 is proximally retracted from the operational position, the release slider 190 may no longer maintain the coupling of the proximal and distal connector portions 181, 183 such that the proximal and distal connector portions 181, 183 may be decoupled, such as to decouple the shroud 170 from the catheter 302. For example, the release slider 190 may be proximally retracted from beneath the connecting portions 186 of the proximal and distal connector portions 181, 183 such that the coupling between the proximal and distal connector portions 181, 183 is broken or otherwise disrupted. Additionally or alternatively, the catheter 302 may be maneuvered to pull the connecting projections 182 of the proximal connector portion 181 out of the receiving area 188 of the distal connector portion 183 to decouple the shroud 170 from the catheter 302. After the shroud 170 has been decoupled from the catheter 302, the tissue recruiting assembly 102 may be deployed in the body, such as with the tissue grasping devices 104 in the locked position and recruiting tissue into the tissue recruitment area 172 of the shroud 170, and the actuation elements 208 (and couplers 140), proximal connector portion 181, catheter 302, and release slider 190 may be withdrawn from the body.

While the release slider 190 has been described as releasably maintaining the coupling between the proximal and distal connector portions 181, 183, it will be understood that the release slider 190 may be similarly be operable in other configurations and assemblies of the tissue recruiting device 100. For example, the features of the connecting portion 186 of the distal connector portion 182 may be incorporated to the proximal end of the shroud 170 and the features of the connecting portion 186 of the proximal connector portion 181 may be incorporated into the distal end of the catheter 302. The release slider 190 may be disposed beneath the coupling of the catheter 302 and the shroud 170 during operation to maintain the coupling between the catheter 302 and the shroud 170 and the release slider 190 may be proximally retracted after the tissue recruiting operation to decouple the catheter 302 from the shroud 170.

Figure 31A:
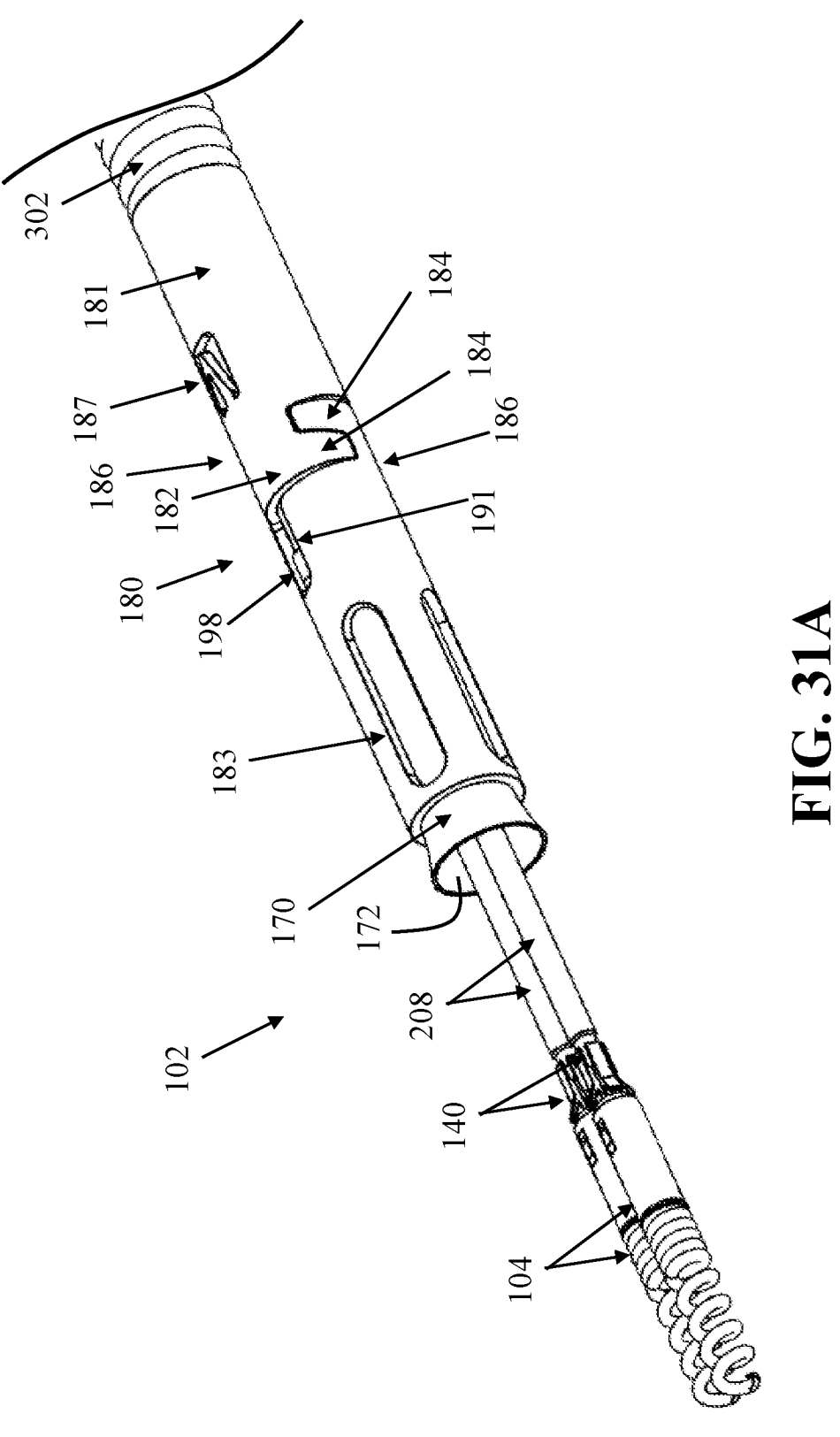
FIG. 31A is a perspective view of a tissue recruiting assembly according to one embodiment coupled to catheter.
Figure 31B:
FIG. 31B is a perspective view of the tissue recruiting assembly of FIG. 31A with the connector removed.
Figure 31C:
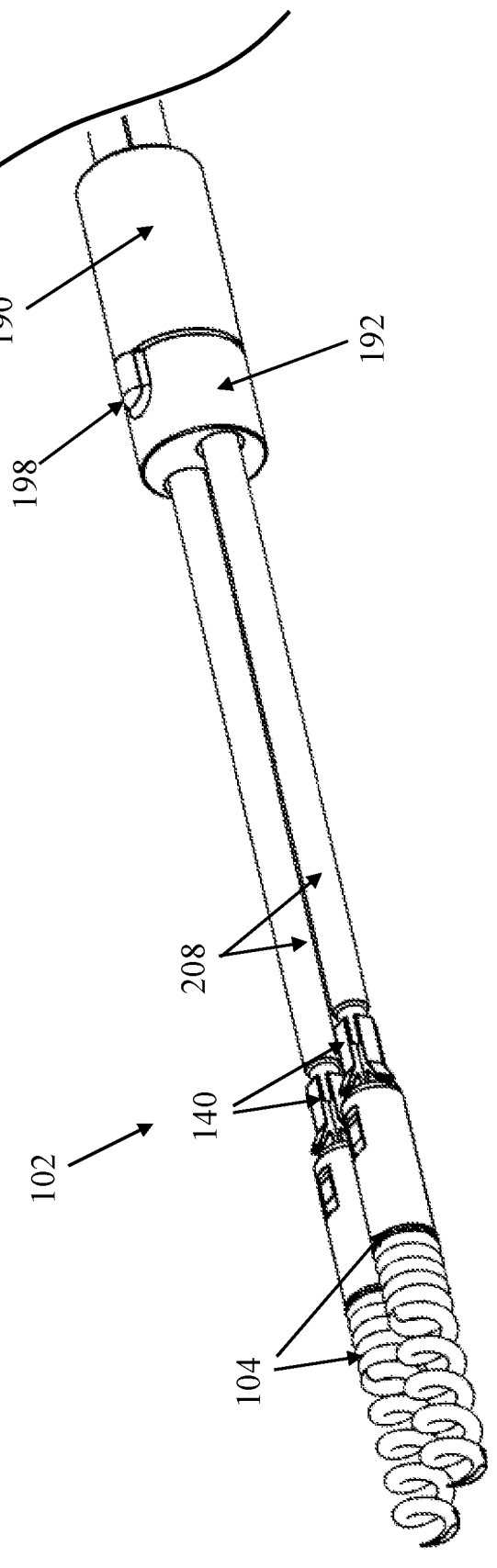
FIG. 31C is a perspective view of the tissue recruiting assembly of FIG. 31B with the shroud removed.
Figure 32A:
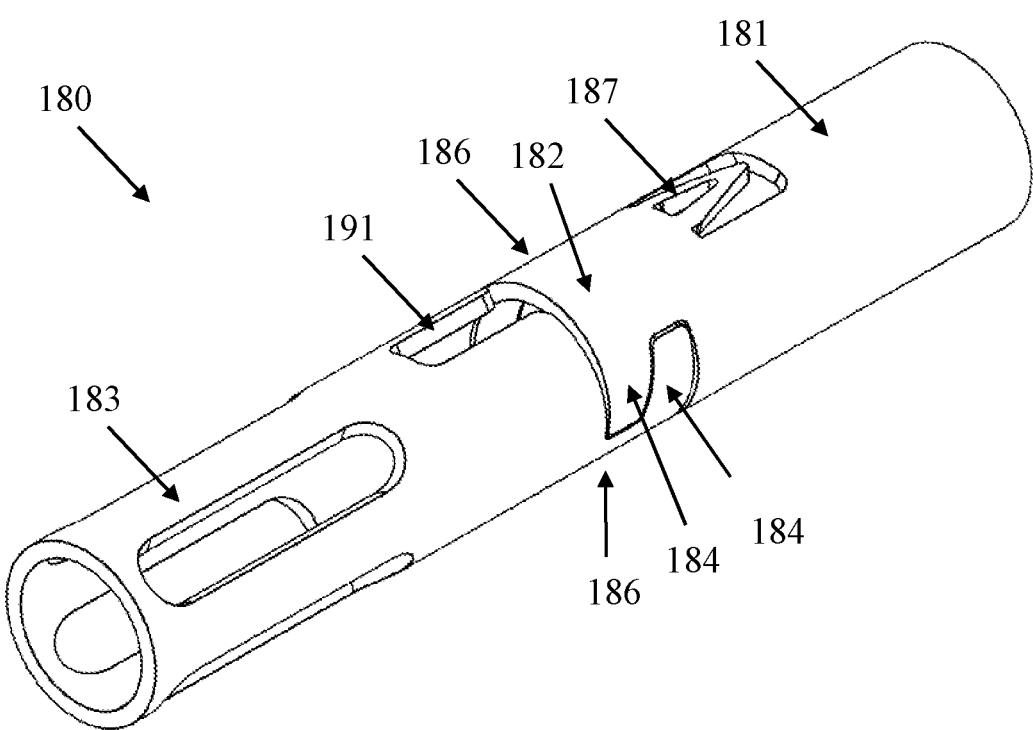
FIGS. 32A and 32B show various views of the connector of the tissue recruiting assembly of FIG. 31A.
Figure 32B:
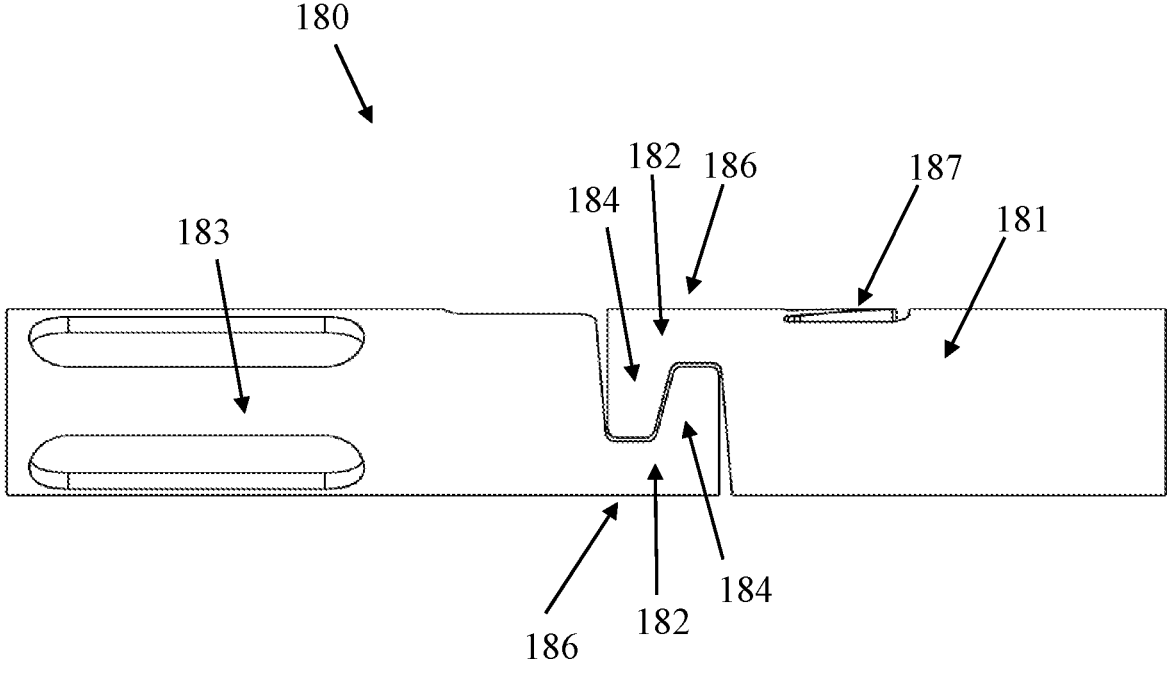
Figure 32C:
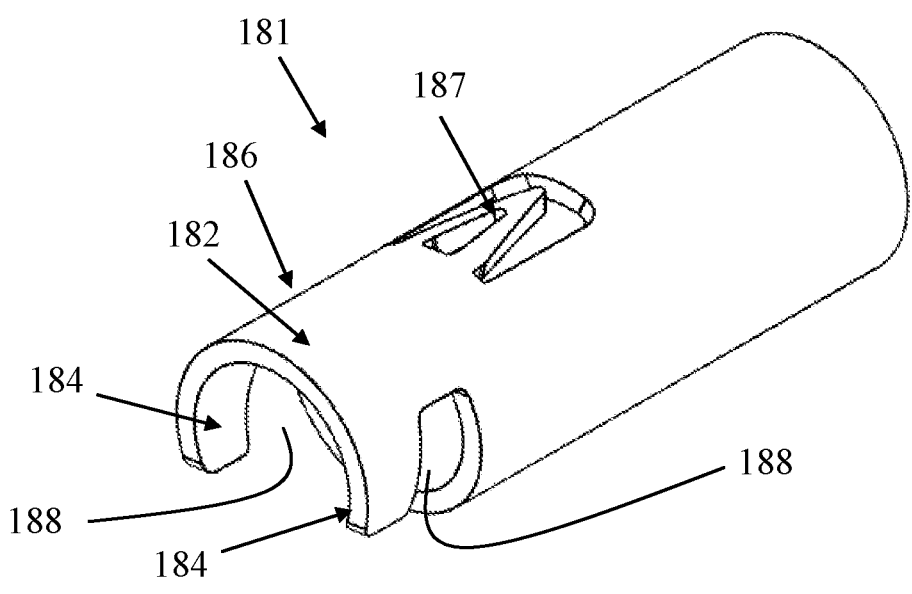
FIGS. 32C and 32D are front and rear perspective views of the proximal connector portion of the connector of FIGS. 32A and 32B.
Figure 32D:
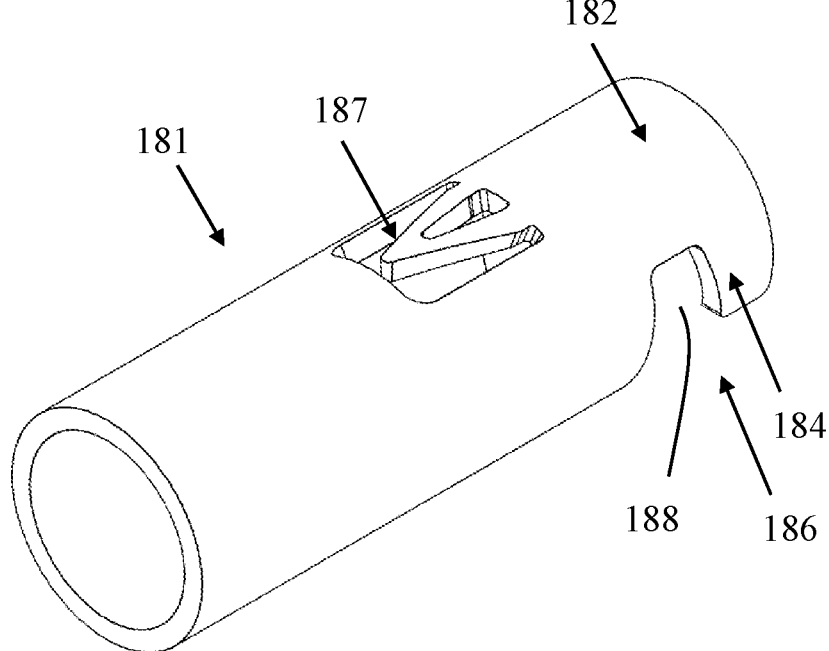
Figure 32E:
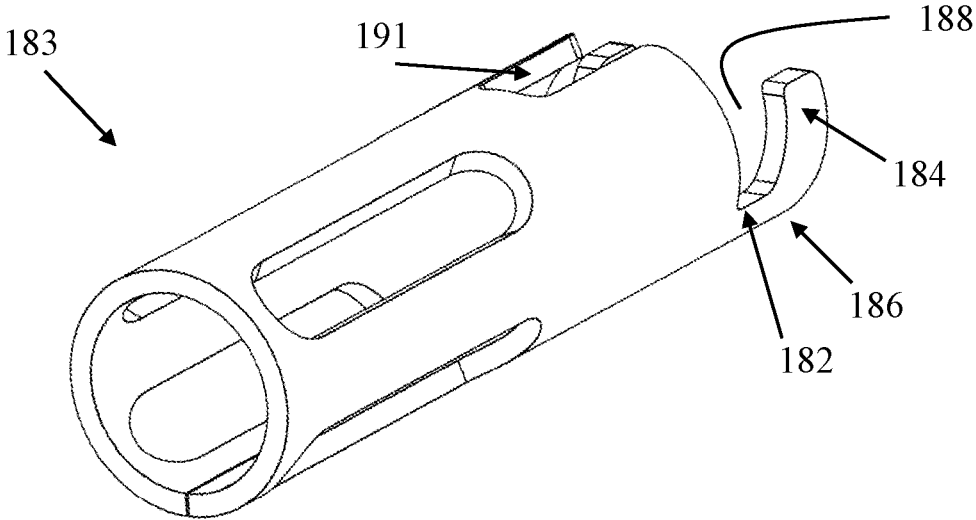
FIGS. 32E and 32F are front and rear perspective views of the distal connector portion of the connector of FIGS. 32A and 32B.
Figure 32F:
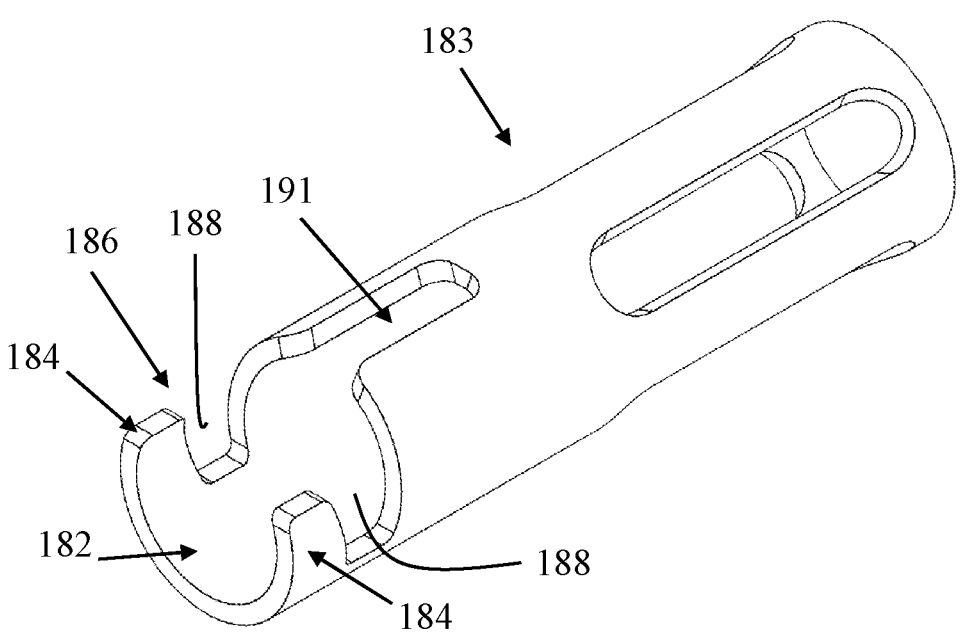

As shown in FIGS. 31A-32F and 36-38B, the release member 192 may include a projection 198 extending radially outwardly from the outer surface of the release member 192. The projection 198 may be disposed near the proximal end of the release member 192. The projection 198 may extend radially outwardly and into a slot 191 of the distal connector portion 183 during operation (FIG. 31A). The projection 198 and/or the slot 191 may be sized, shaped, and configured to substantially prevent the projection 198 from rotating out of the slot 191. During operation, the projection 198 may be disposed in the slot 191 to maintain the position and/or orientation of the release member 192, such as to maintain the position and/or orientation of the release passages 196 relative to the shroud 170 and distal connector portion 183. The release passages 196 may be oriented via the projection 198 to facilitate control of the actuation elements 208 during the tissue grasping operation. In some embodiments, the projection 198 is fixed, such as via welding, in the slot 191 to secure the release member 192 to the distal connector portion 183.

While the release slider 190 and the release member 192 have been described as being operable with the coupler 140 of FIGS. 28A-28D, it will be understood that the release slider 190 and the release member 192 may be operable to decouple the grasping devices 104 from the actuation elements 208 and to decouple the proximal and distal connector portions 181, 183 and in other manners. For example, the release slider 190 and the release member 192 may be used with the connection between the grasping device 104 and actuation element 208 described in FIGS. 22A-22B, with any of the couplers 140 described in FIGS. 23A-27B, the coupler 140 of FIGS. 29A-29B, or any other coupler 140 described herein.

Figures 39A, 39B:
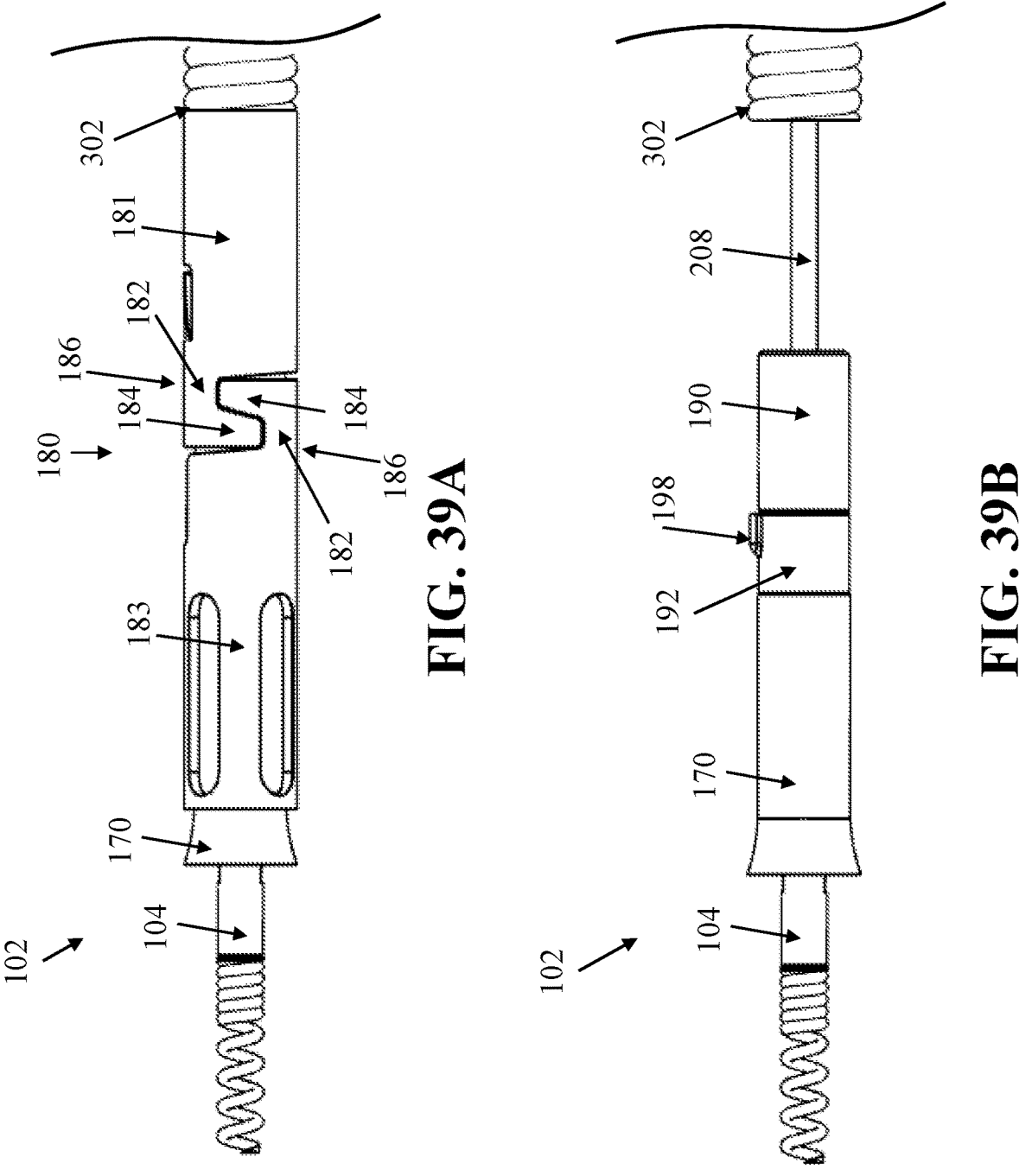
FIGS. 39A-39H are side views illustrating the operation of the tissue recruiting device of FIG. 31A to operate the grasping devices to grasp tissue, retract the grasped tissue into the shroud, decouple the grasping devices from the actuation elements; and decouple the shroud from the catheter to maintain closure of a defect.
Figures 39C, 39D:
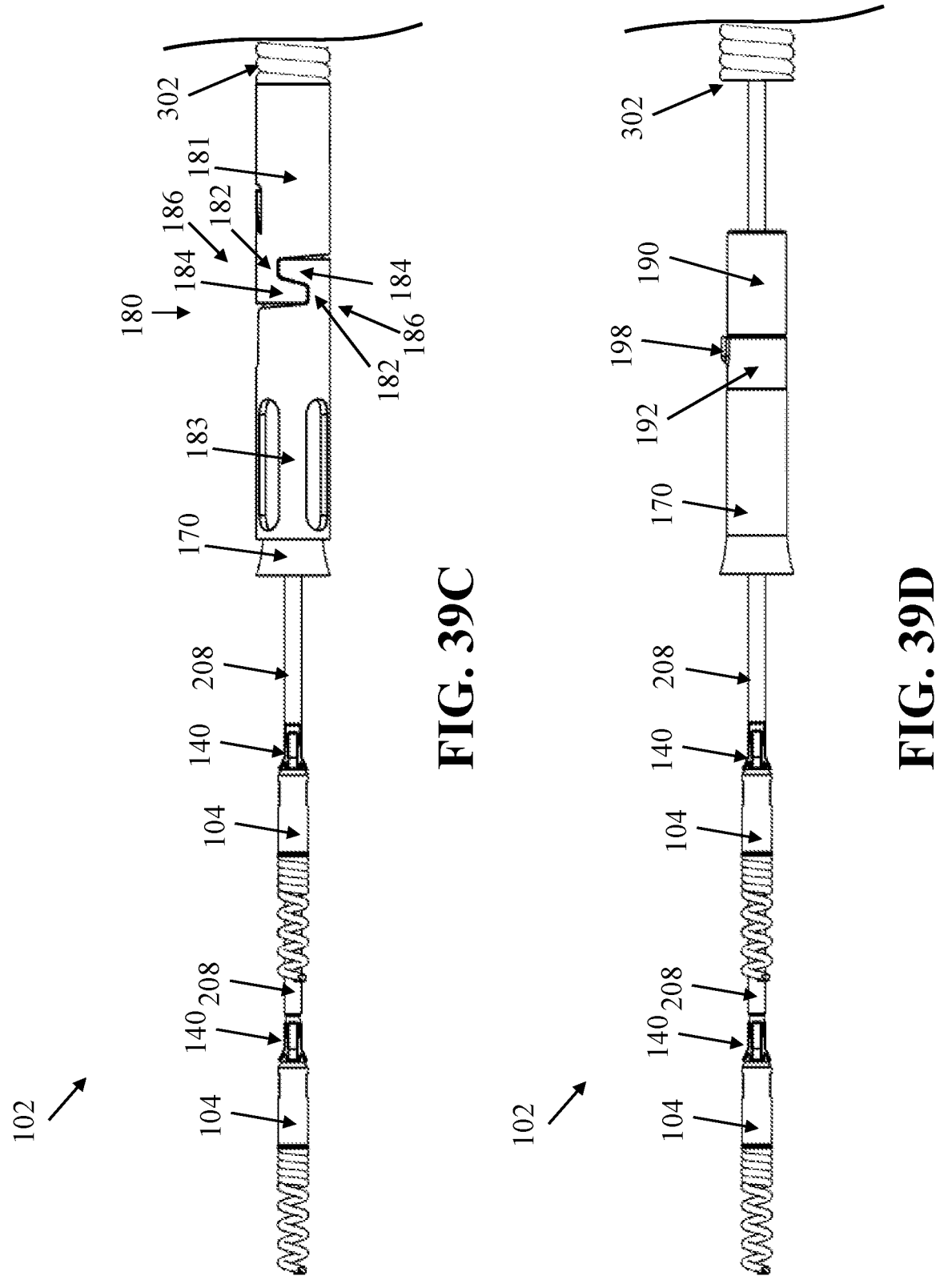
Figures 39E, 39F:
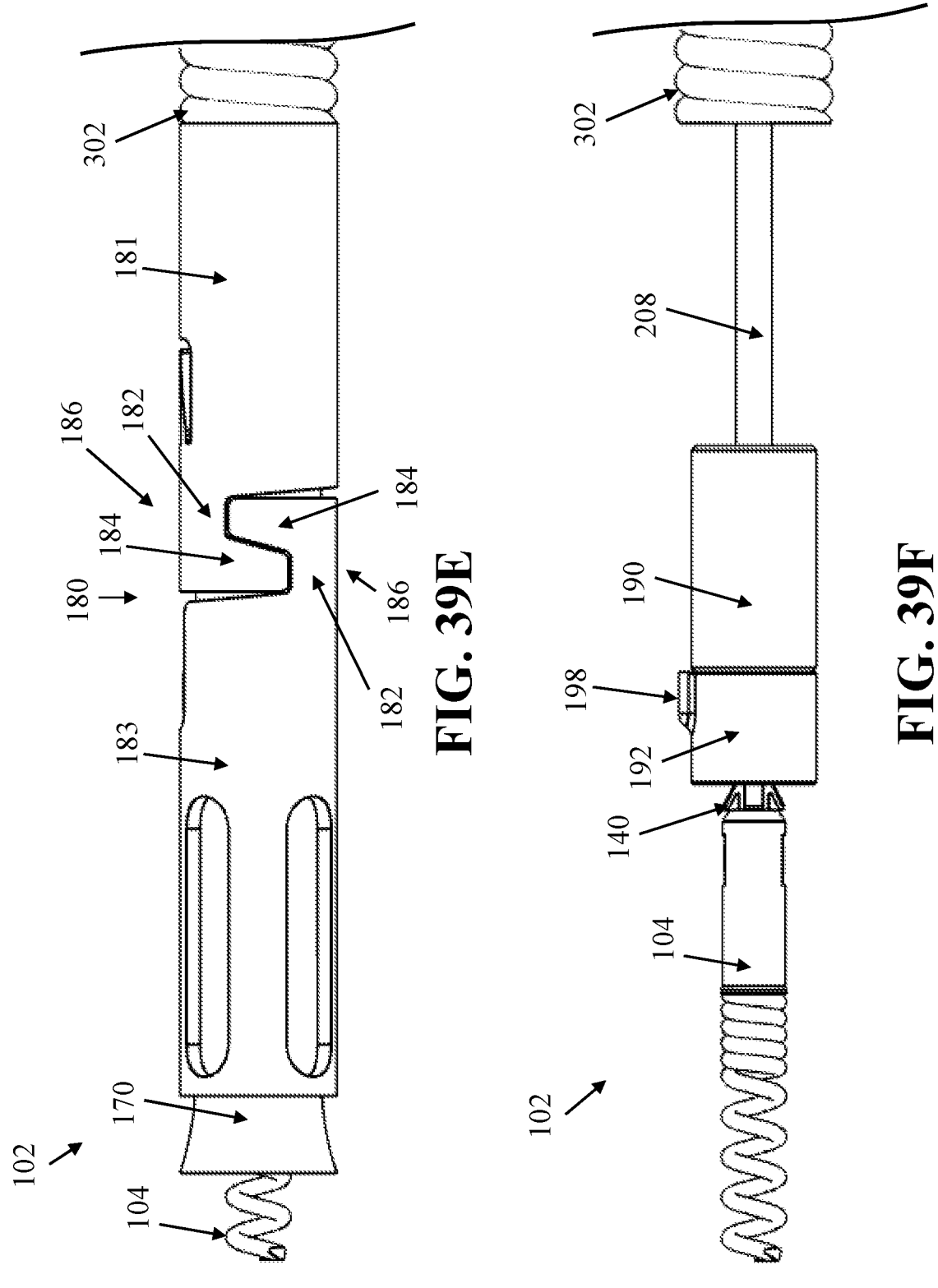
Figures 39G, 39H:
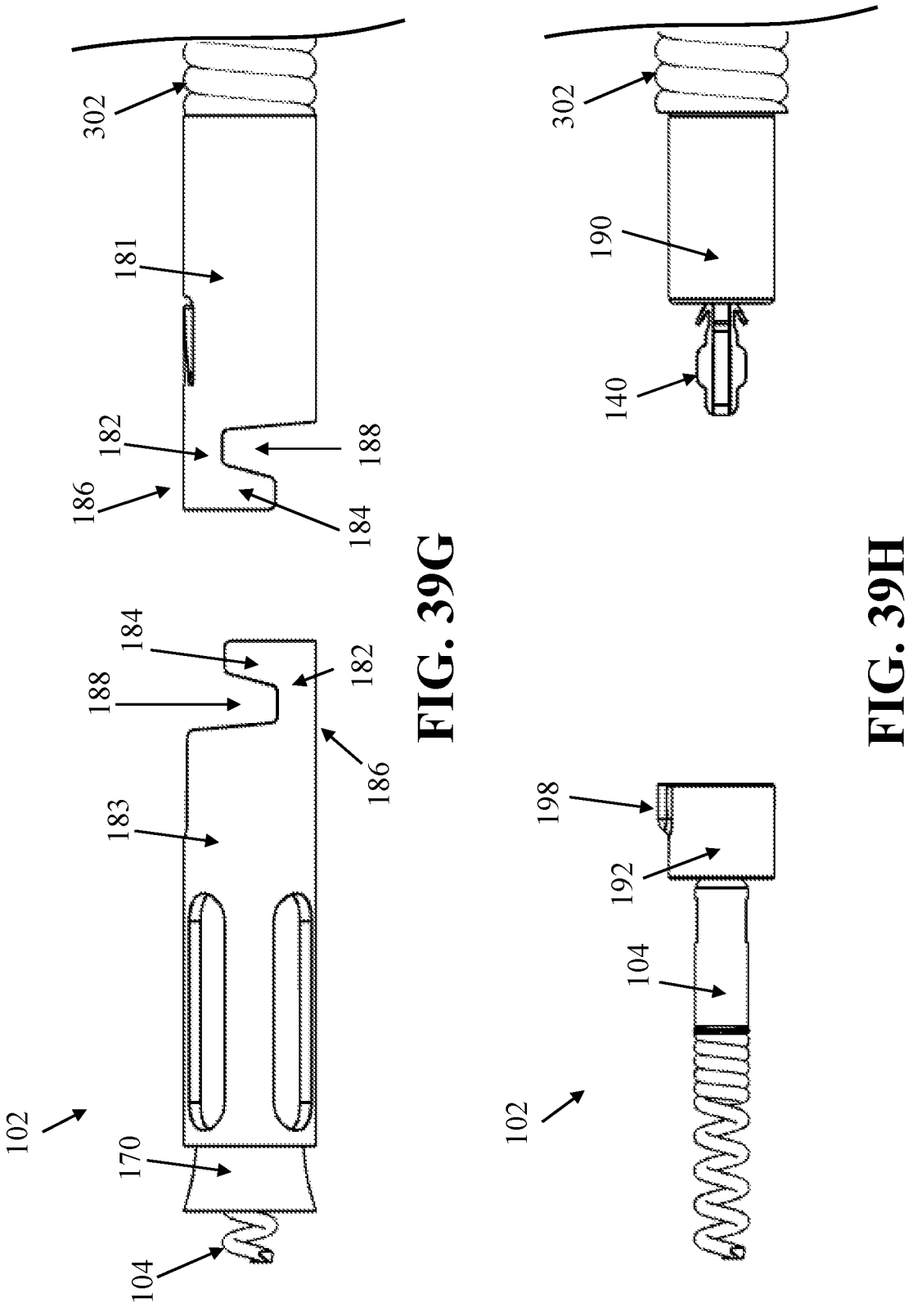

Referring now to FIGS. 39A-39H, two or more grasping devices 104 may be secured in tissue, such as on multiple sides of a defect, brought together to close the defect, and secured in a locked position. The grasping devices 104, shroud 170, and distal connector portion 183 may then be decoupled from remainder of the tissue recruiting device 100, such as to maintain closure of the defect in the tissue recruitment area 172 of the shroud 170 via the grasping devices 104 and without the need for a hemostatic clip. FIGS. 39B, 39D, 39F, and 39H show the tissue recruiting assembly 102 without the proximal and distal connector portions 181, 183 and FIGS. 39F and 39H show the tissue recruiting assembly 102 also without the shroud 170.

As shown in FIGS. 39A-39B, the tissue recruiting assembly 102 may be extended through a catheter 302, such as through an endoscope, to a desired location, such as above a defect. The proximal connector portion 181 may be connected to the distal end of the catheter 302 and the distal connector portion 183 may be coupled with the proximal connector portion 181 via the connecting portions 186. The distal connector portion 183 may be connected to the shroud 170. The release slider 190 may be disposed within the proximal and distal connector portions 181, 183 in the operational position to maintain the coupling of the connecting portions 186 of the proximal and distal connector portions 181, 183. For example, the retention tab 187 may be bent or flexed radially inwardly to maintain the release slider 190 in the operational position. The release member 192 may be disposed within the distal connector portion 183, such as at a proximal end of the shroud 170. The grasping devices 104 may be partially or wholly disposed in the shroud 170. Actuation elements 208 may extend through the catheter 302, the release slider 190, and the release member 192 and into the shroud 170 to couple with each grasping device 104. Each actuation element 208 may be coupled to one of the grasping devices 104 via a coupler 140 (FIGS. 39C-39F). In the illustrated embodiment, the catheter 302 is a spring sheath comprising a coiled metal. However, it will be understood that the catheter 302 may have other configurations.

As shown in FIGS. 39C and 39D, the actuation elements 208 may be extended through the catheter 302 to maneuver the grasping devices 104 to grasp tissue. The actuation elements 208 may be translated and rotated, such as via the actuation assembly 200, such that the grasping devices pierce and spiral into tissue such that the helical coils 114 are graspingly inserted into the tissue. The grasping devices 104 may be independently actuated such that the grasping devices 104 grasp tissue on opposite sides of a defect. The shroud 170 remains coupled to the catheter 302 via the proximal and distal connector portions 181, 183 of the connector 180 and the grasping devices 104 remain coupled to the actuation elements 208 via the couplers 140.

As shown in FIGS. 39E and 39F, the actuation elements 208 may be proximally retracted, such as via the actuation assembly 200, such that the grasping devices 104 are moved to a locked position within the shroud 170 and/or the with the release member 192. For example, the grasping devices 104 may be proximally retracted after grasping tissue on opposite sides of a defect such that the grasped tissue is recruited toward or into the tissue recruitment area 172 of the shroud 170 to substantially close the defect. The actuation elements 208 may be retracted to retract the grasping devices 104 into the locked position in the shroud 170 and/or the release member 192. The actuation elements 208 may be retracted such that the couplers 140 extend at least partially through the release passages 196 of the release member 192. In some embodiments, the actuation elements 208 may also be retracted such that the couplers 140 partially extend into the actuation passages 194 of the release slider 190. In other embodiments, the actuation elements 208 may be retracted such that the proximal end of the couplers 140 abut the distal surface of the release slider 190.

The grasping devices 104 may be disposed on the distal side of the release member 192, such as with the grasping portions 112 disposed on the distal side of the release member 192 to recruit tissue, and remain in the locked position relative to the shroud 170 and the distal connector portion 183. The shroud 170 remains operably coupled to the catheter 302 via the proximal and distal connector portions 181, 183 of the connector 180 and the grasping devices 104 remain operably coupled to the actuation elements 208 via the couplers 140 as the grasping devices 104 are moved in the locked position.

As shown in FIGS. 39G and 39H, the actuation elements 208 may be decoupled from the grasping devices 104 and the catheter 302 may be decoupled from the shroud 170. The actuation elements 208 may be proximally retracted such that the couplers 140 are pulled proximally through the release passages 196 of the release member 192 with the grasping devices 104 remaining on the distal side of the release member 192. The release passage 196 may be sized, shaped, and configured such that the grasping devices 104 are prevented from passing through the release passages 196, thereby allowing for the couplers 140 to be released from the coupling portions 110 of the grasping devices 104 and proximally retracted when the actuation elements 208 are proximally retracted. The proximal retraction of the couplers 140 relative to the grasping devices 104 may decouple the actuation elements 208 from the grasping devices 104. The couplers 140 may remain coupled to the distal ends of the actuation elements 208.

The actuation elements 208 may also be proximally retracted to decouple the shroud 170 from the catheter 302. After or while the couplers 140 are retracted through the release passages 196 of the release member 192, the distal end of the actuation element 208 and/or a portion of the couplers 140 may abut or otherwise engage the release slider 190 such that the release slider 190 may be proximally retracted with the actuation elements 208. For example, the prongs 146 of the couplers 140 may abut the distal surface of the release slider 190 such that the release slider 190 may be proximally retracted with the actuation elements 208. The actuation elements 208 may be proximally retracted such that the release slider 190 is proximally retracted from the operational position maintaining the coupling between the proximal and distal connector portions 181, 183. For example, the actuation elements 208 may be proximally retracted with sufficient force to flex or bend the retention tab 187 radially outwardly such that the release slider 190 may be proximally retracted from the operational position. The release slider 190 may be proximally retracted into the proximal connector portion 181 such that the release slider 190 no longer supports the connecting portions 186 of the proximal and distal connector portions 181, 183. The proximal retraction of the release slider 190 may permit the proximal connector portion 181 to decouple from the distal connector portion 183.

The grasping devices 104 may remain retracted into the shroud 170, such as with the grasped tissue. The grasping devices 104 may remain locked in the retracted position by the shroud 170 and/or the release member 192. For example, the grasping devices 104 may be locked in the retracted position via a frictional/compressional fit, locking tabs, and/or locking features within the proximal end of the shroud 170 and/or of the release member 192 that operate with the grasping devices 104 to maintain the translational and rotational positions of the grasping devices 104.

The retraction of the grasping devices 104 into the tissue recruitment area 172 of the shroud 170 may maintain substantial closure of the defect such that a hemostatic clip is not needed to close the defect. The grasping devices 104, shroud 170, distal connector portion 183, and release member 192 may be decoupled from the actuation elements 208, couplers 140, release slider 190, and catheter 302. The grasping devices 104 and shroud 170 may remain deployed in the tissue, such as to maintain closure of the defect. After the actuation elements 208, couplers 140, release slider 190, proximal connector portion 181, and catheter 302 are decoupled from the grasping devices 104, shroud 170, distal connector portion 183, and release member 192, the actuation elements 208, couplers 140, release slider 190, proximal connector portion 181, and catheter 302 may be withdrawn from the body. The grasping devices 104, shroud 170, distal connector portion 183, and release member 192 may remained deployed in the body to maintain closure of the tissue.

FIG. 40 illustrates an exemplary methodology 400 relating to deploying grasping devices to close a defect. While the methodology is shown as being a series of acts that are performed in a sequence, it is to be understood and appreciated that the methodology is not limited by the order of the sequence. For example, some acts can occur concurrently with another act. Further, in some instances, not all acts may be required to implement the methodology described herein.

At step 402, grasping devices are positioned above an identified defect. The grasping devices may be incorporated into a tissue recruiting assembly of a tissue recruiting device. The grasping devices may be coupled to an actuation assembly via actuation elements such that a user may control the position and rotation of the grasping devices. As described above, the grasping devices may include helical coils configured to pierce and spiral into tissue to grasp the target tissue. The grasping devices may be extended through a catheter which is inserted through an endoscope to the desired location.

At step 404, a first side of the defect is grasped with one of the grasping devices. The first grasping device may be controlled via a first actuation element, such as via the actuation assembly, to translate and rotate such that the first grasping device pierces into and grasps the tissue on the first side of the defect.

At step 406, a second side of the defect is grasped with the other grasping device. The grasping device may be positioned above the second side of the defect by maneuvering the endoscope and/or the catheter. The second grasping device may be independently controlled via a second actuation element, such as via the actuation assembly, to translate and rotate such that the second grasping device pierces into and grasps the tissue on the second side of the defect. The first grasping device may continue to grasp the tissue on the first side of the defect as the second grasping device is maneuvered.

In steps 404 and 406, the tissue may be pulled toward the distal end of the catheter as the tissue is being grasped. For example, the catheter may be retracted as the tissue is being grasped. Pulling the tissue toward the catheter may pull the tissue away from adjacent organs (e.g., organs on the outside wall of the grasped tissue), such as to prevent the grasping devices from contacting the organs.

Further, while the first grasping device has been described as grasping tissue at a first location and the second tissue is described as grasping tissue at a second location, it will be understood that the first and second grasping devices may be used at the same location. For example, the first grasping device may grasp tissue to initially pull the tissue toward the catheter, such as away from an organ, and the second grasping device may be maneuvered to securely grasp the tissue pulled by the first grasping device. The second grasping device may then be used to provide tension on the tissue, such as via the actuation element, such that the first grasping device may be maneuvered to securely grasp the tissue.

At step 408, the grasped tissue is retracted into the shroud. As described above, the actuation elements may be proximally retracted, such as via the actuation assembly, such that the grasping devices are retracted into the shroud. Additionally, the catheter may be advanced toward the defect to aid in maneuvering the grasping devices into the shroud. The grasping devices may recruit the grasped tissue into a tissue recruiting area of the shroud. Recruiting the grasped tissue from opposite sides of the defect may substantially close the defect.

At step 410, the grasping devices are locked in the shroud. As described above, the grasping devices may be locked in the shroud in the retracted positions such that the grasped tissue remains recruited into the tissue recruiting area of the shroud, such as to substantially close the defect.

A step 412, the grasping devices are decoupled from the actuation elements. As described above, the actuation elements may be retracted farther such that the grasping devices are decoupled from the actuation elements. In some embodiments, the proximal retraction of the actuation elements decouples the grasping devices from couplers coupled to the distal ends of the actuation elements. In some embodiments, the actuation elements and couplers are pulled through a release member such that the couplers are pulled out of coupling from the grasping devices, as described above.

At step 414, the shroud is decoupled from the catheter. As described above, retraction of the actuation elements may decouple the shroud from a connector connected to the distal end of the catheter. In some embodiments, the shroud is connected to a distal connector portion which is decoupled from a proximal connector portion which is connected to the distal end of the catheter. The coupling of the proximal and distal connector portions may be maintained during the tissue grasping operation by a release slider disposed beneath the connecting portions of the proximal and distal connector portions. In some embodiments, retraction of the actuation elements proximally retracts the release slider such that the release slider no longer maintains the coupling of the proximal and distal connector portions such that the proximal and distal connector portions may decouple. For example, the distal ends of the actuation elements and/or portions of the couplers may contact the release slider such that the release slider is pulled out of the operational position when the actuation elements are proximally retracted. The decoupling of the proximal and distal connector portions may decouple the catheter from the shroud.

At step 416, the catheter and actuation elements are retracted from the body. The grasping devices and the shroud may be separated from the actuation elements and the catheter. The grasping devices 104 may remain retracted into the shroud, such as with the grasped tissue. The retraction of the grasping devices into the tissue recruiting area of the shroud may maintain substantial closure of the defect such that a hemostatic clip is not needed to close the defect. After the catheter and actuation elements are retracted from the body, the grasping devices and the shroud may remain in the body to maintain the closure of the defect.

It is to be understood that the detailed description is intended to be illustrative, and not limiting to the embodiments described. Other embodiments will be apparent to those of skill in the art upon reading and understanding the above description. Moreover, in some instances, elements described with one embodiment may be readily adapted for use with other embodiments. Therefore, any products, methods and/or systems described herein are not limited to the specific details, the representative embodiments, and/or the illustrative examples shown and described. Accordingly, departures may be made from such details without departing from the spirit or scope of the general aspects of the present disclosure.

Additionally, the components and materials described hereinafter as making up the various embodiments are intended to be illustrative and not restrictive. It should be appreciated that many suitable components and materials that would perform the same or a similar function as the materials described herein are intended to be embraced within the scope of embodiments of the present disclosure.

We claim:

1. A tissue recruiting device comprising:
   a catheter;
   a tissue recruiting assembly comprising:
      first and second grasping devices; and
      a shroud operably coupled with the catheter and configured to at least partially surround the grasping devices in a retracted position; and
   an actuation assembly comprising:
      a first control actuator coupled with a first actuation element, the first actuation element being operably coupled with the first grasping device; and
      a second control actuator coupled with a second actuation element, the second actuation element being operably coupled with the second grasping device;
   wherein the first control actuator is operable to maneuver the first grasping device to grasp tissue at a first location and the second control actuator is operable to maneuver the second grasping device to grasp tissue at a second location; and
   wherein the grasping devices may be decoupled from the actuation elements and the shroud may be decoupled from the catheter when the grasping devices grasp tissue.

2. The tissue recruiting device of claim 1, wherein each grasping device is operably coupled to the respective actuation element by a coupler.

3. The tissue recruiting device of claim 2, wherein the coupler is fixed to a distal end of the actuation element and includes outwardly biased prongs configured to be received in a receiving portion of the grasping device.

4. The tissue recruiting device of claim 3, wherein prongs of the coupler include projections configured to be received in detents of the coupling portion of the grasping device to operably couple the coupler to the grasping device.

5. The tissue recruiting device of claim 1, wherein the shroud is operably coupled to the catheter by a connector.

6. The tissue recruiting device of claim 1, wherein the actuation elements are operable to recruit the grasping devices into the shroud before the grasping devices are decoupled from the actuation elements and the shroud is decoupled from the catheter when the grasping devices grasp tissue.

7. The tissue recruiting device of claim 1, further comprising a release member operable to decouple the grasping devices from the actuation elements via proximal retraction of the actuation elements.

8. A tissue recruiting assembly of a tissue recruiting device operable to extend through a catheter and grasp tissue, the tissue recruiting assembly comprising:
   a first grasping device operably coupled to a first actuation element by a first coupler;
   a second grasping device operably coupled to a second actuation element by a second coupler;
   a shroud configured to surround the first and second grasping devices; and
   a connector configured to operably couple the shroud to the catheter;
   wherein the first grasping device may be controlled by the first actuation element to grasp tissue at a first location and the second grasping device may be controlled by the second actuation element to grasp tissue at a second location;
   wherein the grasping devices may be retracted into the shroud and locked in place when grasping tissue; and
   wherein the grasping devices are operably decoupled from the actuation elements and the shroud is operably decoupled from the catheter after the grasping devices are retracted into the shroud.

9. The tissue recruiting assembly of claim 8, wherein the connector includes a proximal connector portion fixed to the catheter and a distal connector portion fixed to the shroud.

10. The tissue recruiting assembly of claim 8, wherein each coupler comprises a coupling link which operably couples the actuation element to the grasping device.

11. The tissue recruiting assembly of claim 8, further comprising a release slider disposed operable to decouple the grasping devices from the couplers when the actuation elements are proximally retracted.

12. The tissue recruiting assembly of claim 8, wherein the grasping devices each have a plurality of helical coils for grasping tissue.

13. The tissue recruiting assembly of claim 8, wherein the grasping devices and shroud are configured to maintain closure of a defect after the grasping devices are decoupled from the actuation elements and the shroud is decoupled from the catheter.

14. The tissue recruiting assembly of claim 8, wherein the shroud is configured to decrease in length when the grasping devices grasp tissue and are retracted into the shroud.

15. A method for treating a defect with a tissue recruiting device, the method comprising the steps of:

grasping a first side of the defect with a first grasping device via a first actuation element;

grasping a second side of the defect with a second grasping device via a second actuation element;

retracting the first and second grasping devices into a shroud coupled to a catheter;

decoupling the first grasping device from the first actuation element and the second grasping device from the second actuation element; and decoupling the shroud from the catheter.

16. The method of claim 15, wherein each grasping device is coupled to the respective actuation element by a coupler.

17. The method of claim 15, wherein each grasping device includes helical coils and the actuation elements are operable to translate and rotate the grasping devices to grasp tissue.

18. The method of claim 15, wherein the grasping devices are decoupled from the actuation elements by proximal retraction of the actuation elements.

19. The method of claim 15, further comprising the step of retracting the catheter and the actuation elements from the grasping devices and the shroud.

20. The method of claim 15, further comprising the step of locking the grasping devices in the shroud.

\* \* \* \* \*